(12) United States Patent
Van Maris et al.

(10) Patent No.: US 9,303,253 B2
(45) Date of Patent: Apr. 5, 2016

(54) METABOLIC ENGINEERING OF ARABINOSE-FERMENTING YEAST CELLS

(75) Inventors: Antonius Jeroen Adriaan Van Maris, Delft (NL); Jacobus Thomas Pronk, Schipluiden (NL); Hendrik Wouter Wisselink, Culemborg (NL); Johannes Pieter Van Dijken, Leidschendam (NL); Aaron Adriaan Winkler, The Hague (NL); Johannes Hendrik Winde, Voorhout (NL)

(73) Assignee: DSM IP ASSETS B.V., Herleen (NL)

( * ) Notice: Subject to any disclaimer, the term of this patent is extended or adjusted under 35 U.S.C. 154(b) by 308 days.

(21) Appl. No.: 13/345,146

(22) Filed: Jan. 6, 2012

(65) Prior Publication Data

US 2012/0208231 A1 Aug. 16, 2012

Related U.S. Application Data

(63) Continuation of application No. 12/442,013, filed as application No. PCT/NL2007/000246 on Oct. 1, 2007, now abandoned.

(60) Provisional application No. 60/848,357, filed on Oct. 2, 2006.

(30) Foreign Application Priority Data

Oct. 2, 2006 (EP) .................................. 06121633

(51) Int. Cl.

| | | |
|---|---|---|
| *C12P 35/00* | (2006.01) | |
| *C12P 7/40* | (2006.01) | |
| *C12P 7/06* | (2006.01) | |
| *C12N 9/00* | (2006.01) | |
| *C12N 1/20* | (2006.01) | |
| *C12N 15/00* | (2006.01) | |
| *C07H 21/04* | (2006.01) | |
| *C12N 9/90* | (2006.01) | |
| *C12N 9/12* | (2006.01) | |
| *C12P 7/08* | (2006.01) | |

(52) U.S. Cl.

CPC ............... *C12N 9/90* (2013.01); *C12N 9/1205* (2013.01); *C12P 7/08* (2013.01); *Y02E 50/17* (2013.01)

(58) Field of Classification Search

None

See application file for complete search history.

(56) References Cited

U.S. PATENT DOCUMENTS

2008/0261287 A1 10/2008 Winkler et al.

FOREIGN PATENT DOCUMENTS

| WO | 2006/009434 | 1/2006 |
|---|---|---|
| WO | 2006096130 A1 | 9/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Kuyper et al., "Metabolic engineering of a xylose-isomerase-expressing *Saccharomyces cerevisiae* strain for rapid anaerobic xylose fermentation", FEMS Yeast Res. Feb. 2005; 5(4-5):399-409.
Butaloc Third Party observations—Sep. 29, 2008.
Form 1139 Third Party Observations by BUTALCO—Dec. 3, 2008.
Karthumaa et al., "Co-utilization of L-arabinose and D-xylose by laboratory and industrial *Saccharomyces cerevisiae* strains", Microbial Cell Factories 5:18 (2006).
Sedlak and Ho, "Expression of *E.coli* araBAD operon encoding enzymes for metabolizing L-arabinose in *Saccharomyces cerevisiae*", Enzyme and Microbial Technology 28:16-24 (2001).
Wisselink et al., "Engineering of *Saccharomyces cerevisiae* for Efficiency Anaerobic Alcoholic Fermentation of L-Arabinose", Applied and Environmental Microbiology 73(15):4881-4891 (2007).
Becker & Boles, "A modified *Saccharomyces cerevisiae* strain that consumes L-arabinose and produces ethanol", Appl Environ Microbiol, vol. 69, No. 7, pp. 4144-4150 (Jul. 2003).
Deanda et al., "Development of an arabinose-fermenting *Zymomonas mobilis* strain by metabolic pathway engineering", Appl Environ Microbiol, vol. 62, No. 12, pp. 4465-4470 (Dec. 1996).
Kleerebezem et al., "Complete genome sequence of *Lactobacillus plantarum* WCFS1", Proc Natl Acad Sci USA, vol. 100, No. 4, pp. 1990-1995 (Feb. 2003); Database Accession No. Q88S82 (Jun. 1, 2003); Database Accession No. Q88S83 (Jun. 1, 2003): Database Accession No. Q88S84 (Jun. 1, 2003).
International Search Report for PCT/NL2007/000246, four pages, mailed Jan. 11, 2008.
International Search Report on Patentability for PCT/NL2007/000246, six pages, mailed Apr. 7, 2009.

* cited by examiner

*Primary Examiner* — Christian Fronda
(74) *Attorney, Agent, or Firm* — MMWV IP, LLC.

(57) ABSTRACT

The invention relates to an eukaryotic cell expressing nucleotide sequences encoding the ara A, ara B and ara D enzymes whereby the expression of these nucleotide sequences confers on the cell the ability to use L-arabinose and/or convert L-arabinose into L-ribulose, and/or xylulose 5-phosphate and/or into a desired fermentation product such as ethanol. Optionally, the eukaryotic cell is also able to convert xylose into ethanol.

27 Claims, 3 Drawing Sheets

METABOLIC ENGINEERING OF ARABINOSE-FERMENTING YEAST CELLS

CROSS REFERENCE TO RELATED APPLICATIONS

This application is a continuation of U.S. application Ser. No. 12/442,013, filed Jun. 12, 2009, which is a U.S. national phase of Int'l Appln. No. PCT/NL2007/00246, filed Oct. 1, 2007, which designated the U.S. and claims priority to Appln. No. EP 06121633.9 filed Oct. 2, 2006, and Appln. No. U.S. 60/848,357, filed Oct. 2, 2006; the entire contents of each of which are hereby incorporated by reference.

FIELD OF THE INVENTION

The invention relates to an eukaryotic cell having the ability to use L-arabinose and/or to convert L-arabinose into L-ribulose, and/or xylulose 5-phosphate and/or into a desired fermentation product and to a process for producing a fermentation product wherein this cell is used.

BACKGROUND OF THE INVENTION

Fuel ethanol is acknowledged as a valuable alternative to fossil fuels. Economically viable ethanol production from the hemicellulose fraction of plant biomass requires the simultaneous fermentative conversion of both pentoses and hexoses at comparable rates and with high yields. Yeasts, in particular *Saccharomyces* spp., are the most appropriate candidates for this process since they can grow and ferment fast on hexoses, both aerobically and anaerobically. Furthermore they are much more resistant to the toxic environment of lignocellulose hydrolysates than (genetically modified) bacteria.

EP 1 499 708 describes a process for making *S. cerevisiae* strains able to produce ethanol from L-arabinose. These strains were modified by introducing the araA (L-arabinose isomerase) gene from *Bacillus subtilis*, the araB (L-ribulokinase) and araD (L-ribulose-5-P4-epimerase) genes from *Escherichia coli*. Furthermore, these strains were either carrying additional mutations in their genome or overexpressing a TAL1 (transaldolase) gene. However, these strains have several drawbacks. They ferment arabinose in oxygen limited conditions. In addition, they have a low ethanol production rate of 0.05 g·g$^{-1}$·h$^{-1}$ (Becker and Boles, 2003). Furthermore, these strains are not able to use L-arabinose under anaerobic conditions. Finally, these *S. cerevisiae* strains have a wild type background, therefore they can not be used to co-ferment several C5 sugars.

WO 03/062430 and WO 06/009434 disclose yeast strains able to convert xylose into ethanol. These yeast strains are able to directly isomerise xylose into xylulose.

Still, there is a need for alternative strains for producing ethanol, which perform better and are more robust and resistant to relatively harsh production conditions.

DESCRIPTION OF THE INVENTION

Eukaryotic Cell

Figure 1:
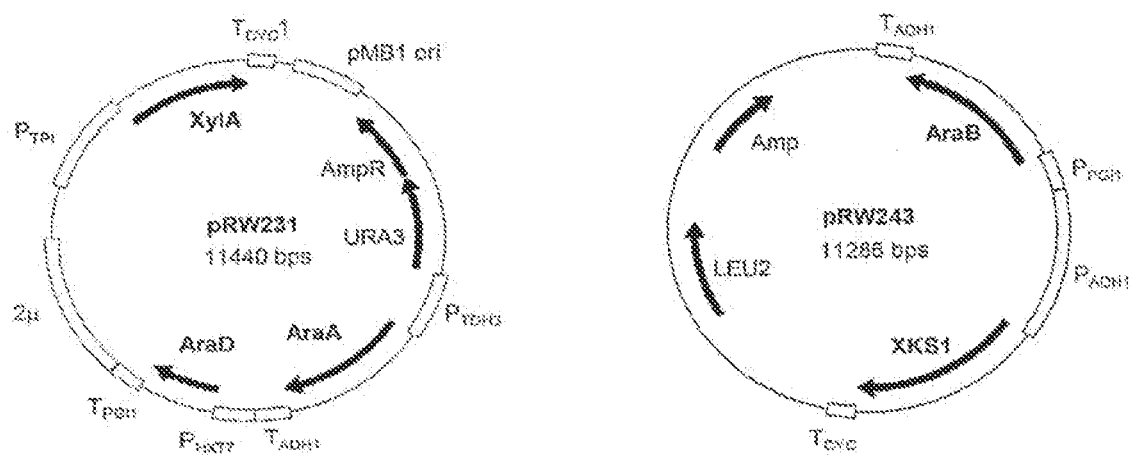
FIG. 1. Plasmid maps of pRW231 and pRW243.

In a first aspect, the invention relates to a eukaryotic cell capable of expressing the following nucleotide sequences, whereby the expression of these nucleotide sequences confers on the cell the ability to use L-arabinose and/or to convert L-arabinose into L-ribulose, and/or xylulose 5-phosphate and/or into a desired fermentation product such as ethanol:

(a) a nucleotide sequence encoding an arabinose isomerase (araA), wherein said nucleotide sequence is selected from the group consisting of:
  (i) nucleotide sequences encoding an araA, said araA comprising an amino acid sequence that has at least 55% sequence identity with the amino acid sequence of SEQ ID NO:1.
  (ii) nucleotide sequences comprising a nucleotide sequence that has at least 60% sequence identity with the nucleotide sequence of SEQ ID NO:2.
  (iii) nucleotide sequences the complementary strand of which hybridizes to a nucleic acid molecule of sequence of (i) or (ii);
  (iv) nucleotide sequences the sequences of which differ from the sequence of a nucleic acid molecule of (iii) due to the degeneracy of the genetic code, (b) a nucleotide sequence encoding a L-ribulokinase (araB), wherein said nucleotide sequence is selected from the group consisting of:
  (i) nucleotide sequences encoding an araB, said araB comprising an amino acid sequence that has at least 20% sequence identity with the amino acid sequence of SEQ ID NO:3.
  (ii) nucleotide sequences comprising a nucleotide sequence that has at least 50% sequence identity with the nucleotide sequence of SEQ ID NO:4.
  (iii) nucleotide sequences the complementary strand of which hybridizes to a nucleic acid molecule of sequence of (i) or (ii);
  (iv) nucleotide sequences the sequences of which differ from the sequence of a nucleic acid molecule of (iii) due to the degeneracy of the genetic code,
(c) a nucleotide sequence encoding an L-ribulose-5-P-4-epimerase (araD), wherein said nucleotide sequence is selected from the group consisting of:
  (i) nucleotide sequences encoding an araD, said araD comprising an amino acid sequence that has at least 60% sequence identity with the amino acid sequence of SEQ ID NO:5.
  (ii) nucleotide sequences comprising a nucleotide sequence that has at least 60% sequence identity with the nucleotide sequence of SEQ ID NO:6.
  (iii) nucleotide sequences the complementary strand of which hybridizes to a nucleic acid molecule of sequence of (i) or (ii);
  (iv) nucleotide sequences the sequences of which differ from the sequence of a nucleic acid molecule of (iii) due to the degeneracy of the genetic code.

A preferred embodiment relates to an eukaryotic cell capable of expressing the following nucleotide sequences, whereby the expression of these nucleotide sequences confers on the cell the ability to use L-arabinose and/or to convert L-arabinose into L-ribulose, and/or xylulose 5-phosphate and/or into a desired fermentation product such as ethanol:
  (a) a nucleotide sequence encoding an arabinose isomerase (araA), wherein said nucleotide sequence is selected from the group consisting of:
    (i) nucleotide sequences comprising a nucleotide sequence that has at least 60% sequence identity with the nucleotide sequence of SEQ ID NO:2,
    (ii) nucleotide sequences the complementary strand of which hybridizes to a nucleic acid molecule of sequence of (i);
    (iii) nucleotide sequences the sequences of which differ from the sequence of a nucleic acid molecule of (ii) due to the degeneracy of the genetic code,
  (b) a nucleotide sequence encoding a L-ribulokinase (araB), wherein said nucleotide sequence is selected from the group consisting of:
    (i) nucleotide sequences encoding an araB, said araB comprising an amino acid sequence that has at least 20% sequence identity with the amino acid sequence of SEQ ID NO:3.
    (ii) nucleotide sequences comprising a nucleotide sequence that has at least 50% sequence identity with the nucleotide sequence of SEQ ID NO:4.
    (iii) nucleotide sequences the complementary strand of which hybridizes to a nucleic acid molecule of sequence of (i) or (ii);
    (iv) nucleotide sequences the sequences of which differ from the sequence of a nucleic acid molecule of (iii) due to the degeneracy of the genetic code,
  (c) a nucleotide sequence encoding an L-ribulose-5-P-4-epimerase (araD), wherein said nucleotide sequence is selected from the group consisting of:
    (i) nucleotide sequences encoding an araD, said araD comprising an amino acid sequence that has at least 60% sequence identity with the amino acid sequence of SEQ ID NO:5.
    (ii) nucleotide sequences comprising a nucleotide sequence that has at least 60% sequence identity with the nucleotide sequence of SEQ ID NO:6.
    (iii) nucleotide sequences the complementary strand of which hybridizes to a nucleic acid molecule of sequence of (i) or (ii);
    (iv) nucleotide sequences the sequences of which differ from the sequence of a nucleic acid molecule of (iii) due to the degeneracy of the genetic code.

Sequence Identity and Similarity

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by various methods, known to those skilled in the art.

Preferred methods to determine identity are designed to give the largest match between the sequences tested. Methods to determine identity and similarity are codified in publicly available computer programs. Preferred computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, Md. 20894). A most preferred algorithm used is EMBOSS (http://www.ebi.ac.uk/emboss/align). Preferred parameters for amino acid sequences comparison using EMBOSS are gap open 10.0, gap extend 0.5, Blosum 62 matrix. Preferred parameters for nucleic acid sequences comparison using EMBOSS are gap open 10.0, gap extend 0.5, DNA full matrix (DNA identity matrix).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Hybridising Nucleic Acid Sequences

Nucleotide sequences encoding the enzymes expressed in the cell of the invention may also be defined by their capability to hybridise with the nucleotide sequences of SEQ ID NO.'s 2, 4, 6, 8, 16, 18, 20, 22, 24, 26, 28, 30 respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

AraA

A preferred nucleotide sequence encoding a arabinose isomerase (araA) expressed in the cell of the invention is selected from the group consisting of:
(a) nucleotide sequences encoding an araA polypeptide said araA comprising an amino acid sequence that has at least 55, 60, 65, 70, 75, 80, 85, 90, 95, 97, 98, or 99% sequence identity with the amino acid sequence of SEQ ID NO. 1;
(b) nucleotide sequences comprising a nucleotide sequence that has at least 60, 70, 80, 90, 95, 97, 98, or 99% sequence identity with the nucleotide sequence of SEQ ID NO. 2;
(c) nucleotide sequences the complementary strand of which hybridises to a nucleic acid molecule sequence of (a) or (b);
(d) nucleotide sequences the sequence of which differ from the sequence of a nucleic acid molecule of (c) due to the degeneracy of the genetic code.

The nucleotide sequence encoding an araA may encode either a prokaryotic or an eukaryotic araA, i.e. an araA with an amino acid sequence that is identical to that of an araA that naturally occurs in the prokaryotic or eukaryotic organism. The present inventors have found that the ability of a particular araA to confer to a eukaryotic host cell the ability to use arabinose and/or to convert arabinose into L-ribulose, and/or xylulose 5-phosphate and/or into a desired fermentation product such as ethanol when co-expressed with araB and araD does not depend so much on whether the araA is of prokaryotic or eukaryotic origin. Rather this depends on the relatedness of the araA's amino acid sequence to that of the sequence SEQ ID NO. 1.

AraB

A preferred nucleotide sequence encoding a L-ribulokinase (AraB) expressed in the cell of the invention is selected from the group consisting of:
(a) nucleotide sequences encoding a polypeptide comprising an amino acid sequence that has at least 20, 25, 30, 35, 40, 45, 50, 55, 60, 65, 70, 75, 80, 85, 90, 95, 97, 98, or 99% sequence identity with the amino acid sequence of SEQ ID NO. 3;
(b) nucleotide sequences comprising a nucleotide sequence that has at least 50, 60, 70, 80, 90, 95, 97, 98, or 99% sequence identity with the nucleotide sequence of SEQ ID NO.4;
(c) nucleotide sequences the complementary strand of which hybridises to a nucleic acid molecule sequence of (a) or (b);
(d) nucleotide sequences the sequence of which differ from the sequence of a nucleic acid molecule of (c) due to the degeneracy of the genetic code.

The nucleotide sequence encoding an araB may encode either a prokaryotic or an eukaryotic araB, i.e. an araB with an amino acid sequence that is identical to that of a araB that naturally occurs in the prokaryotic or eukaryotic organism. The present inventors have found that the ability of a particular araB to confer to a eukaryotic host cell the ability to use arabinose and/or to convert arabinose into L-ribulose, and/or xylulose 5-phosphate and/or into a desired fermentation product when co-expressed with araA and araD does not depend so much on whether the araB is of prokaryotic or eukaryotic origin. Rather this depends on the relatedness of the araB's amino acid sequence to that of the sequence SEQ ID NO. 3.

AraD

A preferred nucleotide sequence encoding a L-ribulose-5-P-4-epimerase (araD) expressed in the cell of the invention is selected from the group consisting of:
(e) nucleotide sequences encoding a polypeptide comprising an amino acid sequence that has at least 60, 65, 70, 75, 80, 85, 90, 95, 97, 98, or 99% sequence identity with the amino acid sequence of SEQ ID NO. 5;
(f) nucleotide sequences comprising a nucleotide sequence that has at least 60, 65, 70, 75, 80, 85, 90, 95, 97, 98, or 99% sequence identity with the nucleotide sequence of SEQ ID NO.6;
(g) nucleotide sequences the complementary strand of which hybridises to a nucleic acid molecule sequence of (a) or (b);
(h) nucleotide sequences the sequence of which differs from the sequence of a nucleic acid molecule of (c) due to the degeneracy of the genetic code.

The nucleotide sequence encoding an araD may encode either a prokaryotic or an eukaryotic araD, i.e. an araD with an amino acid sequence that is identical to that of a araD that naturally occurs in the prokaryotic or eukaryotic organism. The present inventors have found that the ability of a particular araD to confer to a eukaryotic host cell the ability to use arabinose and/or to convert arabinose into L-ribulose, and/or xylulose 5-phosphate and/or into a desired fermentation product when co-expressed with araA and araB does not depend so much on whether the araD is of prokaryotic or eukaryotic origin. Rather this depends on the relatedness of the araD's amino acid sequence to that of the sequence SEQ ID NO. 5.

Surprisingly, the codon bias index indicated that expression of the *Lactobacillus plantarum* araA, araB and araD genes were more favorable for expression in yeast than the prokaryolic araA, araB and araD genes described in EP 1 499 708.

It is to be noted that *L. plantarum* is a Generally Regarded As Safe (GRAS) organism, which is recognized as safe by food registration authorities. Therefore, a preferred nucleotide sequence encodes an araA, araB or araD respectively having an amino acid sequence that is related to the sequences SEQ ID NO: 1, 3, or 5 respectively as defined above. A preferred nucleotide sequence encodes a fungal araA, araB or araD respectively (e.g. from a Basidiomycete), more preferably an araA, araB or araD respectively from an anaerobic fungus, e.g. an anaerobic fungus that belongs to the families Neocallimastix, Caecomyces, Piromyces, Orpinomyces, or Ruminomyces. Alternatively, a preferred nucleotide sequence encodes a bacterial araA, araB or araD respectively, preferably from a Gram-positive bacterium, more preferably from the genus *Lactobacillus*, most preferably from *Lactobacillus plantarum* species. Preferably, one, two or three or the araA, araB and araD nucleotide sequences originate from a *Lactobacillus* genus, more preferably a *Lactobacillus plantarum* species. The bacterial araA expressed in the cell of the invention is not the *Bacillus subtilis* araA disclosed in EP 1 499 708 and given as SEQ ID NO:9. SEQ ID NO:10 represents the nucleotide acid sequence coding for SEQ ID NO:9. The bacterial araB and araD expressed in the cell of the invention are not the ones of *Escherichia coli* (*E. coli*) as disclosed in EP 1 499 708 and given as SEQ ID NO: 11 and SEQ ID NO:13. SEQ ID NO: 12 represents the nucleotide acid sequence coding for SEQ ID NO:11. SEQ ID NO:14 represents the nucleotide acid sequence coding for SEQ ID NO:13.

To increase the likelihood that the (bacterial) araA, araB and araD enzymes respectively are expressed in active form in a eukaryotic host cell of the invention such as yeast, the corresponding encoding nucleotide sequence may be adapted to optimise its codon usage to that of the chosen eukaryotic host cell. The adaptiveness of a nucleotide sequence encoding the araA, araB, and araD enzymes (or other enzymes of the invention, see below) to the codon usage of the chosen host cell may be expressed as codon adaptation index (CAI). The codon adaptation index is herein defined as a measurement of the relative adaptiveness of the codon usage of a gene towards the codon usage of highly expressed genes. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8): 2242-51). An adapted nucleotide sequence preferably has a CAI of at least 0.2, 0.3, 0.4, 0.5, 0.6 or 0.7.

In a preferred embodiment, expression of the nucleotide sequences encoding an ara A, an ara B and an ara D as defined earlier herein confers to the cell the ability to use L-arabinose and/or to convert it into L-ribulose, and/or xylulose 5-phosphate. Without wishing to be bound by any theory, L-arabinose is expected to be first converted into L-ribulose, which is subsequently converted into xylulose 5-phosphate which is the main molecule entering the pentose phosphate pathway. In the context of the invention, "using L-arabinose" preferably means that the optical density measured at 660 nm ($OD_{660}$) of transformed cells cultured under aerobic or anaerobic conditions in the presence of at least 0.5% L-arabinose during at least 20 days is increased from approximately 0.5 till 1.0 or more. More preferably, the $OD_{660}$ is increased from 0.5 till 1.5 or more. More preferably, the cells are cultured in the presence of at least 1%, at least 1.5%, at least 2% L-arabinose. Most preferably, the cells are cultured in the presence of approximately 2% L-arabinose.

In the context of the invention, a cell is able "to convert L-arabinose into L-ribulose" when detectable amounts of L-ribulose are detected in cells cultured under aerobic or anaerobic conditions in the presence of L-arabinose (same preferred concentrations as in previous paragraph) during at least 20 days using a suitable assay. Preferably the assay is HPLC for L-ribulose.

In the context of the invention, a cell is able "to convert L-arabinose into xylulose 5-phosphate" when an increase of at least 2% of xylulose 5-phosphate is detected in cells cultured under aerobic or anaerobic conditions in the presence of L-arabinose (same preferred concentrations as in previous paragraph) during at least 20 days using a suitable assay. Preferably, an HPCL-based assay for xylulose 5-phosphate has been described in Zaldivar J., et al ((2002), Appl. Microbiol. Biotechnol., 59:436-442). This assay is briefly described in the experimental part. More preferably, the increase is of at least 5%, 10%, 15%, 20%, 25% or more.

In another preferred embodiment, expression of the nucleotide sequences encoding an ara A, ara B and ara D as defined earlier herein confers to the cell the ability to convert L-arabinose into a desired fermentation product when cultured under aerobic or anaerobic conditions in the presence of L-arabinose (same preferred concentrations as in previous paragraph) during at least one month till one year. More preferably, a cell is able to convert L-arabinose into a desired fermentation product when detectable amounts of a desired fermentation product are detected using a suitable assay and when the cells are cultured under the conditions given in previous sentence. Even more preferably, the assay is HPLC. Even more preferably, the fermentation product is ethanol.

A cell for transformation with the nucleotide sequences encoding the araA, araB, and araD enzymes respectively as described above, preferably is a host cell capable of active or passive xylose transport into and xylose isomerisation within the cell. The cell preferably is capable of active glycolysis. The cell may further contain an endogenous pentose phosphate pathway and may contain endogenous xylulose kinase activity so that xylulose isomerised from xylose may be metabolised to pyruvate. The cell further preferably contains enzymes for conversion of pyruvate to a desired fermentation product such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic or a cephalosporin. The cell may be made capable of producing butanol by introduction of one or more genes of the butanol pathway as disclosed in WO2007/041269.

A preferred cell is naturally capable of alcoholic fermentation, preferably, anaerobic alcoholic fermentation. The host cell further preferably has a high tolerance to ethanol, a high tolerance to low pH (i.e. capable of growth at a pH lower than 5, 4, 3, or 2,5) and towards organic acids like lactic acid, acetic acid or formic acid and sugar degradation products such as furfural and hydroxy-methylfurfural, and a high tolerance to elevated temperatures. Any of these characteristics or activities of the host cell may be naturally present in the host cell or may be introduced or modified through genetic selection or by genetic modification. A suitable host cell is a eukaryotic microorganism like e.g. a fungus, however, most suitable as host cell are yeasts or filamentous fungi.

Yeasts are herein defined as eukaryotic microorganisms and include all species of the subdivision Eumycotina (Alexopoulos, C. J., 1962, In: Introductory Mycology, John Wiley & Sons, Inc., New York) that predominantly grow in unicellular form. Yeasts may either grow by budding of a unicellular thallus or may grow by fission of the organism. Preferred yeasts as host cells belong to one of the genera *Saccharomyces, Kluyveromyces, Candida, Pichia, Schizosaccharomyces, Hansenula, Kloeckera, Schwanniomyces*, or *Yarrowia*. Preferably the yeast is capable of anaerobic fermentation, more preferably anaerobic alcoholic fermentation.

Filamentous fungi are herein defined as eukaryotic microorganisms that include all filamentous forms of the subdivision Eumycotina. These fungi are characterized by a vegetative mycelium composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism of most filamentous fungi is obligately aerobic. Preferred filamentous fungi as host cells belong to one of the genera *Aspergillus, Trichoderma, Humicola, Acremonium, Fusarium*, or *Penicillium*.

Over the years suggestions have been made for the introduction of various organisms for the production of bio-ethanol from crop sugars. In practice, however, all major bio-ethanol production processes have continued to use the yeasts of the genus *Saccharomyces* as ethanol producer. This is due to the many attractive features of *Saccharomyces* species for industrial processes, i.e., a high acid-, ethanol- and osmotolerance, capability of anaerobic growth, and of course its high alcoholic fermentative capacity. Preferred yeast species as host cells include *S. cerevisiae, S. bulderi, S. barnetti, S. exiguus, S. uvarum, S. diastaticus, K. lactis, K. marxianus, K. fragilis*.

In a preferred embodiment, the host cell of the invention is a host cell that has been transformed with a nucleic acid construct comprising the nucleotide sequence encoding the araA, araB, and araD enzymes as defined above. In one more preferred embodiment, the host cell is co-transformed with three nucleic acid constructs, each nucleic acid construct comprising the nucleotide sequence encoding araA, araB or araD. The nucleic acid construct comprising the araA, araB, and/or araD coding sequence is capable of expression of the araA, araB, and/or araD enzymes in the host cell. To this end the nucleic acid construct may be constructed as described in e.g. WO 03/0624430. The host cell may comprise a single but preferably comprises multiple copies of each nucleic acid construct. The nucleic acid construct may be maintained episomally and thus comprise a sequence for autonomous replication, such as an ARS sequence. Suitable episomal nucleic acid constructs may e.g. be based on the yeast 2μ or pKD1 (Fleer et al., 1991, Biotechnology 9:968-975) plasmids. Preferably, however, each nucleic acid construct is integrated in one or more copies into the genome of the host cell. Integration into the host cell's genome may occur at random by illegitimate recombination but preferably nucleic acid construct is integrated into the host cell's genome by homologous recombination as is well known in the art of fungal molecular genetics (see e.g. WO 90/14423, EP-A-0 481 008, EP-A-0 635 574 and U.S. Pat. No. 6,265,186). Accordingly, in a more preferred embodiment, the cell of the invention comprises a nucleic acid construct comprising the araA, araB, and/or araD coding sequence and is capable of expression of the araA, araB, and/or araD enzymes. In an even more preferred embodiment, the araA, araB, and/or araD coding sequences are each operably linked to a promoter that causes sufficient expression of the corresponding nucleotide sequences in a cell to confer to the cell the ability to use L-arabinose, and/or to convert L-arabinose into L-ribulose, and/or xylulose 5-phosphate. Preferably the cell is a yeast cell. Accordingly, in a further aspect, the invention also encompasses a nucleic acid construct as earlier outlined herein. Preferably, a nucleic acid construct comprises a nucleic acid sequence encoding an araA, araB and/or araD. Nucleic acid sequences encoding an araA, araB, or araD have been all earlier defined herein. Even more preferably, the expression of the corresponding nucleotide sequences in a cell confer to the cell the ability to convert L-arabinose into a desired fermentation product as defined later herein. In an even more preferred embodiment, the fermentation product is ethanol. Even more preferably, the cell is a yeast cell.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

The promoter that could be used to achieve the expression of the nucleotide sequences coding for araA, araB and/or araD may be not native to the nucleotide sequence coding for the enzyme to be expressed, i.e. a promoter that is heterologous to the nucleotide sequence (coding sequence) to which it is operably linked. Although the promoter preferably is heterologous to the coding sequence to which it is operably linked, it is also preferred that the promoter is homologous, i.e. endogenous to the host cell. Preferably the heterologous promoter (to the nucleotide sequence) is capable of producing a higher steady state level of the transcript comprising the coding sequence (or is capable of producing more transcript molecules, i.e. mRNA molecules, per unit of time) than is the promoter that is native to the coding sequence, preferably under conditions where arabinose, or arabinose and glucose, or xylose and arabinose or xylose and arabinose and glucose are available as carbon sources, more preferably as major carbon sources (i.e. more than 50% of the available carbon source consists of arabinose, or arabinose and glucose, or xylose and arabinose or xylose and arabinose and glucose), most preferably as sole carbon sources. Suitable promoters in this context include both constitutive and inducible natural promoters as well as engineered promoters. A preferred promoter for use in the present invention will in addition be insensitive to catabolite (glucose) repression and/or will preferably not require arabinose and/or xylose for induction.

Promotors having these characteristics are widely available and known to the skilled person. Suitable examples of such promoters include e.g. promoters from glycolytic genes, such as the phosphofructokinase (PPK), triose phosphate isomerase (TPI), glyceraldehyde-3-phosphate dehydrogenase (GPD, TDH3 or GAPDH), pyruvate kinase (PYK), phosphoglycerate kinase (PGK) promoters from yeasts or filamentous fungi; more details about such promoters from yeast may be found in (WO 93/03159). Other useful promoters are ribosomal protein encoding gene promoters, the lactase gene promoter (LAC4), alcohol dehydrogenase promoters (ADH1, ADH4, and the like), the enolase promoter (ENO), the glucose-6-phosphate isomerase promoter (PGI1, Hauf et al, 2000) or the hexose(glucose) transporter promoter (HXT7) or the glyceraldehyde-3-phosphate dehydrogenase (TDH3). The sequence of the PGI1 promoter is given in SEQ ID NO:51. The sequence of the HXT7 promoter is given in SEQ ID NO:52. The sequence of the TDH3 promoter is given in SEQ ID NO:49. Other promoters, both constitutive and inducible, and enhancers or upstream activating sequences will be known to those of skill in the art. The promoters used in the host cells of the invention may be modified, if desired, to affect their control characteristics. A preferred cell of the invention is a eukaryotic cell transformed with the araA, araB and araD genes of *L. plantarum*. More preferably, the eukaryotic cell is a yeast cell, even more preferably a *S. cerevisiae* strain transformed with the araA, araB and araD genes of *L. plantarum*. Most preferably, the cell is either CBS120327 or CBS120328 both deposited at the CBS Institute (The Netherlands) on Sep. 27, 2006.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically be operably linked to another promoter sequence or, if applicable, another secretory signal sequence and/or terminator sequence than in its natural environment. When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as earlier presented. Preferably the region of identity is greater than about 5 bp, more preferably the region of identity is greater than 10 bp.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

Preferred Eukaryotic Cell Able to Use and/or Convert L-Arabinose and Xylose

In a more preferred embodiment, the cell of the invention that expresses araA, araB and araD is able to use L-arabinose and/or to convert it into L-ribulose, and/or xylulose 5-phosphate and/or a desired fermentation product as earlier defined herein and additionally exhibits the ability to use xylose and/or convert xylose into xylulose. The conversion of xylose into xylulose is preferably a one step isomerisation step (direct isomerisation of xylose into xylulose). This type of cell is therefore able to use both L-arabinose and xylose. "Using" xylose has preferably the same meaning as "using" L-arabinose as earlier defined herein.

Enzyme definitions are as used in WO 06/009434, for xylose isomerase (EC 5.3.1.5), xylulose kinase (EC 2.7.1.17), ribulose 5-phosphate epimerase (5.1.3.1), ribulose 5-phosphate isomerase (EC 5.3.1.6), transketolase (EC 2.2.1.1), transaldolase (EC 2.2.1.2), and aldose reductase" (EC 1.1.1.21).

In a preferred embodiment, the eukaryotic cell of the invention expressing araA, araB and araD as earlier defined herein has the ability of isomerising xylose to xylulose as e.g. described in WO 03/0624430 or in WO 06/009434. The ability of isomerising xylose to xylulose is conferred to the host cell by transformation of the host cell with a nucleic acid construct comprising a nucleotide sequence encoding a xylose isomerase. The transformed host cell's ability to isomerise xylose into xylulose is the direct isomerisation of xylose to xylulose. This is understood to mean that xylose isomerised into xylulose in a single reaction catalysed by a xylose isomerase, as opposed to the two step conversion of xylose into xylulose via a xylitol intermediate as catalysed by xylose reductase and xylitol dehydrogenase, respectively.

The nucleotide sequence encodes a xylose isomerase that is preferably expressed in active form in the transformed host cell of the invention. Thus, expression of the nucleotide sequence in the host cell produces a xylose isomerase with a specific activity of at least 10 U xylose isomerase activity per mg protein at 30° C., preferably at least 20, 25, 30, 50, 100, 200, 300 or 500 Upper mg at 30° C. The specific activity of the xylose isomerase expressed in the transformed host cell is herein defined as the amount of xylose isomerase activity units per mg protein of cell free lysate of the host cell, e.g. a yeast cell free lysate. Determination of the xylose isomerase activity has already been described earlier herein.

Preferably, expression of the nucleotide sequence encoding the xylose isomerase in the host cell produces a xylose isomerase with a $K_m$ for xylose that is less than 50, 40, 30 or 25 mM, more preferably, the $K_m$ for xylose is about 20 mM or less.

A preferred nucleotide sequence encoding the xylose isomerase may be selected from the group consisting of:
(e) nucleotide sequences encoding a polypeptide comprising an amino acid sequence that has at least 60, 65, 70, 75, 80, 85, 90, 95, 97, 98, or 99% sequence identity with the amino acid sequence of SEQ ID NO. 7 or SEQ ID NO:15;
(f) nucleotide sequences comprising a nucleotide sequence that has at least 40, 50, 60, 70, 80, 90, 95, 97, 98, or 99% sequence identity with the nucleotide sequence of SEQ ID NO. 8 or SEQ ID NO:16;
(g) nucleotide sequences the complementary strand of which hybridises to a nucleic acid molecule sequence of (a) or (b);
(h) nucleotide sequences the sequence of which differs from the sequence of a nucleic acid molecule of (c) due to the degeneracy of the genetic code.

The nucleotide sequence encoding the xylose isomerase may encode either a prokaryotic or an eukaryotic xylose isomerase, i.e. a xylose isomerase with an amino acid sequence that is identical to that of a xylose isomerase that naturally occurs in the prokaryotic or eukaryotic organism. The present inventors have found that the ability of a particular xylose isomerase to confer to a eukaryotic host cell the ability to isomerise xylose into xylulose does not depend so much on whether the isomerase is of prokaryotic or eukaryotic origin. Rather this depends on the relatedness of the isomerase's amino acid sequence to that of the Piromyces sequence (SEQ ID NO. 7). Surprisingly, the eukaryotic Piromyces isomerase is more related to prokaryotic isomerases than to other known eukaryotic isomerases. Therefore, a preferred nucleotide sequence encodes a xylose isomerase having an amino acid sequence that is related to the Piromyces sequence as defined above. A preferred nucleotide sequence encodes a fungal xylose isomerase (e.g. from a Basidiomycete), more preferably a xylose isomerase from an anaerobic fungus, e.g. a xylose isomerase from an anaerobic fungus that belongs to the families Neocallimastix, Caecomyces, Piromyces, Orpinomyces, or Ruminomyces. Alternatively, a preferred nucleotide sequence encodes a bacterial xylose isomerase, preferably a Gram-negative bacterium, more preferably an isomerase from the class *Bacteroides*, or from the genus *Bacteroides*, most preferably from *B. thetaiotaomicron* (SEQ ID NO. 15).

To increase the likelihood that the xylose isomerase is expressed in active form in a eukaryotic host cell such as yeast, the nucleotide sequence encoding the xylose isomerase may be adapted to optimise its codon usage to that of the eukaryotic host cell as earlier defined herein.

A host cell for transformation with the nucleotide sequence encoding the xylose isomerase as described above, preferably is a host capable of active or passive xylose transport into the cell. The host cell preferably contains active glycolysis. The host cell may further contain an endogenous pentose phosphate pathway and may contain endogenous xylulose kinase activity so that xylulose isomerised from xylose may be metabolised to pyruvate. The host further preferably contains enzymes for conversion of pyruvate to a desired fermentation product such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic or a cephalosporin. A preferred host cell is a host cell that is naturally capable of alcoholic fermentation, preferably, anaerobic alcoholic fermentation. The host cell further preferably has a high tolerance to ethanol, a high tolerance to low pH (i.e. capable of growth at a pH lower than 5, 4, 3, or 2,5) and towards organic acids like lactic acid, acetic acid or formic acid and sugar degradation products such as furfural and hydroxy-methylfurfural, and a high tolerance to elevated temperatures. Any of these characteristics or activities of the host cell may be naturally present in the host cell or may be introduced or modified by genetic modification. A suitable cell is a eukaryotic microorganism like e.g. a fungus, however, most suitable as host cell are yeasts or filamentous fungi. Preferred yeasts and filamentous fungi have already been defined herein.

As used herein the wording host cell has the same meaning as cell.

The cell of the invention is preferably transformed with a nucleic acid construct comprising the nucleotide sequence encoding the xylose isomerase. The nucleic acid construct that is preferably used is the same as the one used comprising the nucleotide sequence encoding araA, araB or araD.

In another preferred embodiment of the invention, the cell of the invention:
expressing araA, araB and araD, and exhibiting the ability to directly isomerise xylose into xylulose, as earlier defined herein further comprises a genetic modification that increases the flux of the pentose phosphate pathway, as described in WO 06/009434. In particular, the genetic modification causes an increased flux of the non-oxidative part pentose phosphate pathway. A genetic modification that causes an increased flux of the non-oxidative part of the pentose phosphate pathway is herein understood to mean a modification that increases the flux by at least a factor 1.1, 1.2, 1.5, 2, 5, 10 or 20 as compared to the flux in a strain which is genetically identical except for the genetic modification causing the increased flux. The flux of the non-oxidative part of the pentose phosphate pathway may be measured by growing the modified host on xylose as sole carbon source, determining the specific xylose consumption rate and substracting the specific xylitol production rate from the specific xylose consumption rate, if any xylitol is produced. However, the flux of the non-oxidative part of the pentose phosphate pathway is proportional with the growth rate on xylose as sole carbon source, preferably with the anaerobic growth rate on xylose as sole carbon source. There is a linear relation between the growth rate on xylose as sole carbon source ($\mu_{max}$) and the flux of the non-oxidative part of the pentose phosphate pathway. The specific xylose consumption rate ($Q_s$) is equal to the growth rate ($\mu$) divided by the yield of biomass on sugar ($Y_{xs}$) because the yield of biomass on sugar is constant (under a given set of conditions: anaerobic, growth medium, pH, genetic background of the strain, etc.; i.e. $Q_s = \mu/Y_{xs}$). Therefore the increased flux of the non-oxidative part of the pentose phosphate pathway may be deduced from the increase in maximum growth rate under these conditions. In a preferred embodiment, the cell comprises a genetic modification that increases the flux of the pentose phosphate pathway and has a specific xylose consumption rate of at least 346 mg xylose/g biomass/h.

Genetic modifications that increase the flux of the pentose phosphate pathway may be introduced in the host cell in various ways. These including e.g. achieving higher steady state activity levels of xylulose kinase and/or one or more of the enzymes of the non-oxidative part pentose phosphate pathway and/or a reduced steady state level of unspecific aldose reductase activity. These changes in steady state activity levels may be effected by selection of mutants (spontaneous or induced by chemicals or radiation) and/or by recombinant DNA technology e.g. by overexpression or inactivation, respectively, of genes encoding the enzymes or factors regulating these genes.

In a more preferred host cell, the genetic modification comprises overexpression of at least one enzyme of the (non-oxidative part) pentose phosphate pathway. Preferably the enzyme is selected from the group consisting of the enzymes encoding for ribulose-5-phosphate isomerase, ribulose-5-phosphate epimerase, transketolase and transaldolase, as described in WO 06/009434.

Various combinations of enzymes of the (non-oxidative part) pentose phosphate pathway may be overexpressed. E.g. the enzymes that are overexpressed may be at least the enzymes ribulose-5-phosphate isomerase and ribulose-5-phosphate epimerase; or at least the enzymes ribulose-5-phosphate isomerase and transketolase; or at least the enzymes ribulose-5-phosphate isomerase and transaldolase; or at least the enzymes ribulose-5-phosphate epimerase and transketolase; or at least the enzymes ribulose-5-phosphate epimerase and transaldolase; or at least the enzymes transketolase and transaldolase; or at least the enzymes ribulose-5-phosphate epimerase, transketolase and transaldolase; or at least the enzymes ribulose-5-phosphate isomerase, transketolase and transaldolase; or at least the enzymes ribulose-5-phosphate isomerase, ribulose-5-phosphate epimerase, and transaldolase; or at least the enzymes ribulose-5-phosphate isomerase, ribulose-5-phosphate epimerase, and transketolase. In one embodiment of the invention each of the enzymes ribulose-5-phosphate isomerase, ribulose-5-phosphate epimerase, transketolase and transaldolase are overexpressed in the host cell. More preferred is a host cell in which the genetic modification comprises at least overexpression of both the enzymes transketolase and transaldolase as such a host cell is already capable of anaerobic growth on xylose. In fact, under some conditions we have found that host cells overexpressing only the transketolase and the transaldolase already have the same anaerobic growth rate on xylose as do host cells that overexpress all four of the enzymes, i.e. the ribulose-5-phosphate isomerase, ribulose-5-phosphate epimerase, transketolase and transaldolase. Moreover, host cells overexpressing both of the enzymes ribulose-5-phosphate isomerase and ribulose-5-phosphate epimerase are preferred over host cells overexpressing only the isomerase or only the epimerase as overexpression of only one of these enzymes may produce metabolic imbalances.

There are various means available in the art for overexpression of enzymes in the cells of the invention. In particular, an enzyme may be overexpressed by increasing the copy number of the gene coding for the enzyme in the host cell, e.g. by integrating additional copies of the gene in the host cell's genome, by expressing the gene from an episomal multicopy expression vector or by introducing a episomal expression vector that comprises multiple copies of the gene.

Alternatively overexpression of enzymes in the host cells of the invention may be achieved by using a promoter that is not native to the sequence coding for the enzyme to be overexpressed, i.e. a promoter that is heterologous to the coding sequence to which it is operably linked. Suitable promoters to this end have already been defined herein.

The coding sequence used for overexpression of the enzymes preferably is homologous to the host cell of the invention. However, coding sequences that are heterologous to the host cell of the invention may likewise be applied, as mentioned in WO 06/009434.

A nucleotide sequence used for overexpression of ribulose-5-phosphate isomerase in the host cell of the invention is a nucleotide sequence encoding a polypeptide with ribulose-5-phosphate isomerase activity, whereby preferably the polypeptide has an amino acid sequence having at least 50, 60, 70, 80, 90 or 95% identity with SEQ ID NO. 17 or whereby the nucleotide sequence is capable of hybridising with the nucleotide sequence of SEQ ID NO. 18, under moderate conditions, preferably under stringent conditions.

A nucleotide sequence used for overexpression of ribulose-5-phosphate epimerase in the host cell of the invention is a nucleotide sequence encoding a polypeptide with ribulose-5-phosphate epimerase activity, whereby preferably the polypeptide has an amino acid sequence having at least 50, 60, 70, 80, 90 or 95% identity with SEQ ID NO. 19 or whereby the nucleotide sequence is capable of hybridising with the nucleotide sequence of SEQ ID NO. 20, under moderate conditions, preferably under stringent conditions.

A nucleotide sequence used for overexpression of transketolase in the host cell of the invention is a nucleotide sequence encoding a polypeptide with transketolase activity, whereby preferably the polypeptide has an amino acid sequence having at least 50, 60, 70, 80, 90 or 95% identity with SEQ ID NO. 21 or whereby the nucleotide sequence is capable of hybridising with the nucleotide sequence of SEQ ID NO. 22, under moderate conditions, preferably under stringent conditions.

A nucleotide sequence used for overexpression of transaldolase in the host cell of the invention is a nucleotide sequence encoding a polypeptide with transaldolase activity, whereby preferably the polypeptide has an amino acid sequence having at least 50, 60, 70, 80, 90 or 95% identity with SEQ ID NO. 23 or whereby the nucleotide sequence is capable of hybridising with the nucleotide sequence of SEQ ID NO. 24, under moderate conditions, preferably under stringent conditions.

Overexpression of an enzyme, when referring to the production of the enzyme in a genetically modified host cell, means that the enzyme is produced at a higher level of specific enzymatic activity as compared to the unmodified host cell under identical conditions. Usually this means that the enzymatically active protein (or proteins in case of multi-subunit enzymes) is produced in greater amounts, or rather at a higher steady state level as compared to the unmodified host cell under identical conditions. Similarly this usually means that the mRNA coding for the enzymatically active protein is produced in greater amounts, or again rather at a higher steady state level as compared to the unmodified host cell under identical conditions. Overexpression of an enzyme is thus preferably determined by measuring the level of the enzyme's specific activity in the host cell using appropriate enzyme assays as described herein. Alternatively, overexpression of the enzyme may determined indirectly by quantifying the specific steady state level of enzyme protein, e.g. using antibodies specific for the enzyme, or by quantifying the specific steady level of the mRNA coding for the enzyme. The latter may particularly be suitable for enzymes of the pentose phosphate pathway for which enzymatic assays are not easily feasible as substrates for the enzymes are not commercially available. Preferably in the host cells of the invention, an enzyme to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

In a further preferred embodiment, the host cell of the invention:
  expressing araA, araB and araD, and exhibiting the ability to directly isomerise xylose into xyluose, and optionally
  comprising a genetic modification that increase the flux of the pentose pathway as earlier defined herein
further comprises a genetic modification that increases the specific xylulose kinase activity. Preferably the genetic modification causes overexpression of a xylulose kinase, e.g. by overexpression of a nucleotide sequence encoding a xylulose kinase. The gene encoding the xylulose kinase may be endogenous to the host cell or may be a xylulose kinase that is heterologous to the host cell. A nucleotide sequence used for overexpression of xylulose kinase in the host cell of the invention is a nucleotide sequence encoding a polypeptide with xylulose kinase activity, whereby preferably the polypeptide has an amino acid sequence having at least 50, 60, 70, 80, 90 or 95% identity with SEQ ID NO. 25 or whereby the nucleotide sequence is capable of hybridising with the nucleotide sequence of SEQ ID NO. 26, under moderate conditions, preferably under stringent conditions.

A particularly preferred xylulose kinase is a xylose kinase that is related to the xylulose kinase xylB from *Piromyces* as mentioned in WO 03/0624430. A more preferred nucleotide sequence for use in overexpression of xylulose kinase in the host cell of the invention is a nucleotide sequence encoding a polypeptide with xylulose kinase activity, whereby preferably the polypeptide has an amino acid sequence having at least 45, 50, 55, 60, 65, 70, 80, 90 or 95% identity with SEQ ID NO. 27 or whereby the nucleotide sequence is capable of hybridising with the nucleotide sequence of SEQ ID NO. 28, under moderate conditions, preferably under stringent conditions.

In the host cells of the invention, genetic modification that increases the specific xylulose kinase activity may be combined with any of the modifications increasing the flux of the pentose phosphate pathway as described above, but this combination is not essential for the invention. Thus, a host cell of the invention comprising a genetic modification that increases the specific xylulose kinase activity in addition to the expression of the araA, araB and araD enzymes as defined herein is specifically included in the invention. The various means available in the art for achieving and analysing overexpression of a xylulose kinase in the host cells of the invention are the same as described above for enzymes of the pentose phosphate pathway. Preferably in the host cells of the invention, a xylulose kinase to be overexpressed is overexpressed by at least a factor 1.1, 1.2, 1.5, 2, 5, 10 or 20 as compared to a strain which is genetically identical except for the genetic modification causing the overexpression. It is to be understood that these levels of overexpression may apply to the steady state level of the enzyme's activity, the steady state level of the enzyme's protein as well as to the steady state level of the transcript coding for the enzyme.

In a further preferred embodiment, the host cell of the invention:
  expressing araA, araB and araD, and exhibiting the ability to directly isomerise xylose into xylulose, and optionally
  comprising a genetic modification that increase the flux of the pentose pathway and/or
  further comprising a genetic modification that increases the specific xylulose kinase activity all as earlier defined herein
further comprises a genetic modification that reduces unspecific aldose reductase activity in the host cell. Preferably, unspecific aldose reductase activity is reduced in the host cell by one or more genetic modifications that reduce the expression of or inactivate a gene encoding an unspecific aldose reductase, as described in WO 06/009434. Preferably, the genetic modifications reduce or inactivate the expression of each endogenous copy of a gene encoding an unspecific aldose reductase in the host cell. Host cells may comprise multiple copies of genes encoding unspecific aldose reductases as a result of di-, poly- or aneu-ploidy, and/or the host cell may contain several different (iso)enzymes with aldose reductase activity that differ in amino acid sequence and that are each encoded by a different gene. Also in such instances preferably the expression of each gene that encodes an unspecific aldose reductase is reduced or inactivated. Preferably, the gene is inactivated by deletion of at least part of the gene or by disruption of the gene, whereby in this context the term gene also includes any non-coding sequence up- or downstream of the coding sequence, the (partial) deletion or inactivation of which results in a reduction of expression of unspecific aldose reductase activity in the host cell. A nucleotide sequence encoding an aldose reductase whose activity is to be reduced in the host cell of the invention is a nucleotide sequence encoding a polypeptide with aldose reductase activity, whereby preferably the polypeptide has an amino acid sequence having at least 50, 60, 70, 80, 90 or 95% identity with SEQ ID NO. 29 or whereby the nucleotide sequence is capable of hybridising with the nucleotide sequence of SEQ ID NO. 30 under moderate conditions, preferably under stringent conditions.

In the host cells of the invention, the expression of the araA, araB and araD enzymes as defined herein is combined with genetic modification that reduces unspecific aldose reductase activity. The genetic modification leading to the reduction of unspecific aldose reductase activity may be combined with any of the modifications increasing the flux of the pentose phosphate pathway and/or with any of the modifications increasing the specific xylulose kinase activity in the host cells as described above, but these combinations are not essential for the invention. Thus, a host cell expressing araA, araB, and araD, comprising an additional genetic modification that reduces unspecific aldose reductase activity is specifically included in the invention.

In a preferred embodiment, the host cell is CBS120327 deposited at the CBS Institute (The Netherlands) on Sep. 27, 2006.

In a further preferred embodiment, the invention relates to modified host cells that are further adapted to L-arabinose (use L-arabinose and/or convert it into L-ribulose, and/or xylulose 5-phosphate and/or into a desired fermentation product and optionally xylose utilisation by selection of mutants, either spontaneous or induced (e.g. by radiation or chemicals), for growth on L-arabinose and optionally xylose, preferably on L-arabinose and optionally xylose as sole carbon source, and more preferably under anaerobic conditions. Selection of mutants may be performed by serial passaging of cultures as e.g. described by Kuyper et al. (2004, FEMS Yeast Res. 4: 655-664) and/or by cultivation under selective pressure in a chemostat culture as is described in Example 4 of WO 06/009434. This selection process may be continued as long as necessary. This selection process is preferably carried out during one week till one year. However, the selection process may be carried out for a longer period of time if necessary. During the selection process, the cells are preferably cultured in the presence of approximately 20 g/l L-arabinose and/or approximately 20 g/l xylose. The cell obtained at the end of this selection process is expected to be improved as to its capacities of using L-arabinose and/or xylose, and/or converting L-arabinose into L-ribulose and/or xylulose 5-phosphate and/or a desired fermentation product such as ethanol. In this context "improved cell" may mean that the obtained cell is able to use L-arabinose and/or xylose in a more efficient way than the cell it derives from. For example, the obtained cell is expected to better grow: increase of the specific growth rate of at least 2% than the cell it derives from under the same conditions. Preferably, the increase is of at least 4%, 6%, 8%, 10%, 15%, 20%, 25% or more. The specific growth rate may be calculated from $OD_{660}$ as known to the skilled person. Therefore, by monitoring the $OD_{660}$, one can deduce the specific growth rate. In this context "improved cell" may also mean that the obtained cell converts L-arabinose into L-ribulose and/or xylulose 5-phosphate and/or a desired fermentation product such as ethanol in a more efficient way than the cell it derives from. For example, the obtained cell is expected to produce higher amounts of L-ribulose and/or xylulose 5-phosphate and/or a desired fermentation product such as ethanol: increase of at least one of these compounds of at least 2% than the cell it derives from under the same conditions. Preferably, the increase is of at least 4%, 6%, 8%, 10%, 15%, 20%, 25% or more. In this context "improved cell" may also mean that the obtained cell converts xylose into xylulose and/or a desired fermentation product such as ethanol in a more efficient way than the cell it derives from. For example, the obtained cell is expected to produce higher amounts of xylulose and/or a desired fermentation product such as ethanol: increase of at least one of these compounds of at least 2% than the cell it derives from under the same conditions. Preferably, the increase is of at least 4%, 6%, 8%, 10%, 15%, 20%, 25% or more.

In a preferred host cell of the invention at least one of the genetic modifications described above, including modifications obtained by selection of mutants, confer to the host cell the ability to grow on L-arabinose and optionally xylose as carbon source, preferably as sole carbon source, and preferably under anaerobic conditions. Preferably the modified host cell produce essentially no xylitol, e.g. the xylitol produced is below the detection limit or e.g. less than 5, 2, 1, 0.5, or 0.3% of the carbon consumed on a molar basis.

Preferably the modified host cell has the ability to grow on L-arabinose and optionally xylose as sole carbon source at a rate of at least 0.001, 0.005, 0.01, 0.03, 0.05, 0.1, 0.2, 0.25 or 0.3 $h^{-1}$ under aerobic conditions, or, if applicable, at a rate of at least 0.001, 0.005, 0.01, 0.03, 0.05, 0.07, 0.08, 0.09, 0.1, 0.12, 0.15 or 0.2 $h^{-1}$ under anaerobic conditions Preferably the modified host cell has the ability to grow on a mixture of glucose and L-arabinose and optionally xylose (in a 1:1 weight ratio) as sole carbon source at a rate of at least 0.001, 0.005, 0.01, 0.03, 0.05, 0.1, 0.2, 0.25 or 0.3 $h^{-1}$ under aerobic conditions, or, if applicable, at a rate of at least 0.001, 0.005, 0.01, 0.03, 0.05, 0.1, 0.12, 0.15, or 0.2 $h^{-1}$ under anaerobic conditions.

Preferably, the modified host cell has a specific L-arabinose and optionally xylose consumption rate of at least 346, 350, 400, 500, 600, 650, 700, 750, 800, 900 or 1000 mg/g cells/h. Preferably, the modified host cell has a yield of fermentation product (such as ethanol) on L-arabinose and optionally xylose that is at least 20, 25, 30, 35, 40, 45, 50, 55, 60, 70, 80, 85, 90, 95 or 98% of the host cell's yield of fermentation product (such as ethanol) on glucose. More preferably, the modified host cell's yield of fermentation product (such as ethanol) on L-arabinose and optionally xylose is equal to the host cell's yield of fermentation product (such as ethanol) on glucose. Likewise, the modified host cell's biomass yield on L-arabinose and optionally xylose is preferably at least 55, 60, 70, 80, 85, 90, 95 or 98% of the host cell's biomass yield on glucose. More preferably, the modified host cell's biomass yield on L-arabinose and optionally xylose is equal to the host cell's biomass yield on glucose. It is understood that in the comparison of yields on glucose and L-arabinose and optionally xylose both yields are compared under aerobic conditions or both under anaerobic conditions. In a more preferred embodiment, the host cell is CBS120328 deposited at the CBS Institute (The Netherlands) on Sep. 27, 2006 or CBS121879 deposited at the CBS Institute (The Netherlands) on Sep. 20, 2007.

In a preferred embodiment, the cell expresses one or more enzymes that confer to the cell the ability to produce at least one fermentation product selected from the group consisting of ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. In a more preferred embodiment, the host cell of the invention is a host cell for the production of ethanol. In another preferred embodiment, the invention relates to a transformed host cell for the production of fermentation products other than ethanol. Such non-ethanolic fermentation products include in principle any bulk or fine chemical that is producible by a eukaryotic microorganism such as a yeast or a filamentous fungus. Such fermentation products include e.g. lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. A preferred host cell of the invention for production of non-ethanolic fermentation products is a host cell that contains a genetic modification that results in decreased alcohol dehydrogenase activity.

Method

In a further aspect, the invention relates to fermentation processes in which a host cell of the invention is used for the fermentation of a carbon source comprising a source of L-arabinose and optionally a source of xylose. Preferably, the source of L-arabinose and the source of xylose are L-arabinose and xylose. In addition, the carbon source in the fermentation medium may also comprise a source of glucose. The source of L-arabinose, xylose or glucose may be L-arabinose, xylose or glucose as such or may be any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrates (such as xylanases, glucanases, amylases and the like) may be added to the fermentation medium or may be produced by the modified host cell. In the latter case the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

In a preferred process, there is provided a process for producing a fermentation product selected from the group consisting of ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin whereby the process comprises the steps of:

(a) fermenting a medium containing a source of L-arabinose and optionally xylose with a modified host cell as defined herein, whereby the host cell ferments L-arabinose and optionally xylose to the fermentation product, and optionally, (b) recovering the fermentation product.

The fermentation process is a process for the production of a fermentation product such as e.g. ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic, such as Penicillin G or Penicillin V and fermentative derivatives thereof, and/or a cephalosporin. The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotics and a cephalosporin. In a preferred embodiment, the fermentation process is anaerobic. An anaerobic process is advantageous since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions. According to the inventors, the process of the invention is the first anaerobic fermentation process with a medium comprising a source of L-arabinose that has been developed so far.

In another preferred embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably less than 38° C. For yeast or filamentous fungal host cells, the fermentation process is preferably performed at a temperature which is lower than 35, 33, 30 or 28° C. and at a temperature which is higher than 20, 22, or 25° C.

A preferred process is a process for the production of ethanol, whereby the process comprises the steps of: (a) fermenting a medium containing a source of L-arabinose and optionally xylose with a modified host cell as defined herein, whereby the host cell ferments L-arabinose and optionally xylose to ethanol; and optionally, (b) recovery of the ethanol. The fermentation medium may also comprise a source of glucose that is also fermented to ethanol. In a preferred embodiment, the fermentation process for the production of ethanol is anaerobic. Anaerobic has already been defined earlier herein.

In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

In the process, the volumetric ethanol productivity is preferably at least 0.5, 1.0, 1.5, 2.0, 2.5, 3.0, 5.0 or 10.0 g ethanol per liter per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g. ethanol per g. glucose or xylose. In another preferred embodiment, the invention relates to a process for producing a fermentation product selected from the group consisting of lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. The process preferably comprises the steps of (a) fermenting a medium containing a source of L-arabinose and optionally xylose with a modified host cell as defined herein above, whereby the host cell ferments L-arabinose and optionally xylose to the fermentation product, and optionally, (b) recovery of the fermentation product. In a preferred process, the medium also contains a source of glucose.

In the fermentation process of the invention leading to the production of ethanol, several advantages can be cited by comparison to known ethanol fermentations processes:
  anaerobic processes are possible.
  oxygen limited conditions are also possible.
  higher ethanol yields and ethanol production rates can be obtained.
  the strain used may be able to use L-arabinose and optionally xylose.

Alternatively to the fermentation processes described above, another fermentation process is provided as a further aspect of the invention wherein, at least two distinct cells are used for the fermentation of a carbon source comprising at least two sources of carbon selected from the group consisting of but not limited thereto: a source of L-arabinose, a source of xylose and a source of glucose. In this fermentation process, "at least two distinct cells" means this process is preferably a co-fermentation process. In one preferred embodiment, two distinct cells are used: one being the one of the invention as earlier defined able to use L-arabinose, and/or to convert it into L-ribulose, and/or xylulose 5-phosphate and/or into a desired fermentation product such as ethanol and optionally being able to use xylose, the other one being for example a strain which is able to use xylose and/or convert it into a desired fermentation product such as ethanol as defined in WO 03/062430 and/or WO 06/009434. A cell which is able to use xylose is preferably a strain which exhibits the ability of directly isomerising xylose into xylulose (in one step) as earlier defined herein. These two distinct strains are preferably cultivated in the presence of a source of L-arabinose, a source of xylose and optionally a source of glucose. Three distinct cells or more may be co-cultivated and/or three or more sources of carbon may be used, provided at least one cell is able to use at least one source of carbon present and/or to convert it into a desired fermentation product such as ethanol. The expression "use at least one source of carbon" has the same meaning as the expression "use of L-arabinose". The expression "convert it (i.e. a source of carbon) into a desired fermentation product has the same meaning as the expression "convert L-arabinose into a desired fermentation product".

In a preferred embodiment, the invention relates to a process for producing a fermentation product selected from the group consisting of ethanol, lactic acid, 3-hydroxy-propionic acid, acrylic acid, acetic acid, succinic acid, citric acid, malic acid, fumaric acid, amino acids, 1,3-propane-diol, ethylene, glycerol, butanol, β-lactam antibiotics and cephalosporins, whereby the process comprises the steps of:

(a) fermenting a medium containing at least a source of L-arabinose and a source of xylose with a cell of the invention as earlier defined herein and a cell able to use xylose and/or exhibiting the ability to directly isomerise xylose into xylulose, whereby each cell ferments L-arabinose and/or xylose to the fermentation product, and optionally, (b) recovering the fermentation product.

All preferred embodiments of the fermentation processes as described above are also preferred embodiments of this further fermentation processes: identity of the fermentation product, identity of source of L-arabinose and source of xylose, conditions of fermentation (aerobical or anaerobical conditions, oxygen-limited conditions, temperature at which the process is being carried out, productivity of ethanol, yield of ethanol).

Genetic Modifications

For overexpression of enzymes in the host cells of the inventions as described above, as well as for additional genetic modification of host cells, preferably yeasts, host cells are transformed with the various nucleic acid constructs of the invention by methods well known in the art. Such methods are e.g. known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

Promoters for use in the nucleic acid constructs for overexpression of enzymes in the host cells of the invention have been described above. In the nucleic acid constructs for overexpression, the 3'-end of the nucleotide acid sequence encoding the enzyme(s) preferably is operably linked to a transcription terminator sequence. Preferably the terminator sequence is operable in a host cell of choice, such as e.g. the yeast species of choice. In any case the choice of the terminator is not critical; it may e.g. be from any yeast gene, although terminators may sometimes work if from a non-yeast, eukaryotic, gene. The transcription termination sequence further preferably comprises a polyadenylation signal. Preferred terminator sequences are the alcohol dehydrogenase (ADH1) and the PGI1 terminators. More preferably, the ADH1 and the PGI1 terminators are both from S. cerevisiae (SEQ ID NO:50 and SEQ ID NO:53 respectively).

Optionally, a selectable marker may be present in the nucleic acid construct. As used herein, the term "marker" refers to a gene encoding a trait or a phenotype which permits the selection of, or the screening for, a host cell containing the marker. The marker gene may be an antibiotic resistance gene whereby the appropriate antibiotic can be used to select for transformed cells from among cells that are not transformed. Preferably however, non-antibiotic resistance markers are used, such as auxotrophic markers (URA3, TRP1, LEU2). In a preferred embodiment the host cells transformed with the nucleic acid constructs are marker gene free. Methods for constructing recombinant marker gene free microbial host cells are disclosed in EP-A-0 635 574 and are based on the use of bidirectional markers. Alternatively, a screenable marker such as Green Fluorescent Protein, lacZ, luciferase, chloramphenicol acetyltransferase, beta-glucuronidase may be incorporated into the nucleic acid constructs of the invention allowing to screen for transformed cells.

Optional further elements that may be present in the nucleic acid constructs of the invention include, but are not limited to, one or more leader sequences, enhancers, integration factors, and/or reporter genes, intron sequences, centromers, telomers and/or matrix attachment (MAR) sequences. The nucleic acid constructs of the invention may further comprise a sequence for autonomous replication, such as an ARS sequence. Suitable episomal nucleic acid constructs may e.g. be based on the yeast 2μ or pKD1 (Fleer et al., 1991, Biotechnology 9:968-975) plasmids. Alternatively the nucleic acid construct may comprise sequences for integration, preferably by homologous recombination. Such sequences may thus be sequences homologous to the target site for integration in the host cell's genome. The nucleic acid constructs of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual ($3^{rd}$ edition), Cold Spring Harbor Laboratory, Cold Spring Harbor Laboratory Press.

Methods for inactivation and gene disruption in yeast or fungi are well known in the art (see e.g. Fincham, 1989, Microbiol Rev. 53(1):148-70 and EP-A-0 635 574).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention is further described by the following examples, which should not be construed as limiting the scope of the invention.

EXAMPLES

Plasmid and Strain Construction

Strains

The L-arabinose consuming *Sachharomyces cerevisiae* strain described in this work is based on strain RWB220, which is itself a derivative of RWB217. RWB217 is a CEN.PK strain in which four genes coding for the expression of enzymes in the pentose phosphate pathway have been overexpressed, TAL1, TKL1, RPE1, RKI1 (Kuyper et al., 2005a). In addition the gene coding for an aldose reductase (GRE3), has been deleted. Strain RWB217 also contains two plasmids, a single copy plasmid with a LEU2 marker for overexpression of the xylulokinase (XKS1) and an episomal, multicopy plasmid with URA3 as the marker for the expression of the xylose isomerase, XylA. RWB217 was subjected to a selection procedure for improved growth on xylose which is described in Kuyper et al. (2005b). The procedure resulted in two pure strains, RWB218 (Kuyper et al., 2005b) and RWB219. The difference between RWB218 and RWB219 is that after the selection procedure, RWB218 was obtained by plating and restreaking on mineral medium with glucose as the carbon source, while for RWB219 xylose was used.

Strain RWB219 was grown non-selectively on YP with glucose (YPD) as the carbon source in order to facilitate the loss of both plasmids. After plating on YPD single colonies were tested for plasmid loss by looking at uracil and leucine auxotrophy. A strain that had lost both plasmids was transformed with pSH47, containing the cre recombinase, in order to remove a KanMX cassette (Guldener et al., 1996), still present after integrating the RKIJ overexpression construct. Colonies with the plasmid were resuspended in Yeast Peptone medium (YP) (10 g/l yeast extract and 20 g/l peptone both from BD Difco Belgium) with 1% galactose and incubated for 1 hour at 30° C. About 200 cells were plated on YPD. The resulting colonies were checked for loss of the KanMX marker (G418 resistance) and pSH47 (URA3). A strain that had lost both the KanMX marker and the pSH47 plasmid was then named RWB220. To obtain the strain tested in this patent, RWB220 was transformed with pRW231 and pRW243 (table 2), resulting in strain IMS0001.

During construction strains were maintained on complex YP: 10 gl$^{-1}$ yeast extract (BD Difco), 20 gl$^{-1}$ peptone (BD Difco) or synthetic medium (MY) (Verduyn et al., 1992) supplemented with glucose (2%) as carbon source (YPD or MYD) and 1.5% agar in the case of plates. After transformation with plasmids strains were plated on MYD. Transformations of yeast were done according to Gietz and Woods (2002). Plasmids were amplified in *Escherichia coli* strain XL-1 blue (Stratagene, La Jolla, Calif., USA). Transformation was performed according to Inoue et al. (1990). *E. coli* was grown on LB (Luria-Bertani) plates or in liquid TB (Terrific Broth) medium for the isolation of plasmids (Sambrook et al, 1989).

Plasmids

In order to grow on L-arabinose, yeast needs to express three different genes, an L-arabinose isomerase (AraA), a L-ribulokinase (AraB), and a L-ribulose-5-P 4-epimerase (AraD) (Becker and Boles, 2003). In this work we have chosen to express AraA, AraB, and AraD from the lactic acid bacterium *Lactobacillus plantarum* in *S. cerevisiae*. Because the eventual aim is to consume L-arabinose in combination with other sugars, like D-xylose, the genes encoding the bacterial L-arabinose pathway were combined on the same plasmid with the genes coding for D-xylose consumption.

In order to get a high level of expression, the *L. plantarum* AraA and AraD genes were ligated into plasmid pAKX002, the 2µ XylA bearing plasmid.

The AraA cassette was constructed by amplifying a truncated version of the TDH3 promoter with SpeI5'Ptdh3 and 5'AraAPtdh3 (SEQ ID NO: 49), the AraA gene with Ptdh5'AraA and Tadh3'AraA and the ADH1 terminator (SEQ ID NO:50) with 3'AraATadh1 and 3'Tadh1-SpeI. The three fragments were extracted from gel and mixed in roughly equimolar amounts. On this mixture a PCR was performed using the SpeI-5'Ptdh3 and 3'Tadh1SpeI oligos. The resulting $P_{TDH3}$-AraA-$T_{ADH1}$ cassette was gel purified, cut at the 5' and 3' SpeI sites and then ligated into pAKX002 cut with NheI, resulting in plasmid pRW230.

The AraD construct was made by first amplifying a truncated version of the HXT7 promoter (SEQ ID NO:52) with oligos SalI5'Phxt7 and 5'AraDPhxt, the AraD gene with Phxt5'AraD and Tpgi3'AraD and the GPI1 terminator (SEQ ID NO:53) region with the 3'AraDTpgi and 3'TpgiSalI oligos. The resulting fragments were extracted from gel and mixed in roughly equimolar amounts, after which a PCR was performed using the SalI5'Phxt7 and 3'Tpgi1SalI oligos. The resulting $P_{HXT7}$-AraD-$T_{PGI1}$ cassette was gel purified, cut at the 5' and 3' SalI sites and then ligated into pRW230 cut with XhoI, resulting in plasmid pRW231 (FIG. 1).

Since too high an expression of the L-ribulokinase is detrimental to growth (Becker and Boles, 2003), the AraB gene was combined with the XKS1 gene, coding for xylulokinase, on an integration plasmid. For this, p415ADHXKS (Kuyper et al., 2005a) was first changed into pRW229, by cutting both p415ADHXKS and pRS305 with PvuI and ligating the ADHXKS-containing PvuI fragment from p415ADHXKS to the vector backbone from pRS305, resulting in pRW229.

A cassette, containing the *L. plantarum* AraB gene between the PGI1 promoter (SEQ ID NO:51) and ADH1 terminator (SEQ ID NO:50) was made by amplifying the PGI1 promoter with the SacIS'Ppgi1 and 5'AraBPpgi1 oligos, the AraB gene with the Ppgi5'AraB and Tadh3'AraB oligos and the ADH1 terminator with 3'AraBTadh1 and 3'Tadh1SacI oligos. The three fragments were extracted from gel and mixed in roughly equimolar amounts. On this mixture a PCR was performed using the SacI-5'Ppgi1 and 3'Tadh1SacI oligos. The resulting $P_{PGI1}$-AraB-$T_{ADH1}$ cassette was gel purified, cut at the 5' and 3' SacI sites and then ligated into pRW229 cut with SacI, resulting in plasmid pRW243 (FIG. 1).

Strain RWB220 was transformed with pRW231 and pRW243 (table 2), resulting in strain IMS0001.

Restriction endonucleases (New England Biolabs, Beverly, Mass., USA and Roche, Basel, Switzerland) and DNA ligase (Roche) were used according to the manufacturers' specifications. Plasmid isolation from *E. coli* was performed with the Qiaprep spin miniprep kit (Qiagen, Hilden, Germany). DNA fragments were separated on a 1% agarose (Sigma, St. Louis, Mo., USA) gel in 1×TBE (Sambrook et al, 1989). Isolation of fragments from gel was carried out with the Qiaquick gel extraction kit (Quiagen). Amplification of the (elements of the) AraA, AraB and AraD cassettes was done with Vent$_R$ DNA polymerase (New England Biolabs) according to the manufacturer's specification. The template was chromosomal DNA of *S. cerevisiae* CEN.PK113-7D for the promoters and terminators, or *Lactobacillus plantarum* DSM20205 for the Ara genes. The polymerase chain reaction (PCR) was performed in a Biometra TGradient Thermocycler (Biometra, Gottingen, Germany) with the following settings: 30 cycles of 1 min annealing at 55° C., 60° C. or 65° C., 1 to 3 min extension at 75° C., depending on expected fragment size, and 1 min denaturing at 94° C.

Cultivation and Media

Shake-flask cultivations were performed at 30° C. in a synthetic medium (Verduyn et al., 1992). The pH of the medium was adjusted to 6.0 with 2 M KOH prior to sterilisation. For solid synthetic medium, 1.5% of agar was added.

Pre-cultures were prepared by inoculating 100 ml medium containing the appropriate sugar in a 500-ml shake flask with a frozen stock culture. After incubation at 30° C. in an orbital shaker (200 rpm), this culture was used to inoculate either shake-flask cultures or fermenter cultures. The synthetic medium for anaerobic cultivation was supplemented with 0.01 gl$^{-1}$ ergosterol and 0.42 gl$^{-1}$ Tween 80 dissolved in ethanol (Andreasen and Stier, 1953; Andreasen and Stier, 1954). Anaerobic (sequencing) batch cultivation was carried out at 30° C. in 2-1 laboratory fermenters (Applikon, Schiedam, The Netherlands) with a working volume of 1 l. The culture pH was maintained at pH 5.0 by automatic addition of 2 M KOH. Cultures were stirred at 800 rpm and sparged with 0.5 l min$^{-1}$ nitrogen gas (<10 ppm oxygen). To minimise diffusion of oxygen, fermenters were equipped with Norprene tubing (Cole Palmer Instrument company, Vernon Hills, USA). Dissolved oxygen was monitored with an oxygen electrode (Applisens, Schiedam, The Netherlands). Oxygen-limited conditions were achieved in the same experimental set-up by headspace aeration at approximately 0.05 l min$^{-1}$.

Determination of Dry Weight

Culture samples (10.0 ml) were filtered over preweighed nitrocellulose filters (pore size 0.45 µm; Gelman laboratory, Ann Arbor, USA). After removal of medium, the filters were washed with demineralised water and dried in a microwave oven (Bosch, Stuttgart, Germany) for 20 min at 360 W and weighed. Duplicate determinations varied by less than 1%.

Gas Analysis

Exhaust gas was cooled in a condensor (2° C.) and dried with a Permapure dryer type MD-110-48P-4 (Permapure, Toms River, USA). O2 and CO2 concentrations were determined with a NGA 2000 analyser (Rosemount Analytical, Orrville, USA). Exhaust gasflow rate and specific oxygen-consumption and carbondioxide production rates were determined as described previously (Van Urk et al., 1988; Weusthuis et al., 1994). In calculating these biomass-specific rates, volume changes caused by withdrawing culture samples were taken account for.

Metabolite Analysis

Glucose, xylose, arabinose, xylitol, organic acids, glycerol and ethanol were analysed by HPLC using a Waters Alliance 2690 HPLC (Waters, Milford, USA) supplied with a BioRad HPX 87H column (BioRad, Hercules, USA), a Waters 2410 refractive-index detector and a Waters 2487 UV detector. The column was eluted at 60° C. with 0.5 gl$^{-1}$ sulphuric acid at a flow rate of 0.6 ml min$^{-1}$.

Assay for Xylulose 5-Phosphate (Zaldivar J., et al, Appl. Microbiol. Biotechnol., (2002), 59:436-442)

For the analysis of intracellular metabolites such as xylulose 5-phosphate, 5 ml broth was harvested in duplicate from the reactors, before glucose exhaustion (at 22 and 26 h of cultivation) and after glucose exhaustion (42, 79 and 131 h of cultivation). Procedures for metabolic arrest, solid-phase extraction of metabolites and analysis have been described in detail by Smits H. P. et al. (Anal. Biochem., 261:36-42, (1998)). However, the analysis by high-pressure ion exchange chromatography coupled to pulsed amperometric detection used to analyze cell extracts, was slightly modified. Solutions used were eluent A, 75 mM NaOH, and eluent B, 500 mM NaAc. To prevent contamination of carbonate in the eluent solutions, a 50% NaOH solution with low carbonate concentration (Baker Analysed, Deventer, The Netherlands) was used instead of NaOH pellets. The eluents were degassed with Helium (He) for 30 min and then kept under a He atmosphere. The gradient pump was programmed to generate the following gradients: 100% A and 0% B (0 min), a linear decrease of A to 70% and a linear increase of B to 30% (0-30 min), a linear decrease of A to 30% and a linear increase of B to 70% (30-70 min), a linear decrease of A to 0% and a linear increase of B to 100% (70-75 min), 0% A and 100% B (75-85 min), a linear increase of A to 100% and a linear decrease of B to 0% (85-95 min) The mobile phase was run at a flow rate of 1 ml/min. Other conditions were according to Smits et al. (1998).

Carbon Recovery

Carbon recoveries were calculated as carbon in products formed, divided by the total amount of sugar carbon consumed, and were based on a carbon content of biomass of 48%. To correct for ethanol evaporation during the fermentations, the amount of ethanol produced was assumed to be equal to the measured cumulative production of $CO_2$ minus the $CO_2$ production that occurred due to biomass synthesis (5.85 mmol $CO_2$ per gram biomass (Verduyn et al., 1990)) and the $CO_2$ associated with acetate formation.

Selection for Growth on L-Arabinose

Strain IMS0001 (CBS120327 deposited at the CBS on Sep. 27, 2006), containing the genes encoding the pathways for both xylose (XylA and XKS1) and arabinose (AraA, AraB, AraD) metabolization, was constructed according the procedure described above. Although capable of growing on xylose (data not shown), strain IMS0001 did not seem to be capable of growing on solid synthetic medium supplemented with 2% L-arabinose. Mutants of IMS0001 capable of utilizing L-arabinose as carbon source for growth were selected by serial transfer in shake flasks and by sequencing-batch cultivation in fermenters (SBR).

Figure 2:
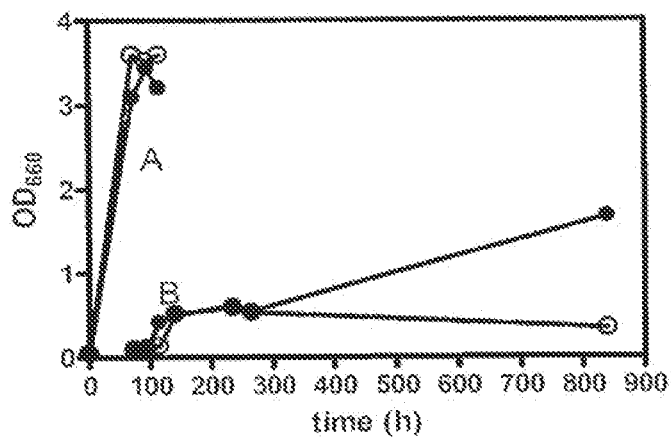
FIG. 2. Growth pattern of shake flask cultivations of strain RWB219 (○) and IMS0001 (●) in synthetic medium containing 0.5% galactose (A) and 0.1% galactose+2% L-arabinose (B). Cultures were grown for 72 hours in synthetic medium with galactose (A) and then transferred to synthetic medium with galactose and arabinose (B). Growth was determined by measuring the OD$_{660}$.
Figure 3:
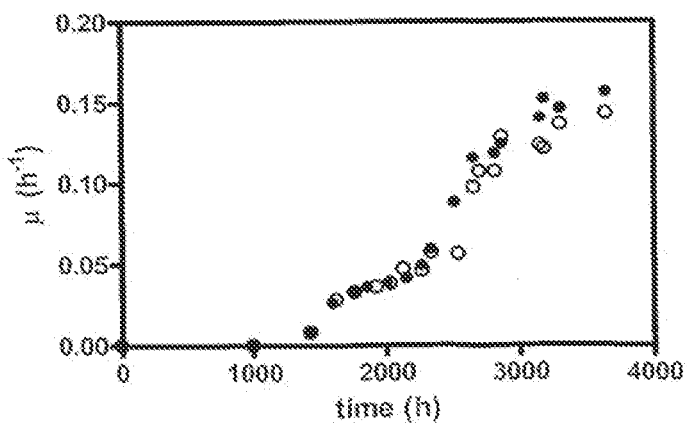
FIG. 3. Growth rate during serial transfers of *S. cerevisiae* IMS0001 in shake flask cultures containing synthetic medium with 2% (w/v) L-arabinose. Each datapoint represents the growth rate estimated from the OD$_{660}$ measured during (exponential) growth. The closed and open circles represent duplicate serial transfer experiments.

For the serial transfer experiments, a 500-ml shake flask containing 100 ml synthetic medium containing 0.5% galactose were inoculated with either strain IMS0001, or the reference strain RWB219. After 72 hours, at an optical density at 660 nm of 3.0, the cultures were used to inoculate a new shake flask containing 0.1% galactose and 2% arabinose. Based on HPLC determination with D-ribulose as calibration standard, it was determined that already in the first cultivations of strain IMS0001, on medium containing a galactose/arabinose mixture, part of the arabinose was converted into ribulose and subsequently excreted to the supernatant. These HPLC analyses were performed using a Waters Alliance 2690 HPLC (Waters, Milford, USA) supplied with a BioRad HPX 87H column (BioRad, Hercules, USA), a Waters 2410 refractive-index detector and a Waters 2487 UV detector. The column was eluted at 60° C. with 0.5 gl$^{-1}$ sulphuric acid at a flow rate of 0.6 ml min$^{-1}$. In contrast to the reference strain RWB219, the $OD_{660}$ of the culture of strain IMS0001 increased after depletion of the galactose. When after approximately 850 hours growth on arabinose by strain IMS0001 was observed (FIG. 2), this culture was transferred at an $OD_{660}$ of 1.7 to a shake flask containing 2% arabinose. Cultures were then sequentially transferred to fresh medium containing 2% arabinose at an $OD_{660}$ of 2-3. Utilization of arabinose was confirmed by occasionally measuring arabinose concentrations by HPLC (data not shown). The growth rate of these cultures increased from 0 to 0.15 h$^{-1}$ in approximately 3600 hours (FIG. 3).

Figure 4:
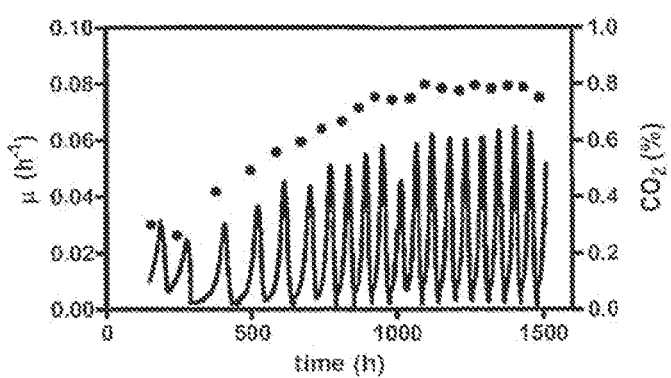
FIG. 4. Growth rate during an anaerobic SBR fermentation of *S. cerevisiae* IMS0001 in synthetic medium with 2% (w/v) L-arabinose. Each datapoint represents the growth rate estimated from the CO$_2$ profile (solid line) during exponential growth.

A batch fermentation under oxygen limited conditions was started by inoculating 1 l of synthetic medium supplemented with 2% of arabinose with a 100 ml shake flask culture of arabinose-grown IMS0001 cells with a maximum growth rate on 2% of L-arabinose of approximately 0.12 h$^{-1}$. When growth on arabinose was observed, the culture was subjected to anaerobic conditions by sparging with nitrogen gas. The sequential cycles of anaerobic batch cultivation were started by either manual or automated replacement of 90% of the culture with synthetic medium with 20 gl$^{-1}$ arabinose. For each cycle during the SBR fermentation, the exponential growth rate was estimated from the $CO_2$ profile (FIG. 4). In 13 cycles, the exponential growth rate increased from 0.025 to 0.08 h$^{-1}$. After 20 cycles a sample was taken, and plated on solid synthetic medium supplemented with 2% of L-arabinose and incubated at 30° C. for several days. Separate colonies were re-streaked twice on solid synthetic medium with L-arabinose. Finally, a shake flask containing synthetic medium with 2% of L-L-arabinose was inoculated with a single colony, and incubated for 5 days at 30° C. This culture was designated as strain IMS0002 (CBS120328 deposited at the Centraal Bureau voor Schimmelculturen (CBS) on Sep. 27, 2006). Culture samples were taken, 30% of glycerol was added and samples were stored at −80° C.

Mixed Culture Fermentation

Biomass hydrolysates, a desired feedstock for industrial biotechnology, contain complex mixtures consisting of various sugars amongst which glucose, xylose and arabinose are commonly present in significant fractions. To accomplish ethanolic fermentation of not only glucose and arabinose, but also xylose, an anaerobic batch fermentation was performed with a mixed culture of the arabinose-fermenting strain IMS0002, and the xylose-fermenting strain RWB218. An anaerobic batch fermenter containing 800 ml of synthetic medium supplied with 30 $gl^{-1}$ D-glucose, 15 $gl^{-1}$ D-xylose, and 15 $gl^{-1}$ L-arabinose was inoculated with 100 ml of pre-culture of strain IMS0002. After 10 hours, a 100 ml inoculum of RWB218 was added. In contrast to the mixed sugar fermentation with only strain IMS0002, both xylose and arabinose were consumed after glucose depletion (FIG. 5D). The mixed culture completely consumed all sugars, and within 80 hours 564.0±6 3 mmol $l^{-1}$ ethanol (calculated from the $CO_2$ production) was produced with a high overall yield of 0.42 g $g^{-1}$ sugar. Xylitol was produced only in small amounts, to a concentration of 4.7 mmol $l^{-1}$.

Characterization of Strain IMS0002

Growth and product formation of strain IMS0002 was determined during anaerobic batch fermentations on synthetic medium with either L-arabinose as the sole carbon source, or a mixture of glucose, xylose and L-arabinose. The pre-cultures for these anaerobic batch fermentations were prepared in shake flasks containing 100 ml of synthetic medium with 2% L-arabinose, by inoculating with −80° C. frozen stocks of strain IMS0002, and incubating for 48 hours at 30° C.

Figure 5A:
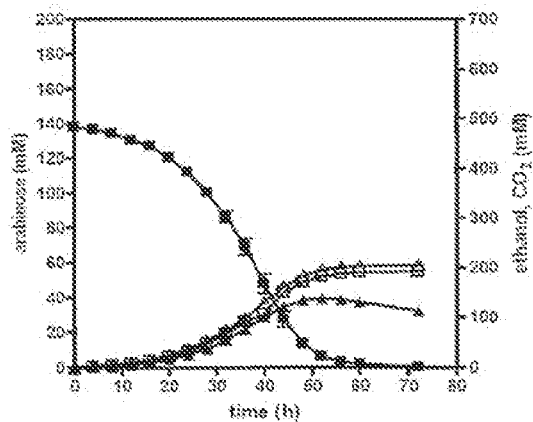
FIG. 5. Sugar consumption and product formation during anaerobic batch fermentations of strain IMS0002. The fermentations were performed in 1 synthetic medium supplemented with: 20 gl$^{-1}$ arabinose (A); 20 gl$^{-1}$ glucose and 20 gl$^{-1}$ arabinose (B); 30 gl$^{-1}$ glucose, 15 gl$^{-1}$ xylose, and 15 gl$^{-1}$ arabinose (C); Sugar consumption and product formation during anaerobic batch fermentations with a mixture of strains IMS0002 and RWB218. The fermentations were performed in 1 liter of synthetic medium supplemented with 30 gl$^{-1}$ glucose, 15 gl$^{-1}$ xylose, and 15 gl$^{-1}$ arabinose (D). Symbols: glucose (●); xylose (○); arabinose (■); ethanol calculated from cumulative CO$_2$ production (□); ethanol measured by HPLC (▲); cumulative CO$_2$ production (Δ); xylitol (▼)
Figure 5B:
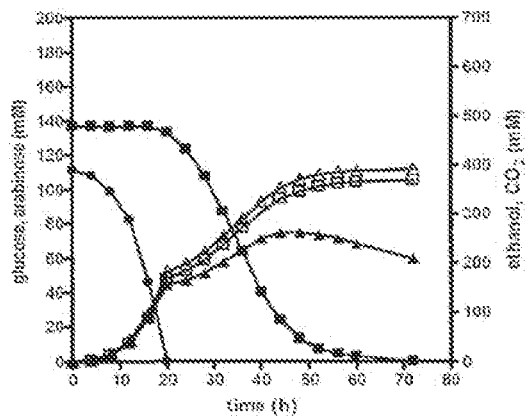

FIG. 5A shows that strain IMS0002 is capable of fermenting 20 $gl^{-1}$ L-arabinose to ethanol during an anaerobic batch fermentation of approximately 70 hours. The specific growth rate under anaerobic conditions with L-arabinose as sole carbon source was 0.05±0.001 $h^{-1}$. Taking into account the ethanol evaporation during the batch fermentation, the ethanol yield from 20 $gl^{-1}$ arabinose was 0.43±0.003 g $g^{-1}$. Without evaporation correction the ethanol yield was 0.35±0.01 g $g^{-1}$ of arabinose. No formation of arabinitol was observed during anaerobic growth on arabinose. In FIG. 5B, the ethanolic fermentation of a mixture of 20 $gl^{-1}$ glucose and 20 g $l^{-1}$ L-arabinose by strain IMS0002 is shown. L-arabinose consumption started after glucose depletion. Within 70 hours, both the glucose and L-arabinose were completely consumed. The ethanol yield from the total of sugars was 0.42±0.003 g $g^{-1}$.

Figure 5C:
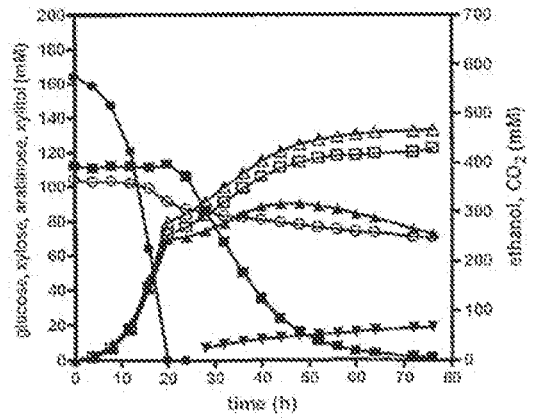
Figure 5D:
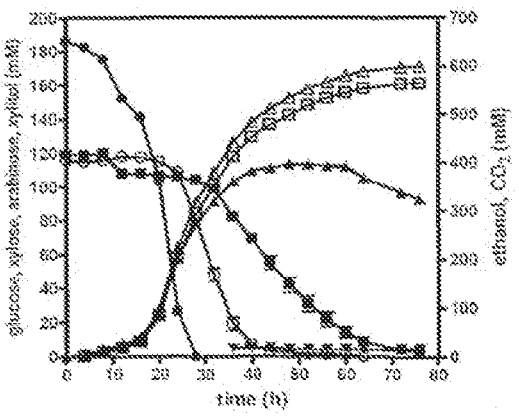

In FIG. 5C, the fermentation profile of a mixture of 30 $gl^{-1}$ glucose, 15 $gl^{-1}$ D-xylose, and 15 $gl^{-1}$ L-arabinose by strain IMS0002 is shown. Arabinose consumption started after glucose depletion. Within 80 hours, both the glucose and arabinose were completely consumed. Only 20 mM from 100 mM of xylose was consumed by strain IMS0002. In addition, the formation of 20 mM of xylitol was observed. Apparently, the xylose was converted into xylitol by strain IMS0002. Hence, the ethanol yield from the total of sugars was lower than for the above described fermentations: 0.38±0.001 g $g^{-1}$. The ethanol yield from the total of glucose and arabinose was similar to the other fermentations: 0.43±0.001 g $g^{-1}$.

Table 1 shows the arabinose consumption rates and the ethanol production rates observed for the anaerobic batch fermentation of strain IMS0002. Arabinose was consumed with a rate of 0.23-0.75 g $h^{-1}$ $g^{-1}$ biomass dry weight. The rate of ethanol produced from arabinose varied from 0.08-0.31 g $h^{-1}$ $g^{-1}$ biomass dry weight.

Figure 6:
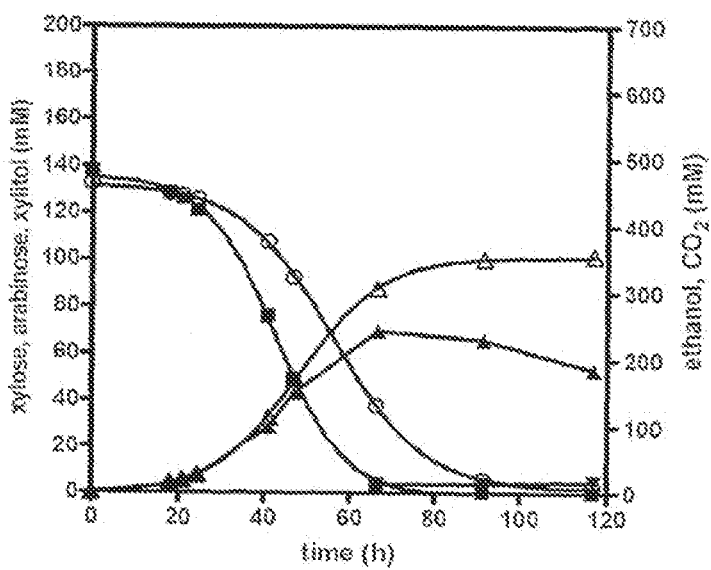
FIG. 6. Sugar consumption and product formation during an anaerobic batch fermentation of strain IMS0002 cells selected for anaerobic growth on xylose. The fermentation was performed in 1 liter of synthetic medium supplemented with 20 gl$^{-1}$ xylose and 20 gl$^{-1}$ arabinose. Symbols: xylose (○); arabinose (■); ethanol measured by HPLC (▲); cumulative CO$_2$ production (Δ); xylitol (▼).

Initially, the constructed strain IMS0001 was able to ferment xylose (data not shown). In contrast to our expectations, the selected strain IMS0002 was not capable of fermenting xylose to ethanol (FIG. 5C). To regain the capability of fermenting xylose, a colony of strain IMS0002 was transferred to solid synthetic medium with 2% of D-xylose, and incubated in an anaerobic jar at 30° C. for 25 days. Subsequently, a colony was again transferred to solid synthetic medium with 2% of arabinose. After 4 days of incubation at 30° C., a colony was transferred to a shake flask containing synthetic medium with 2% arabinose. After incubation at 30° C. for 6 days, 30% of glycerol was added, samples were taken and stored at −80° C. A shake flask containing 100 ml of synthetic medium with 2% arabinose was inoculated with such a frozen stock, and was used as preculture for an anaerobic batch fermentation on synthetic medium with 20 $gl^{-1}$ xylose and 20 $gl^{1}$ arabinose. In FIG. 6, the fermentation profile of this batch fermentation is shown. Xylose and arabinose were consumed simultaneously. The arabinose was completed within 70 hours, whereas the xylose was completely consumed in 120 hours. At least 250 mM of ethanol was produced from the total of sugars, not taking into account the evaporation of the ethanol. Assuming an end biomass dry weight of 3.2 $gl^{-1}$ (assuming a biomass yield of 0.08 g $g^{-1}$ sugar), the end ethanol concentration estimated from the cumulative $CO_2$ production (355 mmol $l^{-1}$) was approximately 330 mmol $l^{-1}$, corresponding to a ethanol yield of 0.41 g $g^{-1}$ pentose sugar. In addition to ethanol, glycerol, and organic acids, a small amount of xylitol was produced (approximately 5 mM).

Selection of Strain IMS0003

Initially, the constructed strain IMS0001 was able to ferment xylose (data not shown). In contrast to our expectations, the selected strain IMS0002 was not capable of fermenting xylose to ethanol (FIG. 5C). To regain the capability of fermenting xylose, a colony of strain IMS0002 was transferred to solid synthetic medium with 2% of D-xylose, and incubated in an anaerobic jar at 30° C. for 25 days. Subsequently, a colony was again transferred to solid synthetic medium with 2% of arabinose. After 4 days of incubation at 30° C., a colony was transferred to a shake flask containing synthetic medium with 2% arabinose. After incubation at 30° C. for 6 days, 30% of glycerol was added, samples were taken and stored at −80° C.

From this frozen stock, samples were spread on solid synthetic medium with 2% of L-arabinose and incubated at 30° C. for several days. Separate colonies were re-streaked twice on solid synthetic medium with L-arabinose. Finally, a shake flask containing synthetic medium with 2% of L-arabinose was inoculated with a single colony, and incubated for 4 days at 30° C. This culture was designated as strain IMS0003 (CBS 121879 deposited at the CBS on Sep. 20, 2007). Culture samples were taken, 30% of glycerol was added and samples were stored at −80° C.

Characterization of Strain IMS0003

Growth and product formation of strain IMS0003 was determined during an anaerobic batch fermentation on synthetic medium with a mixture of 30 $gl^{-1}$ glucose, 15 $gl^{-1}$ D-xylose and 15 $gl^{-1}$ L-arabinose. The pre-culture for this anaerobic batch fermentation was prepared in a shake flasks containing 100 ml of synthetic medium with 2% L-arabinose, by inoculating with a −80° C. frozen stock of strain IMS0003, and incubated for 48 hours at 30° C.

Figure 7:
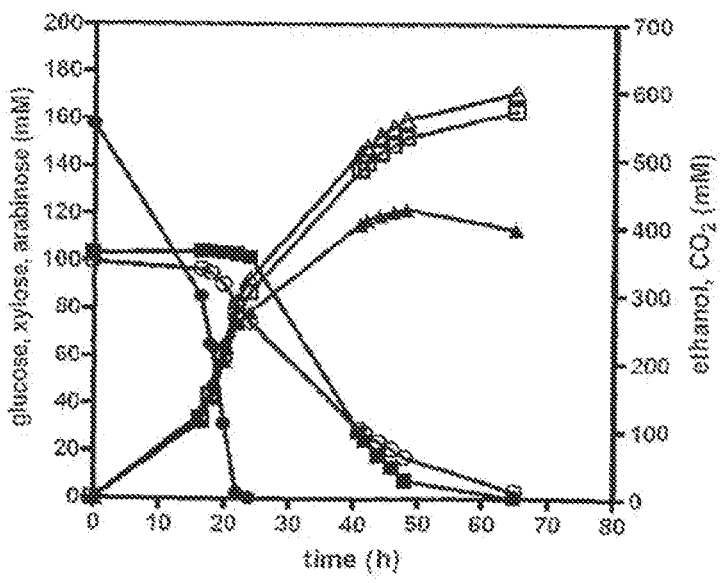
FIG. 7. Sugar consumption and product formation during an anaerobic batch fermentation of strain IMS0003. The fermentation was performed in 1 liter of synthetic medium supplemented with: 30 gl$^{-1}$ glucose, 15 gl$^{-1}$ xylose, and 15 gl$^{-1}$ arabinose. Symbols: glucose (●); xylose (○); arabinose (■); ethanol calculated from cumulative CO$_2$ production (□); ethanol measured by HPLC (▲); cumulative CO$_2$ production (Δ)

In FIG. 7, the fermentation profile of a mixture of 30 $gl^{-1}$ glucose, 15 $gl^{-1}$ D-xylose, and 15 $gl^{-1}$ L-arabinose by strain IMS0003 is shown. Arabinose consumption started after glucose depletion. Within 70 hours, the glucose, xylose and arabinose were completely consumed. Xylose and arabinose were consumed simultaneously. At least 406 mM of ethanol was produced from the total of sugars, not taking into account the evaporation of the ethanol. The final ethanol concentration calculated from the cumulative $CO_2$ production was 572 mmol $l^{-1}$, corresponding to an ethanol yield of 0.46 g $g^{-1}$ of total sugar. In contrast to the fermentation of a mixture of glucose, xylose and arabinose by strain IMS0002 (FIG. 5C) or a mixed culture of strains IMS0002 and RWB218 (FIG. 5D), strain IMS0003 did not produce detectable amounts of xylitol.

Tables

TABLE 1

*S. cerevisiae* strains used.

| Strain | Characteristics | Reference |
|---|---|---|
| RWB217 | MATA ura3-52 leu2-112 loxP-$P_{TPI}$::(−266, −1)TAL1 gre3::hphMXpUGP$_{TPI}$-TKL1 pUGP$_{TPI}$-RPE1 KanloxP-$P_{TPI}$::(−?, −1)RKI1 {p415ADHXKS, pAKX002} | Kuyper et al. 2005a |
| RWB218 | MATA ura3-52 leu2-112 loxP-$P_{TPI}$::(−266, −1)TAL1 gre3::hphMXpUGP$_{TPI}$-TKL1 pUGP$_{TPI}$-RPE1 KanloxP-$P_{TPI}$::(−?, −1)RKI1 {p415ADHXKS1, pAKX002} | Kuyper et al. 2005b |
| RWB219 | MATA ura3-52 leu2-112 loxP-$P_{TPI}$::(−266, −1)TAL1 gre3::hphMXpUGP$_{TPI}$-TKL1 pUGP$_{TPI}$-RPE1 KanloxP-$P_{TPI}$::(−?, −1)RKI1 {p415ADHXKS1, pAKX002} | This work |
| RWB220 | MATA ura3-52 leu2-112 loxP-$P_{TPI}$::(−266, −1)TAL1 gre3::hphMXpUGP$_{TPI}$-TKL1 pUGP$_{TPI}$-RPE1 loxP-$P_{TPI}$::(−?, −1)RKI1 | This work |
| IMS0001 | MATA ura3-52 leu2-112 loxP-$P_{TPI}$::(−266, −1)TAL1 gre3::hphMXpUGP$_{TPI}$-TKL1 pUGP$_{TPI}$-RPE1 loxP-$P_{TPI}$::(−?, −1)RKI1 {pRW231, PRW243} | This work |
| IMS0002 | MATA ura3-52 leu2-112 loxP-$P_{TPI}$::(−266, −1)TAL1 gre3::hphMXpUGP$_{TPI}$-TKL1 pUGP$_{TPI}$-RPE1 loxP-$P_{TPI}$::(−?, −1)RKI1 {pRW231, PRW243} selected for anaerobic growth on L-arabinose | This work |

TABLE 2

Plasmids used

| plasmid | characteristics | Reference |
|---|---|---|
| pRS305 | Integration, LEU2 | Gietz and Sugino, 1988 |
| pAKX002 | 2µ, URA3, $P_{TPI1}$-Piromyces xylA | Kuyper et al. 2003 |
| p415ADHXKS1 | CEN, LEU2, $P_{ADH1}$-S.cerXKS1 | Kuyper et al., 2005a |
| pRW229 | integration, LEU2, $P_{ADH1}$-S.cerXKS1 | This work |
| pRW230 | pAKX002 with $P_{TDH3}$-AraA | This work |
| pRW231 | pAKX002 with $P_{TDH3}$-AraA and $P_{HXT7}$-AraD | This work |
| pRW243 | LEU2, integration, $P_{ADH1}$-ScXKS1-$T_{CYC}$, $P_{PGI1}$-L. plantarumAraB-$T_{ADH1}$ | This work |

TABLE 3 oligos used in this work

| Oligo | DNA sequence |
|---|---|

AraA expression cassette

| | |
|---|---|
| SpeI5'Ptdh3 SEQ ID NO: 31 | 5'GACTAGTCGAGTTTATCATTATCAATACTGC3' |
| 5'AraAPtdh SEQ ID NO: 32 | 5'CTCATAATCAGGTACTGATAACATTTTGTTTGTTTATGTGTGTTTATTC3' |
| Ptdh5'AraA SEQ ID NO: 33 | 5'GAATAAACACACATAAACAAACAAAATGTTATCAGTACCTGATTATGAG3' |
| Tadh3'AraA SEQ ID NO: 34 | 5'AATCATAAATCATAAGAAATTCGCTTACTTTAAGAATGCCTTAGTCAT3' |
| 3'AraATadh1 SEQ ID NO: 35 | 5'ATGACTAAGGCATTCTTAAAGTAAGCGAATTTCTTATGATTTATGATT3' |
| 3'Tadh1SpeI SEQ ID NO: 36 | 5'CACTAGTCTCGAGTGTGGAAGAACGATTACAACAGG3' |

AraB expression cassette

| | |
|---|---|
| SacI5'Ppgi1 SEQ ID NO: 37 | 5'CGAGCTCGTGGGTGTATTGGATTATAGGAAG3' |
| 5'AraBPpgi1 SEQ ID NO: 38 | 5'TTGGGCTGTTTCAACTAAATTCATTTTTAGGCTGGTATCTTGATTCTA3' |
| Ppgi5'AraB SEQ ID NO: 39 | 5'TAGAATCAAGATACCAGCCTAAAAATGAATTTAGTTGAAACAGCCCAA3' |
| Tadh3'AraB SEQ ID NO: 40 | 5'AATCATAAATCATAAGAAATTCGCTCTAATATTTGATTGCTTGCCCAG3' |
| 3'AraBTadh1 SEQ ID NO: 41 | 5'CTGGGCAAGCAATCAAATATTAGAGCGAATTTCTTATGATTTATGATT3' |
| 3'Tadh1SacI SEQ ID NO: 42 | 5'TGAGCTCGTGTGGAAGAACGATTACAACAGG3' |

TABLE 3-continued oligos used in this work

| Oligo | DNA sequence |
|---|---|

AraD expression cassette

| | |
|---|---|
| SalI5'Phxt7<br>SEQ ID NO: 43 | 5'ACGCGTCGACTCGTAGGAACAATTTCGG3' |
| 5'AraDPhxt<br>SEQ ID NO: 44 | 5'CTTCTTGTTTTAATGCTTCTAGCATTTTTTGATTAAAATTAAAAAAACTT3' |
| Phxt5'AraD<br>SEQ ID NO: 45 | 5'AAGTTTTTTAATTTTAATCAAAAAATGCTAGAAGCATTAAAACAAGAAG3' |
| Tpgi3'AraD<br>SEQ ID NO: 46 | 5'GGTATATATTTAAGAGCGATTTGTTTACTTGCGAACTGCATGATCC3' |
| 3'AraDTpgi<br>SEQ ID NO: 47 | 5'GGATCATGCAGTTCGCAAGTAAACAAATCGCTCTTAAATATATACC3' |
| 3'TpgiSalI<br>SEQ ID NO: 48 | 5'CGCAGTCGACCTTTTAAACAGTTGATGAGAACC3' |

TABLE 4

Maximum observed specific glucose and arabinose consumption rates and ethanol production rates during anaerobic batch fermentations of *S. cerevisiae* IMS0002.

| C-source | $q_{glu}$ g h$^{-1}$ g$^{-1}$ DW | $q_{ara}$ g h$^{-1}$ g$^{-1}$ DW | $q_{eth,glu}$ g h$^{-1}$ g$^{-1}$ DW | $q_{eth,ara}$ g h$^{-1}$ g$^{-1}$ DW |
|---|---|---|---|---|
| 20 g l$^{-1}$ arabinose | — | 0.75 ± 0.04 | — | 0.31 ± 0.02 |
| 20 g l$^{-1}$ glucose 20 g l$^{-1}$ arabinose | 2.08 ± 0.09 | 0.41 ± 0.01 | 0.69 ± 0.00 | 0.19 ± 0.00 |
| 30 g l$^{-1}$ glucose 15 g l$^{-1}$ xylose 15 g l$^{-1}$ arabinose | 1.84 ± 0.04 | 0.23 ± 0.01 | 0.64 ± 0.03 | 0.08 ± 0.01 |

$q_{glu}$: specific glucose consumption rate
$q_{ara}$: specific arabinose consumption rate
$q_{eth,glu}$: specific ethanol production rate during growth on glucose
$q_{eth,ara}$: specific ethanol production rate during growth on arabinose

REFERENCE LIST

Andreasen A A, Stier T J (1954) Anaerobic nutrition of *Saccharomyces cerevisiae*. II. Unsaturated fatty acid requirement for growth in a defined medium. J Cell Physiol 43:271-281

Andreasen A A, Stier T J (1953) Anaerobic nutrition of *Saccharomyces cerevisiae*. I. Ergosterol requirement for growth in a defined medium. J Cell Physiol 41:23-36

Becker J, Boles E (2003) A modified *Saccharomyces cerevisiae* strain that consumes L-Arabinose and produces ethanol. Appl Environ Microbiol 69:4144-4150

Gietz R. D., Sugino A. (1988). New yeast-*Escherichia coli* shuttle vectors constructed with in vitro mutagenized yeast genes lacking six-base pair restriction sites. Gene 74:527-534.

Gietz, R. D., and R. A. Woods. 2002. Transformation of yeast by lithium acetate/single-stranded carrier DNA/polyethylene glycol method. Methods Enzymol. 350:87-96.

Guldener U, Heck S, Fielder T, Beinhauer J, Hegemann J H. (1996) A new efficient gene disruption cassette for repeated use in budding yeast. Nucleic Acids Res. 1996 Jul. 1; 24(13):2519-24.

Hauf J, Zimmermann F K, Muller S. Simultaneous genomic overexpression of seven glycolytic enzymes in the yeast *Saccharomyces cerevisiae*. Enzyme Microb Technol. 2000 Jun. 1; 26(9-10):688-698.

Inoue H., H. Nojima and H. Okayama, High efficiency transformation of *Escherichia coli* with plasmids. *Gene* 96 (1990), pp. 23-28

Kuyper M, Hartog M M P, Toirkens M J, Almering M J H, Winkler A A, Van Dijken J P, Pronk J T (2005a) Metabolic engineering of a xylose-isomerase-expressing *Saccharomyces cerevisiae* strain for rapid anaerobic xylose fermentation. Fems Yeast Research 5:399-409

Kuyper M, Toirkens M J, Diderich J A, Winkler A A, Van Dijken J P, Pronk J T (2005b) Evolutionary engineering of mixed-sugar utilization by a xylose-fermenting *Saccharomyces cerevisiae* strain. Fems Yeast Research 5:925-934

Sambrook, K., Fritsch, E. F. and Maniatis, I. (1989) Molecular Cloning: A Laboratory Manual, 2nd edn. Cold Spring Harbor Laboratory Press, Cold Spring Harbor, N.Y.

Van Urk H, Mak P R, Scheffers W A, Van Dijken J P (1988) Metabolic responses of *Saccharomyces cerevisiae* CBS 8066 and *Candida utilis* CBS 621 upon transition from glucose limitation to glucose excess. Yeast 4:283-291

Verduyn C, Postma E, Scheffers W A, Van Dijken J P (1990) Physiology of *Saccharomyces cerevisiae* in anaerobic glucose-limited chemostat cultures. J Gen Microbiol 136:395-403

Verduyn C, Postma E, Scheffers W A, Van Dijken J P (1992) Effect of benzoic acid on metabolic fluxes in yeasts: a continuous-culture study on the regulation of respiration and alcoholic fermentation. Yeast 8:501-517

Weusthuis R A, Visser W, Pronk J T, Scheffers W A, Van Dijken J P (1994) Effects of oxygen limitation on sugar metabolism in yeasts—a continuous-culture study of the Kluyver effect. Microbiology 140:703-715

The invention claimed is:

1. A eukaryotic cell capable of expressing the following nucleotide sequences, wherein the expression of these nucleotide sequences confers on the cell the ability to use L-arabinose and/or to convert L-arabinose into L-ribulose, and/or xylulose 5-phosphate and/or into a desired fermentation product:
   (a) a nucleotide sequence encoding an arabinose isomerase (araA), wherein said nucleotide sequence is selected from the group consisting of:
      i. nucleotide sequences encoding an araA, said araA comprising an amino acid sequence that has at least 90% sequence identity with the amino acid sequence of SEQ ID NO:1,
      ii. nucleotide sequences comprising a nucleotide sequence that has at least 90% sequence identity with the nucleotide sequence of SEQ ID NO:2,
      iii. nucleotide sequences the complementary strand of which hybridizes to a nucleic acid molecule of sequence of (i) or (ii) under moderate conditions;
   (b) a nucleotide sequence encoding a L-ribulokinase (araB), wherein said nucleotide sequence is selected from the group consisting of:
      i. nucleotide sequences encoding an araB, said araB comprising an amino acid sequence that has at least 90% sequence identity with the amino acid sequence of SEQ ID NO:3,
      ii. nucleotide sequences comprising a nucleotide sequence that has at least 90% sequence identity with the nucleotide sequence of SEQ ID NO:4,
      iii. nucleotide sequences the complementary strand of which hybridizes to a nucleic acid molecule of sequence of (i) or (ii) under moderate conditions;
   (c) a nucleotide sequence encoding an L-ribulose-5-P-4-epimerase (araD), wherein said nucleotide sequence is selected from the group consisting of:
      i. nucleotide sequences encoding an araD, said araD comprising an amino acid sequence that has at least 90% sequence identity with the amino acid sequence of SEQ ID NO:5,
      ii. nucleotide sequences comprising a nucleotide sequence that has at least 90% sequence identity with the nucleotide sequence of SEQ ID NO:6,
      iii. nucleotide sequences the complementary strand of which hybridizes to a nucleic acid molecule of sequence of (i) or (ii) under moderate conditions;
   wherein moderate conditions is defined as conditions that allow a nucleic acid sequences of at least 50 nucleotides to hybridize at a temperature of about 45° C. in a solution comprising about 1 M salt and washing at room temperature in a solution comprising about 1 M salt.

2. A cell according to claim 1, wherein one, two or three of the araA, araB and araD nucleotide sequences originate from a *Lactobacillus* genus, optionally a *Lactobacillus plantarum* species.

3. A cell according to claim 1, wherein the cell is a yeast cell, optionally belonging to one of the genera: *Saccharomyces, Kluyveromyces, Candida, Pichia, Schizosaccharomyces, Hansenula, Kloeckera, Schwanniomyces* or *Yarrowia*.

4. A cell according to claim 3, wherein the yeast cell belongs to one of the species: *S. cerevisiae, S. bulderi, S. barnetti, S. exiguus, S. uvarum, S. diastaticus, K. lactis, K. marxianus* or *K. fragilis*.

5. A cell according to claim 1, wherein the nucleotide sequences encoding the araA, araB and/or araD are operably linked to a promoter that causes sufficient expression of the corresponding nucleotide sequences in the cell to confer to the cell the ability to use L-arabinose and/or to convert L-arabinose into L-ribulose, and/or xylulose 5-phosphate and/or into a desired fermentation product.

6. A cell according to claim 1, wherein the cell exhibits the ability to directly isomerise xylose into xylulose.

7. A cell according to claim 6, wherein the cell comprises a genetic modification that increases the flux of the pentose phosphate pathway.

8. A cell according to claim 6, wherein the genetic modification comprises overexpression of at least one gene of the non-oxidative part of the pentose phosphate pathway.

9. A cell according to claim 8, wherein the gene is selected from the group consisting of the genes encoding ribulose-5-phosphate isomerase, ribulose-5-phosphate epimerase, transketolase and transaldolase.

10. A cell according to claim 8, wherein the genetic modification comprises overexpression of at least the genes coding for a transketolase and a transaldolase.

11. A cell according to claim 8, wherein the cell further comprises a genetic modification that increases the specific xylulose kinase activity.

12. A cell according to claim 11, wherein the genetic modification comprises overexpression of a gene encoding a xylulose kinase.

13. A cell according to claim 8, wherein the gene that is overexpressed is endogenous to the cell.

14. A cell according to claim 5, wherein the cell comprises a genetic modification that reduces unspecific aldose reductase activity in the cell.

15. A cell according to claim 14, wherein the genetic modification reduces the expression of, or inactivates a gene encoding an unspecific aldose reductase.

16. A cell according to claim 15, wherein the gene is inactivated by deletion of at least part of the gene or by disruption of the gene.

17. A cell according to claim 14, wherein the expression of each gene in the cell that encodes an unspecific aldose reductase is reduced or inactivated.

18. A cell according to claim 1, wherein the fermentation product is selected from the group consisting of ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin.

19. A nucleic acid construct comprising a nucleic acid sequence encoding an araA, a nucleic acid sequence encoding an araB and/or a nucleic acid sequence encoding an araD all as defined in claim 1.

20. A process for producing a fermentation product selected from the group consisting of ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin, whereby the process comprises:
   (a) fermenting a medium containing a source of arabinose and optionally xylose with a modified cell as defined in claim 1, whereby the cell ferments arabinose and optionally xylose to the fermentation product; and optionally,
   (b) recovering the fermentation product.

21. A process for producing a fermentation product selected from the group consisting of ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin, wherein the process comprises:

(a) fermenting a medium containing at least a source of L-arabinose and a source of xylose with a cell as defined in claim 1 and a cell able to use xylose and/or exhibiting the ability to directly isomerise xylose into xylulose, whereby each cell ferments L-arabinose and/or xylose to the fermentation product; and optionally, (b) recovering the fermentation product.

22. A process according to claim 20, wherein the medium also contains a source of glucose.

23. A process according to claim 20, wherein the fermentation product is ethanol.

24. A process according to claim 23, wherein the volumetric ethanol productivity is at least 0.5 g ethanol per liter per hour.

25. A process according to claim 23, wherein the ethanol yield is at least 30%.

26. A process according to claim 20, wherein the process is anaerobic.

27. A process according to claim 20, wherein the process is aerobic, preferably performed under oxygen limited conditions.

* * * * *

SEQUENCE LISTING

<160> NUMBER OF SEQ ID NOS: 53

<210> SEQ ID NO 1
<211> LENGTH: 474
<212> TYPE: PRT
<213> ORGANISM: Lactobacillus plantarum

<400> SEQUENCE: 1

```
Met Leu Ser Val Pro Asp Tyr Glu Phe Trp Phe Val Thr Gly Ser Gln
1               5                   10                  15

His Leu Tyr Gly Glu Glu Gln Leu Lys Ser Val Ala Lys Asp Ala Gln
            20                  25                  30

Asp Ile Ala Asp Lys Leu Asn Ala Ser Gly Lys Leu Pro Tyr Lys Val
        35                  40                  45

Val Phe Lys Asp Val Met Thr Thr Ala Glu Ser Ile Thr Asn Phe Met
    50                  55                  60

Lys Glu Val Asn Tyr Asn Asp Lys Val Ala Gly Val Ile Thr Trp Met
65                  70                  75                  80

His Thr Phe Ser Pro Ala Lys Asn Trp Ile Arg Gly Thr Glu Leu Leu
                85                  90                  95

Gln Lys Pro Leu Leu His Leu Ala Thr Gln Tyr Leu Asn Asn Ile Pro
            100                 105                 110

Tyr Ala Asp Ile Asp Phe Asp Tyr Met Asn Leu Asn Gln Ser Ala His
        115                 120                 125

Gly Asp Arg Glu Tyr Ala Tyr Ile Asn Ala Arg Leu Gln Lys His Asn
    130                 135                 140

Lys Ile Val Tyr Gly Tyr Trp Gly Asp Glu Asp Val Gln Glu Gln Ile
145                 150                 155                 160

Ala Arg Trp Glu Asp Val Ala Val Ala Tyr Asn Glu Ser Phe Lys Val
                165                 170                 175

Lys Val Ala Arg Phe Gly Asp Thr Met Arg Asn Val Ala Val Thr Glu
            180                 185                 190

Gly Asp Lys Val Glu Ala Gln Ile Lys Met Gly Trp Thr Val Asp Tyr
        195                 200                 205

Tyr Gly Ile Gly Asp Leu Val Glu Glu Ile Asn Lys Val Ser Asp Ala
    210                 215                 220

Asp Val Asp Lys Glu Tyr Ala Asp Leu Glu Ser Arg Tyr Glu Met Val
225                 230                 235                 240

Gln Val Asp Asn Asp Ala Asp Thr Tyr Lys His Ser Val Arg Val Gln
                245                 250                 255

Leu Ala Gln Tyr Leu Gly Ile Lys Arg Phe Leu Glu Arg Gly Gly Tyr
            260                 265                 270

Thr Ala Phe Thr Thr Asn Phe Glu Asp Leu Trp Gly Met Glu Gln Leu
        275                 280                 285

Pro Gly Leu Ala Ser Gln Leu Leu Ile Arg Asp Gly Tyr Gly Phe Gly
    290                 295                 300

Ala Glu Gly Asp Trp Lys Thr Ala Ala Leu Gly Arg Val Met Lys Ile
305                 310                 315                 320

Met Ser His Asn Lys Gln Thr Ala Phe Met Glu Asp Tyr Thr Leu Asp
                325                 330                 335

Leu Arg His Gly His Glu Ala Ile Leu Gly Ser His Met Leu Glu Val
            340                 345                 350

Asp Pro Ser Ile Ala Ser Asp Lys Pro Arg Val Glu Val His Pro Leu
        355                 360                 365
```

```
Asp Ile Gly Gly Lys Asp Asp Pro Ala Arg Leu Val Phe Thr Gly Ser
    370                 375                 380

Glu Gly Glu Ala Ile Asp Val Thr Val Ala Asp Phe Arg Asp Gly Phe
385                 390                 395                 400

Lys Met Ile Ser Tyr Ala Val Asp Ala Asn Lys Pro Glu Ala Glu Thr
                405                 410                 415

Pro Asn Leu Pro Val Ala Lys Gln Leu Trp Thr Pro Lys Met Gly Leu
            420                 425                 430

Lys Lys Gly Ala Leu Glu Trp Met Gln Ala Gly Gly His His Thr
        435                 440                 445

Met Leu Ser Phe Ser Leu Thr Glu Glu Gln Met Glu Asp Tyr Ala Thr
    450                 455                 460

Met Val Gly Met Thr Lys Ala Phe Leu Lys
465                 470

<210> SEQ ID NO 2
<211> LENGTH: 1425
<212> TYPE: DNA
<213> ORGANISM: Lactobacillus plantarum

<400> SEQUENCE: 2
atgttatcag tacctgatta tgagttttgg tttgttaccg gttcacaaca ccttatggt      60 gaagaacaat tgaagtctgt tgctaaggat gcgcaagata ttgcggataa attgaatgca    120
agcggcaagt taccttataa agtagtcttt aaggatgtta tgacgacggc tgaaagtatc    180
accaacttta tgaaagaagt taattacaat gataaggtag ccggtgttat tacttggatg    240
cacacattct caccagctaa gaactggatt cgtggaactg aactgttaca aaaaccatta    300
ttacacttag caacgcaata tttgaataat attccatatg cagacattga ctttgattac    360
atgaacctta ccaaagtgcc catggcgacc gcgagtatgc ctacattaac gcccggttg    420 cagaaacata taagattgtt ttacggctat tggggcgatg aagatgtgca agagcagatt    480
gcacgttggg aagacgtcgc cgtagcgtac aatgagagct ttaaagttaa ggttgctcgc    540
tttggcgaca caatgcgtaa tgtggccgtt actgaaggtg acaaggttga agctcaaatt    600
aagatgggct ggacagttga ctattatggt atcggtgact tagttgaaga gatcaataag    660
gtttcggatg ctgatgttga taaggaatac gctgacttgg agtctcggta tgaaatggtc    720
caagttgata cgatgcgga cacgtataaa cattcagttc gggttcaatt ggcacaatat    780
ctgggtatta gcggttctt agaaagaggc ggttacacag cctttaccac gaactttgaa    840
gatctttggg gatggagca attacctggt ctagcttcac aattattaat tcgtgatggg    900
tatggttttg gtgctgaagg tgactggaag acggctgctt taggacgggt tatgaagatt    960
atgtctcaca acaagcaaac cgcctttatg gaagactaca cgttagactt gcgtcatggt   1020
catgaagcga tcttaggttc acacatgttg gaagttgatc cgtctatcgc aagtgataaa   1080
ccacgggtcg aagttcatcc attggatatt gggggtaaag atgatcctgc tcgcctagta   1140
tttactggtt cagaaggtga agcaattgat gtcaccgttg ccgatttccg tgatgggttc   1200
aagatgatta gctacgcggt agatgcgaat aagccagaag ccgaaacacc taatttacca   1260
gttgctaagc aattatggac cccaaagatg ggcttgaaga agggtgcact agaatggatg   1320
caagctggtg gtggtcacca cacgatgctg tccttctcgt taactgaaga acaaatggaa   1380
gactatgcaa ccatggttgg catgactaag gcattcttaa agtaa               1425

<210> SEQ ID NO 3
```

<211> LENGTH: 533
<212> TYPE: PRT
<213> ORGANISM: Lactobacillus plantarum

<400> SEQUENCE: 3

```
Met Asn Leu Val Glu Thr Ala Gln Ala Ile Lys Thr Gly Lys Val Ser
1               5                   10                  15

Leu Gly Ile Glu Leu Gly Ser Thr Arg Ile Lys Ala Val Leu Ile Thr
            20                  25                  30

Asp Asp Phe Asn Thr Ile Ala Ser Gly Ser Tyr Val Trp Glu Asn Gln
        35                  40                  45

Phe Val Asp Gly Thr Trp Thr Tyr Ala Leu Glu Asp Val Trp Thr Gly
    50                  55                  60

Ile Gln Gln Ser Tyr Thr Gln Leu Ala Ala Asp Val Arg Ser Lys Tyr
65                  70                  75                  80

His Met Ser Leu Lys His Ile Asn Ala Ile Gly Ile Ser Ala Met Met
                85                  90                  95

His Gly Tyr Leu Ala Phe Asp Gln Gln Ala Lys Leu Leu Val Pro Phe
            100                 105                 110

Arg Thr Trp Arg Asn Asn Ile Thr Gly Gln Ala Ala Asp Glu Leu Thr
        115                 120                 125

Glu Leu Phe Asp Phe Asn Ile Pro Gln Arg Trp Ser Ile Ala His Leu
    130                 135                 140

Tyr Gln Ala Ile Leu Asn Asn Glu Ala His Val Lys Gln Val Asp Phe
145                 150                 155                 160

Ile Thr Thr Leu Ala Gly Tyr Val Thr Trp Lys Leu Ser Gly Glu Lys
                165                 170                 175

Val Leu Gly Ile Gly Asp Ala Ser Gly Val Phe Pro Ile Asp Glu Thr
            180                 185                 190

Thr Asp Thr Tyr Asn Gln Thr Met Leu Thr Lys Phe Ser Gln Leu Asp
        195                 200                 205

Lys Val Lys Pro Tyr Ser Trp Asp Ile Arg His Ile Leu Pro Arg Val
    210                 215                 220

Leu Pro Ala Gly Ala Ile Ala Gly Lys Leu Thr Ala Ala Gly Ala Ser
225                 230                 235                 240

Leu Leu Asp Gln Ser Gly Thr Leu Asp Ala Gly Ser Val Ile Ala Pro
                245                 250                 255

Pro Glu Gly Asp Ala Gly Thr Gly Met Val Gly Thr Asn Ser Val Arg
            260                 265                 270

Lys Arg Thr Gly Asn Ile Ser Val Gly Thr Ser Ala Phe Ser Met Asn
        275                 280                 285

Val Leu Asp Lys Pro Leu Ser Lys Val Tyr Arg Asp Ile Asp Ile Val
    290                 295                 300

Met Thr Pro Asp Gly Ser Pro Val Ala Met Val His Val Asn Asn Cys
305                 310                 315                 320

Ser Ser Asp Ile Asn Ala Trp Ala Thr Ile Phe Arg Glu Phe Ala Ala
                325                 330                 335

Arg Leu Gly Met Glu Leu Lys Pro Asp Arg Leu Tyr Glu Thr Leu Phe
            340                 345                 350

Leu Glu Ser Thr Arg Ala Asp Ala Asp Ala Gly Leu Ala Asn Tyr
        355                 360                 365

Ser Tyr Gln Ser Gly Glu Asn Ile Thr Lys Ile Gln Ala Gly Arg Pro
    370                 375                 380

Leu Phe Val Arg Thr Pro Asn Ser Lys Phe Ser Leu Pro Asn Phe Met
```

```
                385                 390                 395                 400
Leu Thr Gln Leu Tyr Ala Ala Phe Ala Pro Leu Gln Leu Gly Met Asp
                405                 410                 415

Ile Leu Val Asn Glu Glu His Val Gln Thr Asp Val Met Ile Ala Gln
                420                 425                 430

Gly Gly Leu Phe Arg Thr Pro Val Ile Gly Gln Val Leu Ala Asn
                435                 440                 445

Ala Leu Asn Ile Pro Ile Thr Val Met Ser Thr Ala Gly Glu Gly Gly
            450                 455                 460

Pro Trp Gly Met Ala Val Leu Ala Asn Phe Ala Cys Arg Gln Thr Ala
465                 470                 475                 480

Met Asn Leu Glu Asp Phe Leu Asp Gln Glu Val Phe Lys Glu Pro Glu
                485                 490                 495

Ser Met Thr Leu Ser Pro Glu Pro Glu Arg Val Ala Gly Tyr Arg Glu
                500                 505                 510

Phe Ile Gln Arg Tyr Gln Ala Gly Leu Pro Val Glu Ala Ala Gly
                515                 520                 525

Gln Ala Ile Lys Tyr
            530

<210> SEQ ID NO 4
<211> LENGTH: 1602
<212> TYPE: DNA
<213> ORGANISM: Lactobacillus plantarum

<400> SEQUENCE: 4
atgaatttag ttgaaacagc ccaagcgatt aaaactggca agtttctttt aggaattgag      60
cttggctcaa ctcgaattaa agccgttttg atcacggacg attttaatac gattgcttcg     120
ggaagttacg tttgggaaaa ccaatttgtt gatggtactt ggacttacgc acttgaagat     180
gtctggaccg gaattcaaca agttatacg caattagcag cagatgtccg cagtaaaatat     240 cacatgagtt tgaagcatat caatgctatt ggcattagtg ccatgatgca cggataccta     300
gcatttgatc aacaagcgaa attattagtt ccgtttcgga cttggcgtaa taacattacg     360
gggcaagcag cagatgaatt gaccgaatta tttgatttca acattccaca acggtggagt     420
atcgcgcact ataccaggc aatcttaaat aatgaagcgc acgttaaaca ggtggacttc     480
ataacaacgc tggctggcta tgtaacctgg aaattgtcgg gtgagaaagt tctaggaatc     540
ggtgatgcgt ctggcgtttt cccaattgat gaaacgactg acacatacaa tcagacgatg     600
ttaaccaagt ttagccaact tgacaaagtt aaaccgtatt catgggatat ccggcatatt     660
ttaccgcggg ttttaccagc gggagccatt gctggaaagt taacggctgc cggggcgagc     720
ttacttgatc agagcggcac gctcgacgct ggcagtgtta ttgcaccgcc agaaggggat     780
gctggaacag gaatggtcgg tacgaacagc gtccgtaaac gcacgggtaa catctcggtg     840
ggaacctcag catttttcgat gaacgttcta gataaaccat tgtctaaagt ctatcgcgat     900
attgatattg ttatgacgcc agatgggtca ccagttgcaa tggtgcatgt taataattgt     960
tcatcagata ttaatgcgtg ggcaacgatt tttcgtgagt ttgcagcccg gttgggaatg    1020
gaattgaaac cggatcgatt atatgaaacg ttattcttgg aatcaactcg cgctgatgcg    1080
gatgctggag ggttggctaa ttatagttat caatccggtg agaatattac taagattcaa    1140
gctggtcggc cgctatttgt acggacacca aacagtaaat ttagtttacc gaactttatg    1200
ttgacccaat tatatgcggc gttcgcaccc ctccaacttg gtatggatat tcttgttaac    1260
```

```
gaagaacatg ttcaaacgga cgttatgatt gcacagggtg gattgttccg aacgccggta    1320
attggccaac aagtattggc caacgcactg aacattccga ttactgtaat gagtactgct    1380
ggtgaaggcg gcccatgggg gatggcagtg ttagccaact ttgcttgtcg gcaaactgca    1440
atgaacctag aagatttctt agatcaagaa gtctttaaag agccagaaag tatgacgttg    1500
agtccagaac cggaacgggt ggccggatat cgtgaattta ttcaacgtta tcaagctggc    1560
ttaccagttg aagcagcggc tgggcaagca atcaaatatt ag                      1602
```

<210> SEQ ID NO 5
<211> LENGTH: 242
<212> TYPE: PRT
<213> ORGANISM: Lactobacillus plantarum

<400> SEQUENCE: 5

```
Met Leu Glu Ala Leu Lys Gln Glu Val Tyr Glu Ala Asn Met Gln Leu
1               5                   10                  15

Pro Lys Leu Gly Leu Val Thr Phe Thr Trp Gly Asn Val Ser Gly Ile
            20                  25                  30

Asp Arg Glu Lys Gly Leu Phe Val Ile Lys Pro Ser Gly Val Asp Tyr
        35                  40                  45

Gly Glu Leu Lys Pro Ser Asp Leu Val Val Asn Leu Gln Gly Glu
    50                  55                  60

Val Val Glu Gly Lys Leu Asn Pro Ser Asp Thr Pro Thr His Thr
65                  70                  75                  80

Val Leu Tyr Asn Ala Phe Pro Asn Ile Gly Gly Ile Val His Thr His
                85                  90                  95

Ser Pro Trp Ala Val Ala Tyr Ala Ala Ala Gln Met Asp Val Pro Ala
            100                 105                 110

Met Asn Thr Thr His Ala Asp Thr Phe Tyr Gly Asp Val Pro Ala Ala
        115                 120                 125

Asp Ala Leu Thr Lys Glu Glu Ile Glu Ala Asp Tyr Glu Gly Asn Thr
    130                 135                 140

Gly Lys Thr Ile Val Lys Thr Phe Gln Glu Arg Gly Leu Asp Tyr Glu
145                 150                 155                 160

Ala Val Pro Ala Ser Leu Val Ser Gln His Gly Pro Phe Ala Trp Gly
                165                 170                 175

Pro Thr Pro Ala Lys Ala Val Tyr Asn Ala Lys Val Leu Glu Val Val
            180                 185                 190

Ala Glu Glu Asp Tyr His Thr Ala Gln Leu Thr Arg Ala Ser Ser Glu
        195                 200                 205

Leu Pro Gln Tyr Leu Leu Asp Lys His Tyr Leu Arg Lys His Gly Ala
    210                 215                 220

Ser Ala Tyr Tyr Gly Gln Asn Asn Ala His Ser Lys Asp His Ala Val
225                 230                 235                 240

Arg Lys
```

<210> SEQ ID NO 6
<211> LENGTH: 729
<212> TYPE: DNA
<213> ORGANISM: Lactobacillus plantarum

<400> SEQUENCE: 6

```
atgctagaag cattaaaaca agaagtttat gaggctaaca tgcagcttcc aaagctgggc    60
ctggttactt ttacctgggg caatgtctcg ggcattgacc gggaaaaagg cctattcgtg    120
```

```
atcaagccat ctggtgttga ttatggtgaa ttaaaaccaa gcgatttagt cgttgttaac    180
ttacagggtg aagtggttga aggtaaacta aatccgtcta gtgatacgcc gactcatacg    240
gtgttatata acgcttttcc taatattggc ggaattgtcc atactcattc gccatgggca    300
gttgcctatg cagctgctca aatggatgtg ccagctatga acacgaccca tgctgatacg    360
ttctatggtg acgtgccggc cgcggatgcg ctgactaagg aagaaattga agcagattat    420
gaaggcaaca cgggtaaaac cattgtgaag acgttccaag aacggggcct cgattatgaa    480
gctgtaccag cctcattagt cagccagcac ggcccatttg cttggggacc aacgccagct    540
aaagccgttt acaatgctaa agtgttggaa gtggttgccg aagaagatta tcatactgcg    600
caattgaccc gtgcaagtag cgaattacca caatatttat tagataagca ttatttacgt    660
aagcatggtg caagtgccta ttatggtcaa aataatgcgc attctaagga tcatgcagtt    720
cgcaagtaa                                                              729
```

<210> SEQ ID NO 7
<211> LENGTH: 437
<212> TYPE: PRT
<213> ORGANISM: Piromyces sp.

<400> SEQUENCE: 7

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
```

```
                260             265             270
Ala Thr Leu Ala Gly His Thr Phe Glu His Glu Leu Ala Cys Ala Val
            275                 280                 285

Asp Ala Gly Met Leu Gly Ser Ile Asp Ala Asn Arg Gly Asp Tyr Gln
        290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
385                 390                 395                 400

Asp Gly Lys Leu Thr Leu Glu Gln Val Tyr Glu Tyr Gly Lys Lys Asn
            405                 410                 415

Gly Glu Pro Lys Gln Thr Ser Gly Lys Gln Glu Leu Tyr Glu Ala Ile
        420                 425                 430

Val Ala Met Tyr Gln
        435

<210> SEQ ID NO 8
<211> LENGTH: 1669
<212> TYPE: DNA
<213> ORGANISM: Piromyces sp.

<400> SEQUENCE: 8
gtaaatggct aaggaatatt tcccacaaat tcaaaagatt aagttcgaag gtaaggattc      60
taagaatcca ttagccttcc actactacga tgctgaaaag gaagtcatgg gtaagaaaat     120
gaaggattgg ttacgtttcg ccatggcctg gtggcacact cttcgcgccg aaggtgctga     180
ccaattcggt ggaggtacaa agtctttccc atggaacgaa ggtactgatg ctattgaaat     240
tgccaagcaa aaggttgatg ctggtttcga aatcatgcaa aagcttggta ttccatacta     300
ctgtttccac gatgttgatc ttgtttccga aggtaactct attgaagaat acgaatccaa     360
ccttaaggct gtcgttgctt acctcaagga aaagcaaaag gaaaccggta ttaagcttct     420
ctggagtact gctaacgtct tcggtcacaa gcgttacatg aacggtgcct ccactaaccc     480
agactttgat gttgtcgccc gtgctattgt tcaaattaag aacgccatag acgccggtat     540
tgaacttggt gctgaaaact acgtcttctg gggtggtcgt gaaggttaca tgagtctcct     600
taacactgac caaaagcgtg aaaaggaaca catggccact atgcttacca tggctcgtga     660
ctacgctcgt tccaagggat tcaagggtac tttcctcatt gaaccaaagc caatggaacc     720
aaccaagcac caatacgatg ttgacactga accgctatt ggtttcctta aggcccacaa     780
cttagacaag gacttcaagg tcaacattga agttaaccac gctactcttg ctggtcacac     840
tttcgaacac gaacttgcct gtgctgttga tgctggtatg ctcggttcca ttgatgctaa     900
ccgtggtgac taccaaaacg gttgggatac tgatcaattc ccaattgatc aatacgaact     960
cgtccaagct ggatggaaa tcatccgtgg tggtggtttc gttactggtg gtaccaactt    1020
cgatgccaag actcgtcgta actctactga cctcgaagac atcatcattg cccacgtttc    1080
```

```
tggtatggat gctatggctc gtgctcttga aaacgctgcc aagctcctcc aagaatctcc    1140
atacaccaag atgaagaagg aacgttacgc ttccttcgac agtggtattg gtaaggactt    1200
tgaagatggt aagctcaccc tcgaacaagt ttacgaatac ggtaagaaga acggtgaacc    1260
aaagcaaact tctggtaagc aagaactcta cgaagctatt gttgccatgt accaataagt    1320
taatcgtagt taaattggta aataattgt aaaatcaata aacttgtcaa tcctccaatc    1380
aagtttaaaa gatcctatct ctgtactaat taaatatagt acaaaaaaaa atgtataaac    1440 aaaaaaagt ctaaaagacg aagaattta atttagggaa aaaataaaaa taataataaa    1500
caatagataa atcctttata ttaggaaaat gtcccattgt attattttca tttctactaa    1560
aaaagaaagt aaataaaaca caagaggaaa ttttccctttt tttttttttt tgtaataaat    1620
tttatgcaaa tataaatata aataaaataa taaaaaaaaa aaaaaaaa                 1669
```

<210> SEQ ID NO 9
<211> LENGTH: 496
<212> TYPE: PRT
<213> ORGANISM: Bacillus subtilis

<400> SEQUENCE: 9

```
Met Leu Gln Thr Lys Asp Tyr Glu Phe Trp Phe Val Thr Gly Ser Gln
1               5                   10                  15

His Leu Tyr Gly Glu Glu Thr Leu Glu Leu Val Asp Gln His Ala Lys
            20                  25                  30

Ser Ile Cys Glu Gly Leu Ser Gly Ile Ser Ser Arg Tyr Lys Ile Thr
        35                  40                  45

His Lys Pro Val Val Thr Ser Pro Glu Thr Ile Arg Glu Leu Leu Arg
    50                  55                  60

Glu Ala Glu Tyr Ser Glu Thr Cys Ala Gly Ile Ile Thr Trp Met His
65                  70                  75                  80

Thr Phe Ser Pro Ala Lys Met Trp Ile Glu Gly Leu Ser Ser Tyr Gln
                85                  90                  95

Lys Pro Leu Met His Leu His Thr Gln Tyr Asn Arg Asp Ile Pro Trp
            100                 105                 110

Gly Thr Ile Asp Met Asp Phe Met Asn Ser Asn Gln Ser Ala His Gly
        115                 120                 125

Asp Arg Glu Tyr Gly Tyr Ile Asn Ser Arg Met Gly Leu Ser Arg Lys
    130                 135                 140

Val Ile Ala Gly Tyr Trp Asp Asp Glu Glu Val Lys Lys Glu Met Ser
145                 150                 155                 160

Gln Trp Met Asp Thr Ala Ala Ala Leu Asn Glu Ser Arg His Ile Lys
                165                 170                 175

Val Ala Arg Phe Gly Asp Asn Met Arg His Val Ala Val Thr Asp Gly
            180                 185                 190

Asp Lys Val Gly Ala His Ile Gln Phe Gly Trp Gln Val Asp Gly Tyr
        195                 200                 205

Gly Ile Gly Asp Leu Val Glu Val Met Asp Arg Ile Thr Asp Asp Glu
    210                 215                 220

Val Asp Thr Leu Tyr Ala Glu Tyr Asp Arg Leu Tyr Val Ile Ser Glu
225                 230                 235                 240

Glu Thr Lys Arg Asp Glu Ala Lys Val Ala Ser Ile Lys Glu Gln Ala
                245                 250                 255

Lys Ile Glu Leu Gly Leu Thr Ala Phe Leu Glu Gln Gly Gly Tyr Thr
            260                 265                 270
```

| | | | | | | | | | | | | | | |
|---|---|---|---|---|---|---|---|---|---|---|---|---|---|---|
|Ala|Phe|Thr|Thr|Ser|Phe|Glu|Val|Leu|His|Gly|Met|Lys|Gln|Leu|Pro|
| | |275| | | |280| | | |285| | | | |

Ala Phe Thr Thr Ser Phe Glu Val Leu His Gly Met Lys Gln Leu Pro
            275                 280                 285

Gly Leu Ala Val Gln Arg Leu Met Glu Lys Gly Tyr Gly Phe Ala Gly
            290                 295                 300

Glu Gly Asp Trp Lys Thr Ala Ala Leu Val Arg Met Met Lys Ile Met
305                 310                 315                 320

Ala Lys Gly Lys Arg Thr Ser Phe Met Glu Asp Tyr Thr Tyr His Phe
                325                 330                 335

Glu Pro Gly Asn Glu Met Ile Leu Gly Ser His Met Leu Glu Val Cys
            340                 345                 350

Pro Thr Val Ala Leu Asp Gln Pro Lys Ile Glu Val His Ser Leu Ser
            355                 360                 365

Ile Gly Gly Lys Glu Asp Pro Ala Arg Leu Val Phe Asn Gly Ile Ser
            370                 375                 380

Gly Ser Ala Ile Gln Ala Ser Ile Val Asp Ile Gly Gly Arg Phe Arg
385                 390                 395                 400

Leu Val Leu Asn Glu Val Asn Gly Gln Glu Ile Glu Lys Asp Met Pro
                405                 410                 415

Asn Leu Pro Val Ala Arg Val Leu Trp Lys Pro Glu Pro Ser Leu Lys
            420                 425                 430

Thr Ala Ala Glu Ala Trp Ile Leu Ala Gly Gly Ala His His Thr Cys
            435                 440                 445

Leu Ser Tyr Glu Leu Thr Ala Glu Gln Met Leu Asp Trp Ala Glu Met
            450                 455                 460

Ala Gly Ile Glu Ser Val Leu Ile Ser Arg Asp Thr Thr Ile His Lys
465                 470                 475                 480

Leu Lys His Glu Leu Lys Trp Asn Glu Ala Leu Tyr Arg Leu Gln Lys
                485                 490                 495

<210> SEQ ID NO 10
<211> LENGTH: 1511
<212> TYPE: DNA
<213> ORGANISM: Bacillus subtilis

<400> SEQUENCE: 10

| | |
|---|---|
|atgagaaagg ggcagtttac atgcttcaga caaaggatta tgaattctgg tttgtgacag|60|
|gaagccagca cctatacggg gaagagacgc tggaactcgt agatcagcat gctaaaagca|120|
|tttgtgaggg gctcagcggg atttcttcca gatataaaat cactcataag cccgtcgtca|180|
|cttcaccgga aaccattaga gagctgttaa gagaagcgga gtacagtgag acatgtgctg|240|
|gcatcattac atggatgcac acattttccc ctgcaaaaat gtggatagaa ggccttttcct|300|
|cttatcaaaa accgcttatg catttgcata cccaatataa tcgcgatatc ccgtggggta|360|
|cgattgacat ggatttttatg aacagcaacc aatccgcgca tggcgatcga gagtacggtt|420|
|acatcaactc gagaatgggg cttagccgaa aagtcattgc cggctattgg atgatgaag|480|
|aagtgaaaaa agaaatgtcc cagtggatgg atacggcggc tgcattaaat gaaagcagac|540|
|atattaaggt tgccagattt ggagataaca tgcgtcatgt cgcggtaacg gacggagaca|600|
|aggtgggagc gcatattcaa tttggctggc aggttgacgg atatggcatc ggggatctcg|660|
|ttgaagtgat ggatcgcatt acggacgacg aggttgacac gctttatgcc gagtatgaca|720|
|gactatatgt gatcagtgag gaaacaaaac gtgacgaagc aaaggtagcg tccattaaag|780|
|aacaggcgaa aattgaactt ggattaaccg ctttttcttga gcaaggcgga tacacagcgt|840|
|ttacgacatc gtttgaagtg ctgcacggaa tgaaacagct gccgggactt gccgttcagc|900|

```
gcctgatgga gaaaggctat gggtttgccg gtgaaggaga ttggaagaca gcggcccttg    960
tacggatgat gaaaatcatg gctaaaggaa aagaacttc cttcatggaa gattacacgt    1020
accattttga accgggaaat gaaatgattc tgggctctca catgcttgaa gtgtgtccga    1080
ctgtcgcttt ggatcagccg aaaatcgagg ttcattcgct ttcgattggc ggcaaagagg    1140
accctgcgcg tttggtattt aacggcatca gcggttctgc cattcaagct agcattgttg    1200
atattggcgg gcgtttccgc cttgtgctga atgaagtcaa cggccaggaa attgaaaaag    1260
acatgccgaa tttaccggtt gcccgtgttc tctggaagcc ggagccgtca ttgaaaacag    1320
cagcggaggc atggatttta gccggcggtg cacaccatac ctgcctgtct tatgaactga    1380
cagcggagca aatgcttgat tgggcggaaa tggcgggaat cgaaagtgtt ctcatttccc    1440
gtgatacgac aattcataaa ctgaaacacg agttaaaatg gaacgaggcg ctttaccggc    1500
ttcaaaagta g                                                        1511

<210> SEQ ID NO 11
<211> LENGTH: 566
<212> TYPE: PRT
<213> ORGANISM: Escherichia coli

<400> SEQUENCE: 11

Met Ala Ile Ala Ile Gly Leu Asp Phe Gly Ser Asp Ser Val Arg Ala
1               5                   10                  15

Leu Ala Val Asp Cys Ala Ser Gly Glu Glu Ile Ala Thr Ser Val Glu
                20                  25                  30

Trp Tyr Pro Arg Trp Gln Lys Gly Gln Phe Cys Asp Ala Pro Asn Asn
            35                  40                  45

Gln Phe Arg His His Pro Arg Asp Tyr Ile Glu Ser Met Glu Ala Ala
        50                  55                  60

Leu Lys Thr Val Leu Ala Glu Leu Ser Val Glu Gln Arg Ala Ala Val
65                  70                  75                  80

Val Gly Ile Gly Val Asp Ser Thr Gly Ser Thr Pro Ala Pro Ile Asp
                85                  90                  95

Ala Asp Gly Asn Val Leu Ala Leu Arg Pro Glu Phe Ala Glu Asn Pro
            100                 105                 110

Asn Ala Met Phe Val Leu Trp Lys Asp His Thr Ala Val Glu Arg Ser
        115                 120                 125

Glu Glu Ile Thr Arg Leu Cys His Ala Pro Gly Asn Val Asp Tyr Ser
    130                 135                 140

Arg Tyr Ile Gly Gly Ile Tyr Ser Ser Glu Trp Phe Trp Ala Lys Ile
145                 150                 155                 160

Leu His Val Thr Arg Gln Asp Ser Ala Val Ala Gln Ser Ala Ala Ser
                165                 170                 175

Trp Ile Glu Leu Cys Asp Trp Val Pro Ala Leu Leu Ser Gly Thr Thr
            180                 185                 190

Arg Pro Gln Asp Ile Arg Arg Gly Arg Cys Ser Ala Gly His Lys Ser
        195                 200                 205

Leu Trp His Glu Ser Trp Gly Gly Leu Pro Pro Ala Ser Phe Phe Asp
    210                 215                 220

Glu Leu Asp Pro Ile Leu Asn Arg His Leu Pro Ser Pro Leu Phe Thr
225                 230                 235                 240

Asp Thr Trp Thr Ala Asp Ile Pro Val Gly Thr Leu Cys Pro Glu Trp
                245                 250                 255
```

Ala Gln Arg Leu Gly Leu Pro Glu Ser Val Val Ile Ser Gly Gly Ala
            260                 265                 270

Phe Asp Cys His Met Gly Ala Val Gly Ala Gly Ala Gln Pro Asn Ala
        275                 280                 285

Leu Val Lys Val Ile Gly Thr Ser Thr Cys Asp Ile Leu Ile Ala Asp
    290                 295                 300

Lys Gln Ser Val Gly Glu Arg Ala Val Lys Gly Ile Cys Gly Gln Val
305                 310                 315                 320

Asp Gly Ser Val Val Pro Gly Phe Ile Gly Leu Glu Ala Gly Gln Ser
                325                 330                 335

Ala Phe Gly Asp Ile Tyr Ala Trp Phe Gly Arg Val Leu Ser Trp Pro
            340                 345                 350

Leu Glu Gln Leu Ala Ala Gln His Pro Glu Leu Lys Ala Gln Ile Asn
        355                 360                 365

Ala Ser Gln Lys Gln Leu Leu Pro Ala Leu Thr Glu Ala Trp Ala Lys
    370                 375                 380

Asn Pro Ser Leu Asp His Leu Pro Val Val Leu Asp Trp Phe Asn Gly
385                 390                 395                 400

Arg Arg Ser Pro Asn Ala Asn Gln Arg Leu Lys Gly Val Ile Thr Asp
                405                 410                 415

Leu Asn Leu Ala Thr Asp Ala Pro Leu Leu Phe Gly Gly Leu Ile Ala
            420                 425                 430

Ala Thr Ala Phe Gly Ala Arg Ala Ile Met Glu Cys Phe Thr Asp Gln
        435                 440                 445

Gly Ile Ala Val Asn Asn Val Met Ala Leu Gly Gly Ile Ala Arg Lys
    450                 455                 460

Asn Gln Val Ile Met Gln Ala Cys Cys Asp Val Leu Asn Arg Pro Leu
465                 470                 475                 480

Gln Ile Val Ala Ser Asp Gln Cys Cys Ala Leu Gly Ala Ala Ile Phe
                485                 490                 495

Ala Ala Val Ala Ala Lys Val His Ala Asp Ile Pro Ser Ala Gln Gln
            500                 505                 510

Lys Met Ala Ser Ala Val Glu Lys Thr Leu Gln Pro Arg Ser Glu Gln
        515                 520                 525

Ala Gln Arg Phe Glu Gln Leu Tyr Arg Arg Tyr Gln Gln Trp Ala Met
    530                 535                 540

Ser Ala Glu Gln His Tyr Leu Pro Thr Ser Ala Pro Ala Gln Ala Ala
545                 550                 555                 560

Gln Ala Val Ala Thr Leu
            565

<210> SEQ ID NO 12
<211> LENGTH: 1453
<212> TYPE: DNA
<213> ORGANISM: Escherichia coli

<400> SEQUENCE: 12
atggcgattg caattggcct cgattttggc agtgattctg tgcgagcttt ggcggtggac      60
tgcgccagcg gtaagagat cgccaccagc gtagagtggt atccccgttg caaaaaggg     120 caattttgtg atgccccgaa taaccagttc cgtcatcatc cgcgtgacta cattgagtca     180
atggaagcgg cactgaaaac cgtgcttgca gagcttagcg tcgaacagcg cgcagctgtg     240
gtcgggattg gcgttgacag taccggctcg acgcccgcac cgattgatgc cgacggtaac     300
gtgctggcgc tgcgcccgga gtttgccgaa aacccgaacg cgatgttcgt attgtggaaa     360

```
gaccacactg cggttgaaag aagcgaagag attacccgtt tgtgccacgc gccgggcaat      420
gttgactact cccgctatat tggcggtatt tattccagcg aatggttctg ggcaaaaatc      480
ctgcatgtga ctcgccagga cagcgccgtg gcgcaatctg ccgcatcgtg gattgagctg      540
tgcgactggg tgccagctct gctttccggt accacccgcc cgcaggatat tcgtcgcgga      600
cgttgcagcg ccgggcataa atctctgtgg cacgaaagct ggggcggctt gccgccagcc      660
agtttctttg atgagctgga cccgatcctc aatcgccatt tgccttcccc gctgttcact      720
gacacctgga ctgccgatat tccggtgggc accttatgcc cggaatgggc gcagcgtctc      780
ggcctgcctg aaagcgtggt gatttccggc ggcgcgtttg actgccatat gggcgcagtt      840
ggcgcaggcg cacagcctaa cgcactggta aaagttatcg gtacttccac ctgcgacatt      900
ctgattgccg acaaacagag cgttggcgag cgggcagtta aaggtatttg cggtcaggtt      960
gatggcagcg tggtgcctgg atttatcggt ctggaagcag gccaatcggc gtttggtgat     1020
atctacgcct ggttcggtcg cgtactcagc tggccgctgg aacagcttgc cgcccagcat     1080
ccggaactga agcgcaaat caacgccagc cagaaacaac tgcttccggc gctgaccgaa     1140
gcatgggcca aaaatccgtc tctggatcac ctgccggtgg tgctcgactg gtttaacggt     1200
cgtcgctcgc caaacgctaa ccaacgcctg aaagggtga ttaccgatct taacctcgct     1260
accgacgctc cgctgctgtt cggcggtttg attgctgcca ccgcctttgg cgcacgcgca     1320
atcatggagt gctttaccga tcaggggatc gccgtcaata acgtgatggc gctgggcggc     1380
atcgcgcgga aaaccaagt cattatgcag gcctgctgcg acgtgctgaa tcgcccgctg     1440
caaattgttg cct                                                         1453

<210> SEQ ID NO 13
<211> LENGTH: 231
<212> TYPE: PRT
<213> ORGANISM: Escherichia coli

<400> SEQUENCE: 13

Met Leu Glu Asp Leu Lys Arg Gln Val Leu Glu Ala Asn Leu Ala Leu
1               5                   10                  15

Pro Lys His Asn Leu Val Thr Leu Thr Trp Gly Asn Val Ser Ala Val
                20                  25                  30

Asp Arg Glu Arg Gly Val Phe Val Ile Lys Pro Ser Gly Val Asp Tyr
            35                  40                  45

Ser Ile Met Thr Ala Asp Asp Met Val Val Ser Ile Glu Thr Gly
        50                  55                  60

Glu Val Val Glu Gly Ala Lys Lys Pro Ser Ser Asp Thr Pro Thr His
65                  70                  75                  80

Arg Leu Leu Tyr Gln Ala Phe Pro Ser Ile Gly Ile Val His Thr
                85                  90                  95

His Ser Arg His Ala Thr Ile Trp Ala Gln Ala Gly Gln Ser Ile Pro
            100                 105                 110

Ala Thr Gly Thr Thr His Ala Asp Tyr Phe Tyr Gly Thr Ile Pro Cys
        115                 120                 125

Thr Arg Lys Met Thr Asp Ala Glu Ile Asn Gly Glu Tyr Glu Trp Glu
    130                 135                 140

Thr Gly Asn Val Ile Val Glu Thr Phe Glu Lys Gln Gly Ile Asp Ala
145                 150                 155                 160

Ala Gln Met Pro Gly Val Leu Val His Ser His Gly Pro Phe Ala Trp
                165                 170                 175
```

```
Gly Lys Asn Ala Glu Asp Ala Val His Asn Ala Ile Val Leu Glu Glu
            180                 185                 190

Val Ala Tyr Met Gly Ile Phe Cys Arg Gln Leu Ala Pro Gln Leu Pro
        195                 200                 205

Asp Met Gln Gln Thr Leu Leu Asn Lys His Tyr Leu Arg Lys His Gly
210                 215                 220

Ala Lys Ala Tyr Tyr Gly Gln
225                 230

<210> SEQ ID NO 14
<211> LENGTH: 696
<212> TYPE: DNA
<213> ORGANISM: Escherichia coli

<400> SEQUENCE: 14
atgttagaag atctcaaacg ccaggtatta gaggccaacc tggcgctgcc aaaacataac     60
ctggtcacgc tcacatgggg caacgtcagc gccgttgatc gcgagcgcgg cgtctttgtg    120
atcaaacctt ccggcgtcga ttacagcatc atgaccgctg acgatatggt cgtggttagc    180
atcgaaaccg gtgaagtggt tgaaggtgcg aaaaagcgct cctccgatac gccaactcac    240
cgactgctct atcaggcatt cccgtccatt ggcggcattg tgcacacaca ctcgcgccac    300
gccactatct gggcgcaggc gggccagtcg attccagcaa ccggcaccac ccacgccgac    360
tatttctacg gcaccattcc ctgcacccgc aaaatgaccg acgcagaaat caacggtgaa    420
tatgagtggg aaaccggtaa cgtcatcgta gaaaccttcg aaaaacaggg tatcgatgca    480
gcgcaaatgc ccggcgtcct ggtccattct cacggcccat ttgcatgggg caaaaatgcc    540
gaagatgcgg tgcataacgc catcgtgctg aagaggtcg cttatatggg gatattctgc    600
cgtcagttag cgccgcagtt accggatatg cagcaaacgc tgctgaataa acactatctg    660
cgtaagcatg gcgcgaaggc atattacggg cagtaa                              696

<210> SEQ ID NO 15
<211> LENGTH: 438
<212> TYPE: PRT
<213> ORGANISM: Bacteroides thetaiotaomicron

<400> SEQUENCE: 15

Met Ala Thr Lys Glu Phe Phe Pro Gly Ile Glu Lys Ile Lys Phe Glu
1               5                   10                  15

Gly Lys Asp Ser Lys Asn Pro Met Ala Phe Arg Tyr Tyr Asp Ala Glu
            20                  25                  30

Lys Val Ile Asn Gly Lys Lys Met Lys Asp Trp Leu Arg Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asn Ala Asp Ala Ile Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
            100                 105                 110

Ser Val Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140
```

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
            165                 170                 175

Asp Ala Thr Ile Glu Leu Gly Gly Glu Asn Tyr Val Phe Trp Gly Gly
        180                 185                 190

Arg Glu Gly Tyr Met Ser Leu Leu Asn Thr Asp Gln Lys Arg Glu Lys
    195                 200                 205

Glu His Leu Ala Gln Met Leu Thr Ile Ala Arg Asp Tyr Ala Arg Ala
210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
            245                 250                 255

Lys Ala His Gly Leu Asp Lys Asp Phe Lys Val Asn Ile Glu Val Asn
        260                 265                 270

His Ala Thr Leu Ala Gly His Thr Phe Glu His Glu Leu Ala Val Ala
    275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Thr Gly
            325                 330                 335

Gly Thr Asn Phe Asp Ala Lys Thr Arg Arg Asn Ser Thr Asp Leu Glu
        340                 345                 350

Asp Ile Phe Ile Ala His Ile Ala Gly Met Asp Ala Met Ala Arg Ala
    355                 360                 365

Leu Glu Ser Ala Ala Ala Leu Leu Asp Glu Ser Pro Tyr Lys Lys Met
370                 375                 380

Leu Ala Asp Arg Tyr Ala Ser Phe Asp Gly Gly Lys Gly Lys Glu Phe
385                 390                 395                 400

Glu Asp Gly Lys Leu Thr Leu Glu Asp Val Val Ala Tyr Ala Lys Thr
            405                 410                 415

Lys Gly Glu Pro Lys Gln Thr Ser Gly Lys Gln Glu Leu Tyr Glu Ala
        420                 425                 430

Ile Leu Asn Met Tyr Cys
        435

<210> SEQ ID NO 16
<211> LENGTH: 1317
<212> TYPE: DNA
<213> ORGANISM: Bacteroides thetaiotaomicron

<400> SEQUENCE: 16
atggcaacaa aagaattttt tccgggaatt gaaaagatta aatttgaagg taaagatagt      60
aagaacccga tggcattccg ttattacgat gcagagaagg tgattaatgg taaaaagatg     120
aaggattggc tgagattcgc tatggcatgg tggcacacat tgtgcgctga aggtggtgat     180
cagttcggtg gcggaacaaa gcaattccca tggaatggta atgcagatgc tatacaggca     240
gcaaaagata agatggatgc aggatttgaa ttcatgcaga gatgggtat cgaatactat      300 tgcttccatg acgtagactt ggtttcggaa ggtgccagtg tagaagaata cgaagctaac     360
ctgaaagaaa tcgtagctta tgcaaaacag aaacaggcag aaaccggtat caaactactg     420

```
tggggtactg ctaatgtatt cggtcacgcc cgctatatga acggtgcagc taccaatcct    480
gacttcgatg tagtagctcg tgctgctgtt cagatcaaaa atgcgattga tgcaacgatt    540
gaacttggcg gagagaatta tgtgttttgg ggtggtcgtg aaggctatat gtctcttctg    600
aacacagatc agaacgtga aaagaacac cttgcacaga tgttgacgat tgctcgtgac    660
```
*(note: line 660 may read* `aacacagatc agaaacgtga aaagaacac cttgcacaga tgttgacgat tgctcgtgac`*)*
```
tatgcccgtg cccgtggttt caaaggtact ttcctgatcg aaccgaaacc gatggaaccg    720
actaaacatc aatatgacgt agatacggaa actgtaatcg gcttcctgaa agctcatggt    780
ctggataagg atttcaaagt aaatatcgag gtgaatcacg caactttggc aggtcacact    840
ttcgagcatg aattggctgt agctgtagac aatggtatgt gggctcaat  tgacgccaat    900 cgtggtgact atcagaatgg ctgggataca gaccaattcc cgatcgacaa ttatgaactg    960
actcaggcta tgatgcagat tatccgtaat ggtggtctcg gtaccggtgg tacgaacttt   1020
gatgctaaaa cccgtcgtaa ttctactgat ctggaagata tctttattgc tcacatcgca   1080
ggtatggacg ctatgcccg  tgcactcgaa agtgcagcgg ctctgctcga cgaatctccc   1140
tataagaaga tgctggctga ccgttatgct tcatttgatg ggggcaaagg taagaatttt   1200
gaagacggca agctgactct ggaggatgtg gttgcttatg caaaaacaaa aggcgaaccg   1260
aaacagacta gcggcaagca agaactttat gaggcaattc tgaatatgta ttgctaa     1317
```

<210> SEQ ID NO 17
<211> LENGTH: 258
<212> TYPE: PRT
<213> ORGANISM: Saccharomyces cerevisiae

<400> SEQUENCE: 17

Met Ala Ala Gly Val Pro Lys Ile Asp Ala Leu Glu Ser Leu Gly Asn
1               5                   10                  15

Pro Leu Glu Asp Ala Lys Arg Ala Ala Ala Tyr Arg Ala Val Asp Glu
            20                  25                  30

Asn Leu Lys Phe Asp Asp His Lys Ile Ile Gly Ile Gly Ser Gly Ser
        35                  40                  45

Thr Val Val Tyr Val Ala Glu Arg Ile Gly Gln Tyr Leu His Asp Pro
    50                  55                  60

Lys Phe Tyr Glu Val Ala Ser Lys Phe Ile Cys Ile Pro Thr Gly Phe
65                  70                  75                  80

Gln Ser Arg Asn Leu Ile Leu Asp Asn Lys Leu Gln Leu Gly Ser Ile
                85                  90                  95

Glu Gln Tyr Pro Arg Ile Asp Ile Ala Phe Asp Gly Ala Asp Glu Val
            100                 105                 110

Asp Glu Asn Leu Gln Leu Ile Lys Gly Gly Gly Ala Cys Leu Phe Gln
        115                 120                 125

Glu Lys Leu Val Ser Thr Ser Ala Lys Thr Phe Ile Val Val Ala Asp
    130                 135                 140

Ser Arg Lys Lys Ser Pro Lys His Leu Gly Lys Asn Trp Arg Gln Gly
145                 150                 155                 160

Val Pro Ile Glu Ile Val Pro Ser Ser Tyr Val Arg Val Lys Asn Asp
                165                 170                 175

Leu Leu Glu Gln Leu His Ala Glu Lys Val Asp Ile Arg Gln Gly Gly
            180                 185                 190

Ser Ala Lys Ala Gly Pro Val Val Thr Asp Asn Asn Asn Phe Ile Ile
        195                 200                 205

Asp Ala Asp Phe Gly Glu Ile Ser Asp Pro Arg Lys Leu His Arg Glu

```
                210               215               220
Ile Lys Leu Leu Val Gly Val Val Glu Thr Gly Leu Phe Ile Asp Asn
225               230               235               240

Ala Ser Lys Ala Tyr Phe Gly Asn Ser Asp Gly Ser Val Glu Val Thr
                245               250               255

Glu Lys

<210> SEQ ID NO 18
<211> LENGTH: 2467
<212> TYPE: DNA
<213> ORGANISM: Saccharomyces cerevisiae

<400> SEQUENCE: 18
ggatccaaga ccattattcc atcagaatgg aaaaaagttt aaaagatcac ggagattttg      60
ttcttctgag cttctgctgt ccttgaaaac aaattattcc gctggccgcc ccaaacaaaa     120
acaaccccga tttaataaca ttgtcacagt attagaaatt ttcttttttac aaattaccat    180 ttccagctta ctacttccta taatcctcaa tcttcagcaa cgacgcagg gaatagccgc      240 tgaggtgcat aactgtcact tttcaattcg ccaatgcaa tctcaggcgg acgaataagg      300
gggccctctc gagaaaaaca aaggaggat gagattagta ctttaatgtt gtgttcagta     360
attcagagac agacaagaga ggtttccaac acaatgtctt tagactcata ctatcttggg     420
tttgatcttt cgacccaaca actgaaatgt ctcgccatta accaggacct aaaaattgtc    480
cattcagaaa cagtggaatt tgaaaaggat cttccgcatt atcacacaaa gaagggtgtc    540
tatatacacg gcgacactat cgaatgtccc gtagccatgt ggttaggggc tctagatctg    600
gttctctcga aatatcgcga ggctaaattt ccattgaaca agttatggc cgtctcaggg      660 tcctgccagc agcacgggtc tgtctactgg tcctcccaag ccgaatctct gttagagcaa    720
ttgaataaga aaccggaaaa agatttattg cactacgtga gctctgtagc atttgcaagg    780
caaaccgccc ccaattggca agaccacagt actgcaaagc aatgtcaaga gtttgaagag    840
tgcataggtg ggcctgaaaa aatggctcaa ttaacagggt ccagagccca ttttagattt    900
actggtcctc aaattctgaa aattgcacaa ttagaaccag aagcttacga aaaaacaaag    960
accatttctt tagtgtctaa ttttttgact tctatcttag tgggccatct tgttgaatta   1020
gaggaggcag atgcctgtgg tatgaacctt tatgatatac gtgaaagaaa attcatgtat   1080
gagctactac atctaattga tagttcttct aaggataaaa ctatcagaca aaaattaatg   1140
agagcaccca tgaaaaattt gatagcgggt accatctgta aatattttat tgagaagtac   1200
ggtttcaata caaactgcaa ggtctctccc atgactgggg ataatttagc cactatatgt   1260
tctttacccc tgcggaagaa tgacgttctc gtttccctag aacaagtac tacagttctt   1320 ctggtcaccg ataagtatca cccctctccg aactatcatc tttttcattca tccaactctg   1380 ccaaaccatt atatgggtat gatttgttat tgtaatggtt ctttggcaag ggagaggata   1440
agagacgagt taaacaaaga acgggaaaat aattatgaga agactaacga ttggactctt   1500
tttaatcaag ctgtgctaga tgactcagaa agtagtgaaa atgaattagg tgtatatttt   1560
cctctggggg agatcgttcc tagcgtaaaa gccataaaca aagggttat cttcaatcca    1620 aaaacgggta tgattgaaag agaggtggcc aagttcaaag acaagaggca cgatgccaaa   1680 aatatattgtag aatcacaggc tttaagttgc agggtaagaa tatctccct gctttcggat   1740 tcaaacgcaa gctcacaaca gagactgaac gaagatacaa tcgtgaagtt tgattacgat   1800
gaatctccgc tgcgggacta cctaaataaa aggccagaaa ggacttttt tgtaggtggg   1860
```

```
gcttctaaaa acgatgctat tgtgaagaag tttgctcaag tcattggtgc tacaaagggt    1920
aattttaggc tagaaacacc aaactcatgt gccttggtg gttgttataa ggccatgtgg     1980
tcattgttat atgactctaa taaaattgca gttccttttg ataaatttct gaatgacaat    2040
tttccatggc atgtaatgga aagcatatcc gatgtggata tgaaaattg gatcgctata    2100 attccaagat tgtcccctta agcgaactgg aaaagactct catctaaaat atgtttgaat    2160
aatttatcat gccctgacaa gtacacacaa acacagacac ataatataca tacatatata    2220
tatatcaccg ttattatgcg tgcacatgac aatgcccttg tatgtttcgt atactgtagc    2280
aagtagtcat cattttgttc cccgttcgga aatgacaaa aagtaaaatc aataaatgaa     2340
gagtaaaaaa caatttatga aagggtgagc gaccagcaac gagagagaca aatcaaatta    2400
gcgctttcca gtgagaatat aagagagcat tgaaagagct aggttattgt taaatcatct    2460
cgagctc                                                              2467
```

<210> SEQ ID NO 19
<211> LENGTH: 238
<212> TYPE: PRT
<213> ORGANISM: Saccharomyces cerevisiae

<400> SEQUENCE: 19

```
Met Val Lys Pro Ile Ile Ala Pro Ser Ile Leu Ala Ser Asp Phe Ala
1               5                   10                  15

Asn Leu Gly Cys Glu Cys His Lys Val Ile Asn Ala Gly Ala Asp Trp
            20                  25                  30

Leu His Ile Asp Val Met Asp Gly His Phe Val Pro Asn Ile Thr Leu
        35                  40                  45

Gly Gln Pro Ile Val Thr Ser Leu Arg Arg Ser Val Pro Arg Pro Gly
    50                  55                  60

Asp Ala Ser Asn Thr Glu Lys Lys Pro Thr Ala Phe Phe Asp Cys His
65                  70                  75                  80

Met Met Val Glu Asn Pro Glu Lys Trp Val Asp Asp Phe Ala Lys Cys
                85                  90                  95

Gly Ala Asp Gln Phe Thr Phe His Tyr Glu Ala Thr Gln Asp Pro Leu
            100                 105                 110

His Leu Val Lys Leu Ile Lys Ser Lys Gly Ile Lys Ala Ala Cys Ala
        115                 120                 125

Ile Lys Pro Gly Thr Ser Val Asp Val Leu Phe Glu Leu Ala Pro His
    130                 135                 140

Leu Asp Met Ala Leu Val Met Thr Val Glu Pro Gly Phe Gly Gly Gln
145                 150                 155                 160

Lys Phe Met Glu Asp Met Met Pro Lys Val Glu Thr Leu Arg Ala Lys
                165                 170                 175

Phe Pro His Leu Asn Ile Gln Val Asp Gly Gly Leu Gly Lys Glu Thr
            180                 185                 190

Ile Pro Lys Ala Ala Lys Ala Gly Ala Asn Val Ile Val Ala Gly Thr
        195                 200                 205

Ser Val Phe Thr Ala Ala Asp Pro His Asp Val Ile Ser Phe Met Lys
    210                 215                 220

Glu Glu Val Ser Lys Glu Leu Arg Ser Arg Asp Leu Leu Asp
225                 230                 235
```

<210> SEQ ID NO 20
<211> LENGTH: 1328

<212> TYPE: DNA
<213> ORGANISM: Saccharomyces cerevisiae

<400> SEQUENCE: 20

```
gttaggcact tacgtatctt gtatagtagg aatggctcgg tttatgtata ttaggagatc     60
aaaacgagaa aaaatacca tatcgtatag tatagagagt ataaatataa gaaatgccgc    120
atatgtacaa ctaatctagc aaatctctag aacgcaattc cttcgagact tcttctttca    180
tgaaggagat aacatcgtgc gggtcagctg cagtgaaaac actggtacca gcgacaataa    240
cgttggcacc ggctttggcg gctttcggga tggtctcctt gcccaaacca ccatcgactt    300
ggatattcaa atgggggaac ttggctctca agtttccac ttttggcatc atgtcttcca    360
tgaattttg gcctccaaac ccaggttcca cagtcataac aagagccata tccaaatgag    420
gagctagttc aaataaaacg tcaacagaag taccaggttt gatggcgcat gcagctttga    480
tgcccttaga cttaatcaac ttaactaaat gcaagggtc ttgtgtggcc tcgtagtgga    540
acgtaaattg gtcagcacca catttagcaa aatcgtcgac ccattttca ggattttcaa    600
ccatcatgtg acaatcgaag aacgcagtgg gcttcttttc tgtgttgcta gcatcgccag    660
ggcgtggcac agaacgacgt agggaggtaa caattggttg gcccagagta atgtttggaa    720
caaaatggcc gtccatgaca tcgatatgta accaatctgc gccggcgttg atgaccttat    780
gacattcgca acccaagttg gcgaagtcag aagcaaggat actgggagct ataattggtt    840
tgaccatttt ttcttgtgtg tttacctcgc tcttggaatt agcaaatggc cttcttgcat    900
gaaattgtat cgagtttgct ttatttttct ttttacgggc ggattctttc tattctggct    960
ttcctataac agagatcatg aaagaagttc cagcttacgg atcaagaaag tacctataca   1020
tatacaaaaa tctgattact ttcccagctc gacttggata gctgttcttg ttttctcttg   1080
gcgacacatt ttttgtttct gaagccacgt cctgctttat aagaggacat ttaaagttgc   1140
aggacttgaa tgcaattacc ggaagaagca accaaccggc atggttcagc atacaataca   1200
catttgatta gaaaagcaga gaataaatag acatgatacc tctcttttta tcctctgcag   1260
cgtattattg tttattccac gcaggcatcg gtcgttggct gttgttatgt ctcagataag   1320
cgcgtttg                                                            1328
```

<210> SEQ ID NO 21
<211> LENGTH: 680
<212> TYPE: PRT
<213> ORGANISM: Saccharomyces cerevisiae

<400> SEQUENCE: 21

```
Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
            20                  25                  30

Ala Pro Leu Gly Met Ala Pro Ala Ala His Val Leu Trp Ser Gln Met
        35                  40                  45

Arg Met Asn Pro Thr Asn Pro Asp Trp Ile Asn Arg Asp Arg Phe Val
    50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110
```

```
Val Thr Thr Gly Pro Leu Gly Gln Gly Ile Ser Asn Ala Val Gly Met
            115                 120                 125

Ala Met Ala Gln Ala Asn Leu Ala Thr Tyr Asn Lys Pro Gly Phe
    130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
    210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
                245                 250                 255

Ala Gly Ser His Ser Val His Gly Ala Pro Leu Lys Ala Asp Asp Val
            260                 265                 270

Lys Gln Leu Lys Ser Lys Phe Gly Phe Asn Pro Asp Lys Ser Phe Val
        275                 280                 285

Val Pro Gln Glu Val Tyr Asp His Tyr Gln Lys Thr Ile Leu Lys Pro
    290                 295                 300

Gly Val Glu Ala Asn Asn Lys Trp Asn Lys Leu Phe Ser Glu Tyr Gln
305                 310                 315                 320

Lys Lys Phe Pro Glu Leu Gly Ala Glu Leu Ala Arg Arg Leu Ser Gly
                325                 330                 335

Gln Leu Pro Ala Asn Trp Glu Ser Lys Leu Pro Thr Tyr Thr Ala Lys
            340                 345                 350

Asp Ser Ala Val Ala Thr Arg Lys Leu Ser Glu Thr Val Leu Glu Asp
        355                 360                 365

Val Tyr Asn Gln Leu Pro Glu Leu Ile Gly Gly Ser Ala Asp Leu Thr
    370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
            420                 425                 430

Ala Asn Tyr Lys Pro Tyr Gly Gly Thr Phe Leu Asn Phe Val Ser Tyr
        435                 440                 445

Ala Ala Gly Ala Val Arg Leu Ser Ala Leu Ser Gly His Pro Val Ile
    450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
            500                 505                 510

Asn Ser Leu Glu Ser Lys His Thr Pro Ser Ile Ile Ala Leu Ser Arg
        515                 520                 525
```

```
Gln Asn Leu Pro Gln Leu Glu Gly Ser Ser Ile Glu Ser Ala Ser Lys
            530                 535                 540

Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
    610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680

<210> SEQ ID NO 22
<211> LENGTH: 2046
<212> TYPE: DNA
<213> ORGANISM: Saccharomyces cerevisiae

<400> SEQUENCE: 22
atggcacagt tctccgacat tgataaactt gcggtttcca ctttaagatt actttccgtt      60
gaccaggtgg aaagcgcaca atctggccac ccaggtgcac cactaggatt ggcaccagtt     120
gcccatgtaa ttttcaagca actgcgctgt aaccctaaca tgaacattg gatcaataga     180 gacaggtttg ttctgtcgaa cggtcactca tgcgctcttc tgtactcaat gctccatcta     240
ttaggatacg attactctat cgaggacttg agacaattta gacaagtaaa ctcaaggaca     300
ccgggtcatc cagaattcca ctcagcggga gtggaaatca cttccggtcc gctaggccag     360
ggtatctcaa atgctgttgg tatggcaata gcgcaggcca actttgccgc cactttataac    420 gaggatggct ttcccatttc cgactcatat acgtttgcta ttgtagggga tggttgctta     480
caagagggtg tttcttcgga gacctcttcc ttagcgggac atctgcaatt gggtaacttg     540
attacgtttt atgacagtaa tagcatttcc attgacggta aaacctcgta ctcgttcgac     600
gaagatgttt tgaagcgata cgaggcatat ggttgggaag tcatggaagt cgataaagga     660
gacgacgata tggaatccat ttctagcgct ttggaaaagg caaaactatc gaaggacaag     720
ccaaccataa tcaaggtaac tactacaatt ggatttgggt ccctacaaca gggtactgct     780
ggtgttcatg ggtccgcttt gaaggcagat gatgttaaac agttgaagaa gaggtggggg     840
tttgacccaa ataatcatt tgtagtacct caagaggtgt acgattatta taagaagact     900
gttgtggaac ccggtcaaaa acttaatgag gaatgggata ggatgtttga agaatacaaa     960
accaaatttc ccgagaaggg taagaattg caaagaagat tgaatggtga gttaccggaa    1020
ggttgggaaa agcatttacc gaagtttact ccggacgacg atgctctggc aacaagaaag    1080
acatcccagc aggtgctgac gaacatggtc caagttttgc ctgaattgat cggtggttct    1140
gccgatttga caccttcgaa tctgacaagg tgggaaggcg cggtagattt ccaacctccc    1200 attcccaac taggtaacta tgcaggaagg tacattagat acggtgtgag ggaacacgga    1260
```

-continued

```
atgggtgcca ttatgaacgg tatctctgcc tttggtgcaa actacaagcc ttacggtggt   1320
acctttttga acttcgtctc ttatgctgca ggagccgtta ggttagccgc cttgtctggt   1380
aatccagtca tttgggttgc aacacatgac tctatcgggc ttggtgagga tggtccaacg   1440
caccaaccta ttgaaactct ggctcacttg agggctattc aaacatgca tgtatggaga    1500 cctgctgatg gtaacgaaac ttctgctgcg tattattctg ctatcaaatc tggtcgaaca   1560
ccatctgttg tggctttatc acgacagaat cttcctcaat ggagcattc ctcttttgaa    1620 aaagccttga agggtggcta tgtgatccat gacgtggaga tcctgatat tatcctggtg    1680 tcaacaggat cagaagtctc catttctata gatgcagcca aaaaattgta cgatactaaa   1740
aaaatcaaag caagagttgt ttccctgcca gactttttata cttttgacag caaagtgaa   1800 gaatacagat tctctgttct accagacggt gttccgatca tgtcctttga agtattggct   1860
acttcaagct ggggtaagta tgctcatcaa tcgttcggac tcgacgaatt tggtcgttca   1920
ggcaaggggc ctgaaattta caattgttc gatttcacag cggacggtgt tgcgtcaagg    1980
gctgaaaaga caatcaatta ctacaaagga aagcagttgc tttctcctat gggaagagct   2040
ttctaa                                                              2046
```

<210> SEQ ID NO 23
<211> LENGTH: 335
<212> TYPE: PRT
<213> ORGANISM: Saccharomyces cerevisiae

<400> SEQUENCE: 23

```
Met Ser Glu Pro Ala Gln Lys Lys Gln Lys Val Ala Asn Asn Ser Leu
1               5                   10                  15

Glu Gln Leu Lys Ala Ser Gly Thr Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
    50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
            100                 105                 110

Leu Ser Phe Asp Thr Gln Ala Thr Ile Glu Lys Ala Arg His Ile Ile
        115                 120                 125

Lys Leu Phe Glu Gln Glu Gly Val Ser Lys Glu Arg Val Leu Ile Lys
    130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Lys
        195                 200                 205

Gly Glu Ala Asp Pro Gly Val Ile Ser Val Lys Lys Ile Tyr Asn Tyr
    210                 215                 220
```

```
Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
            245                 250                 255

Ser Pro Ala Leu Leu Asp Lys Leu Met Asn Ser Thr Glu Pro Phe Pro
        260                 265                 270

Arg Val Leu Asp Pro Val Ser Ala Lys Lys Glu Ala Gly Asp Lys Ile
    275                 280                 285

Ser Tyr Ile Ser Asp Glu Ser Lys Phe Arg Phe Asp Leu Asn Glu Asp
290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335

<210> SEQ ID NO 24
<211> LENGTH: 2046
<212> TYPE: DNA
<213> ORGANISM: Saccharomyces cerevisiae

<400> SEQUENCE: 24
atggcacagt tctccgacat tgataaactt gcggtttcca ctttaagatt actttccgtt     60
gaccaggtgg aaagcgcaca atctggccac ccaggtgcac cactaggatt ggcaccagtt    120
gcccatgtaa ttttcaagca actgcgctgt aaccctaaca tgaacattg atcaataga     180 gacaggtttg ttctgtcgaa cggtcactca tgcgctcttc tgtactcaat gctccatcta    240
ttaggatacg attactctat cgaggacttg agacaattta gacaagtaaa ctcaaggaca    300
ccgggtcatc cagaattcca ctcagcggga gtggaaatca cttccggtcc gctaggccag    360
ggtatctcaa atgctgttgg tatggcaata gcgcaggcca actttgccgc cacttataac    420
gaggatggct ttcccatttc cgactcatat acgtttgcta ttgtagggga tggttgctta    480
caagagggtg tttcttcgga gacctcttcc ttagcgggac atctgcaatt gggtaacttg    540
attacgtttt atgacagtaa tagcatttcc attgacggta aaacctcgta ctcgttcgac    600
gaagatgttt tgaagcgata cgaggcatat ggttgggaag tcatggaagt cgataaagga    660
gacgacgata tggaatccat ttctagcgct ttggaaaagg caaaactatc gaaggacaag    720
ccaaccataa tcaaggtaac tactacaatt ggatttgggt ccctacaaca gggtactgct    780
ggtgttcatg ggtccgcttt gaaggcagat gatgttaaac agttgaagaa gaggtggggg    840
tttgacccaa ataaatcatt tgtagtacct caagaggtgt acgattatta taagaagact    900
gttgtggaac ccggtcaaaa acttaatgag aatgggata ggatgtttga agaatacaaa    960
accaaatttc ccgagaaggg taagaattg caaagaagat tgaatggtga gttaccggaa   1020
ggttgggaaa agcatttacc gaagtttact ccggacgacg atgctctggc aacaagaaag   1080
acatcccagc aggtgctgac gaacatggtc caagttttgc ctgaattgat cggtggttct   1140
gccgatttga caccttcgaa tctgacaagg tgggaaggcg cggtagattt ccaacctccc   1200 attcccaac taggtaacta tgcaggaagg tacattagat acggtgtgag ggaacacgga   1260
atgggtgcca ttatgaacgg tatctctgcc tttggtgcaa actacaagcc ttacggtggt   1320
acctttttga acttcgtctc ttatgctgca ggagccgtta ggttagccgc cttgtctggt   1380
aatccagtca tttgggttgc aacacatgac tctatcgggc ttggtgagga tggtccaacg   1440
caccaaccta ttgaaactct ggctcacttg agggctattc caaacatgca gtatggaga   1500
```

```
cctgctgatg gtaacgaaac ttctgctgcg tattattctg ctatcaaatc tggtcgaaca      1560
ccatctgttg tggctttatc acgacagaat cttcctcaat tggagcattc ctcttttgaa      1620
aaagccttga agggtggcta tgtgatccat gacgtggaga atcctgatat tatcctggtg      1680
tcaacaggat cagaagtctc catttctata gatgcagcca aaaaattgta cgatactaaa      1740
aaaatcaaag caagagttgt tccctgcca gactttata cttttgacag caaagtgaa         1800 gaatacagat tctctgttct accagacggt gttccgatca tgtcctttga agtattggct      1860
acttcaagct ggggtaagta tgctcatcaa tcgttcggac tcgacgaatt tggtcgttca      1920
ggcaaggggc ctgaaattta caattgttc gatttcacag cggacggtgt tgcgtcaagg       1980
gctgaaaaga caatcaatta ctacaaagga aagcagttgc tttctcctat gggaagagct      2040
ttctaa                                                                 2046

<210> SEQ ID NO 25
<211> LENGTH: 600
<212> TYPE: PRT
<213> ORGANISM: Saccharomyces cerevisiae

<400> SEQUENCE: 25

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
                245                 250                 255

Asp Lys Thr Ile Arg Gln Lys Leu Met Arg Ala Pro Met Lys Asn Leu
            260                 265                 270
```

```
Ile Ala Gly Thr Ile Cys Lys Tyr Phe Ile Glu Lys Tyr Gly Phe Asn
            275                 280                 285
Thr Asn Cys Lys Val Ser Pro Met Thr Gly Asp Asn Leu Ala Thr Ile
            290                 295                 300
Cys Ser Leu Pro Leu Arg Lys Asn Asp Val Leu Val Ser Leu Gly Thr
305                 310                 315                 320
Ser Thr Thr Val Leu Leu Val Thr Asp Lys Tyr His Pro Ser Pro Asn
            325                 330                 335
Tyr His Leu Phe Ile His Pro Thr Leu Pro Asn His Tyr Met Gly Met
            340                 345                 350
Ile Cys Tyr Cys Asn Gly Ser Leu Ala Arg Glu Arg Ile Arg Asp Glu
            355                 360                 365
Leu Asn Lys Glu Arg Glu Asn Asn Tyr Glu Lys Thr Asn Asp Trp Thr
            370                 375                 380
Leu Phe Asn Gln Ala Val Leu Asp Asp Ser Glu Ser Ser Glu Asn Glu
385                 390                 395                 400
Leu Gly Val Tyr Phe Pro Leu Gly Glu Ile Val Pro Ser Val Lys Ala
            405                 410                 415
Ile Asn Lys Arg Val Ile Phe Asn Pro Lys Thr Gly Met Ile Glu Arg
            420                 425                 430
Glu Val Ala Lys Phe Lys Asp Lys Arg His Asp Ala Lys Asn Ile Val
            435                 440                 445
Glu Ser Gln Ala Leu Ser Cys Arg Val Arg Ile Ser Pro Leu Leu Ser
            450                 455                 460
Asp Ser Asn Ala Ser Ser Gln Gln Arg Leu Asn Glu Asp Thr Ile Val
465                 470                 475                 480
Lys Phe Asp Tyr Asp Glu Ser Pro Leu Arg Asp Tyr Leu Asn Lys Arg
            485                 490                 495
Pro Glu Arg Thr Phe Phe Val Gly Gly Ala Ser Lys Asn Asp Ala Ile
            500                 505                 510
Val Lys Lys Phe Ala Gln Val Ile Gly Ala Thr Lys Gly Asn Phe Arg
            515                 520                 525
Leu Glu Thr Pro Asn Ser Cys Ala Leu Gly Gly Cys Tyr Lys Ala Met
            530                 535                 540
Trp Ser Leu Leu Tyr Asp Ser Asn Lys Ile Ala Val Pro Phe Asp Lys
545                 550                 555                 560
Phe Leu Asn Asp Asn Phe Pro Trp His Val Met Glu Ser Ile Ser Asp
            565                 570                 575
Val Asp Asn Glu Asn Trp Asp Arg Tyr Asn Ser Lys Ile Val Pro Leu
            580                 585                 590
Ser Glu Leu Glu Lys Thr Leu Ile
            595                 600

<210> SEQ ID NO 26
<211> LENGTH: 2467
<212> TYPE: DNA
<213> ORGANISM: Saccharomyces cerevisiae

<400> SEQUENCE: 26
ggatccaaga ccattattcc atcagaatgg aaaaaagttt aaaagatcac ggagattttg      60
ttcttctgag cttctgctgt ccttgaaaac aaattattcc gctggccgcc ccaaacaaaa     120
acaaccccga tttaataaca ttgtcacagt attagaaatt ttcttttttac aaattaccat     180 ttccagctta ctacttccta taatcctcaa tcttcagcaa gcgacgcagg gaatagccgc     240
```

```
tgaggtgcat aactgtcact tttcaattcg gccaatgcaa tctcaggcgg acgaataagg    300
gggccctctc gagaaaaaca aaaggaggat gagattagta ctttaatgtt gtgttcagta    360
attcagagac agacaagaga ggtttccaac acaatgtctt tagactcata ctatcttggg    420
tttgatcttt cgacccaaca actgaaatgt ctcgccatta accaggacct aaaaattgtc    480
cattcagaaa cagtggaatt tgaaaaggat cttccgcatt atcacacaaa gaagggtgtc    540
tatatacacg gcgacactat cgaatgtccc gtagccatgt ggttaggggc tctagatctg    600
gttctctcga aatatcgcga ggctaaattt ccattgaaca aagttatggc cgtctcaggg    660
tcctgccagc agcacgggtc tgtctactgg tcctcccaag ccgaatctct gttagagcaa    720
ttgaataaga aaccggaaaa agatttattg cactacgtga gctctgtagc atttgcaagg    780
caaaccgccc ccaattggca agaccacagt actgcaaagc aatgtcaaga gtttgaagag    840
tgcataggtg ggcctgaaaa aatggctcaa ttaacagggc ccagagccca ttttagattt    900
actggtcctc aaattctgaa aattgcacaa ttagaaccag aagcttacga aaaaacaaag    960
accatttctt tagtgtctaa tttttgact tctatcttag tgggccatct tgttgaatta    1020
gaggaggcag atgcctgtgg tatgaacctt tatgatatac gtgaaagaaa attcatgtat    1080
gagctactac atctaattga tagttcttct aaggataaaa ctatcagaca aaaattaatg    1140
agagcaccca tgaaaaattt gatagcgggt accatctgta aatattttat tgagaagtac    1200
ggtttcaata caaactgcaa ggtctctccc atgactgggg ataatttagc cactatatgt    1260
tctttacccc tgcggaagaa tgacgttctc gtttccctag gaacaagtac tacagttctt    1320
ctggtcaccg ataagtatca cccctctccg aactatcatc ttttcattca tccaactctg    1380
ccaaaccatt atatgggtat gatttgttat tgtaatggtt ctttggcaag ggagaggata    1440
agagacgagt taaacaaaga acgggaaaat aattatgaga agactaacga ttggactctt    1500
tttaatcaag ctgtgctaga tgactcagaa agtagtgaaa atgaattagg tgtatatttt    1560
cctctggggg agatcgttcc tagcgtaaaa gccataaaca aaagggttat cttcaatcca    1620
aaaacgggta tgattgaaag agaggtggcc aagttcaaag acaagaggca cgatgccaaa    1680
aatattgtag aatcacaggc tttaagttgc agggtaagaa tatctcccct gctttcggat    1740
tcaaacgcaa gctcacaaca gagactgaac gaagatacaa tcgtgaagtt tgattacgat    1800
gaatctccgc tgcgggacta cctaaataaa aggccagaaa ggacttttt tgtaggtggg    1860
gcttctaaaa acgatgctat tgtgaagaag tttgctcaag tcattggtgc tacaaagggt    1920
aattttaggc tagaaacacc aaactcatgt gcccttggtg gttgttataa ggccatgtgg    1980
tcattgttat atgactctaa taaaattgca gttcctttg ataaatttct gaatgacaat    2040
tttccatggc atgtaatgga aagcatatcc gatgtggata tgaaaattg gatcgctata    2100
attccaagat tgtccccta agcgaactgg aaaagactct catctaaaat atgtttgaat    2160
aatttatcat gccctgacaa gtacacacaa acacagacac ataatataca tacatatata    2220
tatatcaccg ttattatgcg tgcacatgac aatgcccttg tatgtttcgt atactgtagc    2280
aagtagtcat cattttgttc cccgttcgga aaatgacaaa agtaaaatc aataaatgaa    2340
gagtaaaaaa caatttatga aagggtgagc gaccagcaac gagagagaca aatcaaatta    2400
gcgctttcca gtgagaatat aagagagcat tgaaagagct aggttattgt taaatcatct    2460
cgagctc                                                              2467

<210> SEQ ID NO 27
<211> LENGTH: 494
```

<212> TYPE: PRT
<213> ORGANISM: Piromyces sp.

<400> SEQUENCE: 27

```
Met Lys Thr Val Ala Gly Ile Asp Leu Gly Thr Gln Ser Met Lys Val
1               5                   10                  15

Val Ile Tyr Asp Tyr Glu Lys Lys Glu Ile Ile Glu Ser Ala Ser Cys
            20                  25                  30

Pro Met Glu Leu Ile Ser Glu Ser Asp Gly Thr Arg Glu Gln Thr Thr
        35                  40                  45

Glu Trp Phe Asp Lys Gly Leu Glu Val Cys Phe Gly Lys Leu Ser Ala
    50                  55                  60

Asp Asn Lys Lys Thr Ile Glu Ala Ile Gly Ile Ser Gly Gln Leu His
65                  70                  75                  80

Gly Phe Val Pro Leu Asp Ala Asn Gly Lys Ala Leu Tyr Asn Ile Lys
                85                  90                  95

Leu Trp Cys Asp Thr Ala Thr Val Glu Glu Cys Lys Ile Ile Thr Asp
            100                 105                 110

Ala Ala Gly Gly Asp Lys Ala Val Ile Asp Ala Leu Gly Asn Leu Met
        115                 120                 125

Leu Thr Gly Phe Thr Ala Pro Lys Ile Leu Trp Leu Lys Arg Asn Lys
130                 135                 140

Pro Glu Ala Phe Ala Asn Leu Lys Tyr Ile Met Leu Pro His Asp Tyr
145                 150                 155                 160

Leu Asn Trp Lys Leu Thr Gly Asp Tyr Val Met Glu Tyr Gly Asp Ala
                165                 170                 175

Ser Gly Thr Ala Leu Phe Asp Ser Lys Asn Arg Cys Trp Ser Lys Lys
            180                 185                 190

Ile Cys Asp Ile Ile Asp Pro Lys Leu Leu Asp Leu Leu Pro Lys Leu
        195                 200                 205

Ile Glu Pro Ser Ala Pro Ala Gly Lys Val Asn Asp Glu Ala Ala Lys
    210                 215                 220

Ala Tyr Gly Ile Pro Ala Gly Ile Pro Val Ser Ala Gly Gly Asp
225                 230                 235                 240

Asn Met Met Gly Ala Val Gly Thr Gly Thr Val Ala Asp Gly Phe Leu
                245                 250                 255

Thr Met Ser Met Gly Thr Ser Gly Thr Leu Tyr Gly Tyr Ser Asp Lys
            260                 265                 270

Pro Ile Ser Asp Pro Ala Asn Gly Leu Ser Gly Phe Cys Ser Ser Thr
        275                 280                 285

Gly Gly Trp Leu Pro Leu Leu Cys Thr Met Asn Cys Thr Val Ala Thr
    290                 295                 300

Glu Phe Val Arg Asn Leu Phe Gln Met Asp Ile Lys Glu Leu Asn Val
305                 310                 315                 320

Glu Ala Ala Lys Ser Pro Cys Gly Ser Glu Gly Val Leu Val Ile Pro
                325                 330                 335

Phe Phe Asn Gly Glu Arg Thr Pro Asn Leu Pro Asn Gly Arg Ala Ser
            340                 345                 350

Ile Thr Gly Leu Thr Ser Ala Asn Thr Ser Arg Ala Asn Ile Ala Arg
        355                 360                 365

Ala Ser Phe Glu Ser Ala Val Phe Ala Met Arg Gly Gly Leu Asp Ala
    370                 375                 380

Phe Arg Lys Leu Gly Phe Gln Pro Lys Glu Ile Arg Leu Ile Gly Gly
385                 390                 395                 400
```

```
Gly Ser Lys Ser Asp Leu Trp Arg Gln Ile Ala Ala Asp Ile Met Asn
            405                 410                 415

Leu Pro Ile Arg Val Pro Leu Leu Glu Ala Ala Ala Leu Gly Gly
            420                 425                 430

Ala Val Gln Ala Leu Trp Cys Leu Lys Asn Gln Ser Gly Lys Cys Asp
            435                 440                 445

Ile Val Glu Leu Cys Lys Glu His Ile Lys Ile Asp Glu Ser Lys Asn
    450                 455                 460

Ala Asn Pro Ile Ala Glu Asn Val Ala Val Tyr Asp Lys Ala Tyr Asp
465                 470                 475                 480

Glu Tyr Cys Lys Val Val Asn Thr Leu Ser Pro Leu Tyr Ala
            485                 490

<210> SEQ ID NO 28
<211> LENGTH: 2041
<212> TYPE: DNA
<213> ORGANISM: Piromyces sp.

<400> SEQUENCE: 28
```

| | | | | | |
|---|---|---|---|---|---|
| attatataaa | ataactttaa | ataaaacaat | ttttatttgt | ttatttaatt | attcaaaaaa | 60 |
| aattaaagta | aaagaaaaat | aatacagtag | aacaatagta | ataatatcaa | aatgaagact | 120 |
| gttgctggta | ttgatcttgg | aactcaaagt | atgaaagtcg | ttatttacga | ctatgaaaag | 180 |
| aaagaaatta | ttgaaagtgc | tagctgtcca | atggaattga | tttccgaaag | tgacggtacc | 240 |
| cgtgaacaaa | ccactgaatg | gtttgacaag | ggtcttgaag | tttgttttgg | taagcttagt | 300 |
| gctgataaca | aaaagactat | tgaagctatt | ggtatttctg | gtcaattaca | cggttttgtt | 360 |
| cctcttgatg | ctaacggtaa | ggctttatac | aacatcaaac | tttggtgtga | tactgctacc | 420 |
| gttgaagaat | gtaagattat | cactgatgct | gccggtggtg | acaaggctgt | tattgatgcc | 480 |
| cttggtaacc | ttatgctcac | cggtttcacc | gctccaaaga | tcctctggct | caagcgcaac | 540 |
| aagccagaag | cttttcgctaa | cttaaagtac | attatgcttc | cacacgatta | cttaaactgg | 600 |
| aagcttactg | gtgattacgt | tatggaatac | ggtgatgcct | ctggtaccgc | tctcttcgat | 660 |
| tctaagaacc | gttgctggtc | taagaagatt | tgcgatatca | ttgacccaaa | acttttagat | 720 |
| ttacttccaa | agttaattga | accaagcgct | ccagctggta | aggttaatga | tgaagccgct | 780 |
| aaggcttacg | gtattccagc | cggtattcca | gtttccgctg | gtggtggtga | taacatgatg | 840 |
| ggtgctgttg | gtactggtac | tgttgctgat | ggtttcctta | ccatgtctat | gggtacttct | 900 |
| ggtactcttt | acggttacag | tgacaagcca | attagtgacc | cagctaatgg | tttaagtggt | 960 |
| ttctgttctt | ctactggtgg | atggcttcca | ttactttgta | ctatgaactg | tactgttgcc | 1020 |
| actgaattcg | ttcgtaacct | cttccaaatg | gatattaagg | aacttaatgt | tgaagctgcc | 1080 |
| aagtctccat | gtggtagtga | aggtgtttta | gttattccat | tcttcaatgg | tgaaagaact | 1140 |
| ccaaacttac | aaacggtcg | tgctagtatt | actggtctta | cttctgctaa | caccagccgt | 1200 |
| gctaacattg | ctcgtgctag | tttcgaatcc | gccgttttcg | ctatgcgtgg | tggtttagat | 1260 |
| gctttccgta | agttaggttt | ccaaccaaag | gaaattcgtc | ttattggtgg | tggttctaag | 1320 |
| tctgatctct | ggagacaaat | tgccgctgat | atcatgaacc | ttccaatcag | agttccactt | 1380 |
| ttagaagaag | ctgctgctct | tggtggtgct | gttcaagctt | tatggtgtct | taagaaccaa | 1440 |
| tctggtaagt | gtgatattgt | tgaactttgc | aaagaacaca | ttaagattga | tgaatctaag | 1500 |
| aatgctaacc | caattgccga | aaatgttgct | gtttacgaca | aggcttacga | tgaatactgc | 1560 |

-continued

```
aaggttgtaa atactctttc tccattatat gcttaaattg ccaatgtaaa aaaaaatata    1620
atgccatata attgccttgt caatacactg ttcatgttca taatcata ggacattgaa      1680 tttacaaggt ttatacaatt aatatctatt atcatattat tatacagcat ttcattttct    1740
aagattagac gaaacaattc ttggttcctt gcaatataca aaatttacat gaattttag     1800 aatagtctcg tatttatgcc caataatcag gaaaattacc taatgctgga ttcttgttaa    1860
taaaaacaaa ataataaat taataaaca aataaaaatt ataagtaaat ataatatat       1920 aagtaatata aaaaaaagt aaatataaa ataataaat aaaattttt tgcaaatata        1980 taaataaata aataaaatat aaaataatt tagcaaataa attaaaaaaa aaaaaaaaa      2040 a                                                                    2041
```

<210> SEQ ID NO 29
<211> LENGTH: 327
<212> TYPE: PRT
<213> ORGANISM: Saccharomyces cerevisiae

<400> SEQUENCE: 29

```
Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285
```

```
Ile Glu Lys Lys Phe Thr Leu Thr Glu Gln Glu Leu Lys Asp Ile Ser
        290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 30
<211> LENGTH: 984
<212> TYPE: DNA
<213> ORGANISM: Saccharomyces cerevisiae

<400> SEQUENCE: 30
atgtcttcac tggttactct taataacggt ctgaaaatgc ccctagtcgg cttagggtgc    60
tggaaaattg acaaaaaagt ctgtgcgaat caaatttatg aagctatcaa attaggctac   120
cgtttattcg atggtgcttg cgactacggc aacgaaaagg aagttggtga aggtatcagg   180
aaagccatct ccgaaggtct tgtttctaga aggatatat ttgttgtttc aaagttatgg    240
aacaattttc accatcctga tcatgtaaaa ttagctttaa agaagacctt aagcgatatg   300
ggacttgatt atttagacct gtattatatt cacttcccaa tcgccttcaa atatgttcca   360
tttgaagaga ataccctcc aggattctat acgggcgcag atgacgagaa gaaaggtcac    420
atcaccgaag cacatgtacc aatcatagat acgtaccggg ctctggaaga atgtgttgat   480
gaaggcttga ttaagtctat tggtgttttcc aactttcagg aagcttgat tcaagattta   540 ttacgtggtt gtagaatcaa gcccgtggct ttgcaaattg aacaccatcc ttatttgact   600
caagaacacc tagttgagtt ttgtaaatta cacgatatcc aagtagttgc ttactcctcc   660
ttcggtcctc aatcattcat tgagatggac ttacagttgg caaaaaccac gccaactctg   720
ttcgagaatg atgtaatcaa gaaggtctca caaaaccatc caggcagtac cacttcccaa   780
gtattgctta gatgggcaac tcagagaggc attgccgtca ttccaaaatc ttccaagaag   840
gaaaggttac ttggcaacct agaaatcgaa aaaagttca ctttaacgga gcaagaattg    900
aaggatattt ctgcactaaa tgccaacatc agatttaatg atccatggac ctggttggat   960
ggtaaattcc ccactttgc ctga                                          984

<210> SEQ ID NO 31
<211> LENGTH: 31
<212> TYPE: DNA
<213> ORGANISM: Artificial Sequence
<220> FEATURE:
<223> OTHER INFORMATION: primer

<400> SEQUENCE: 31
gactagtcga gtttatcatt atcaatactg c                                  31

<210> SEQ ID NO 32
<211> LENGTH: 49
<212> TYPE: DNA
<213> ORGANISM: Artificial Sequence
<220> FEATURE:
<223> OTHER INFORMATION: primer

<400> SEQUENCE: 32
ctcataatca ggtactgata acattttgtt tgtttatgtg tgtttattc                49

<210> SEQ ID NO 33
<211> LENGTH: 49
```

```
<212> TYPE: DNA
<213> ORGANISM: Artificial Sequence
<220> FEATURE:
<223> OTHER INFORMATION: primer

<400> SEQUENCE: 33
gaataaacac acataaacaa acaaaatgtt atcagtacct gattatgag         49

<210> SEQ ID NO 34
<211> LENGTH: 48
<212> TYPE: DNA
<213> ORGANISM: Artificial Sequence
<220> FEATURE:
<223> OTHER INFORMATION: primer

<400> SEQUENCE: 34
aatcataaat cataagaaat tcgcttactt taagaatgcc ttagtcat          48

<210> SEQ ID NO 35
<211> LENGTH: 48
<212> TYPE: DNA
<213> ORGANISM: Artificial Sequence
<220> FEATURE:
<223> OTHER INFORMATION: primer

<400> SEQUENCE: 35
atgactaagg cattcttaaa gtaagcgaat ttcttatgat ttatgatt          48

<210> SEQ ID NO 36
<211> LENGTH: 36
<212> TYPE: DNA
<213> ORGANISM: Artificial Sequence
<220> FEATURE:
<223> OTHER INFORMATION: primer

<400> SEQUENCE: 36
cactagtctc gagtgtggaa gaacgattac aacagg                       36

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
cgagctcgtg ggtgtattgg attataggaa g                            31

<210> SEQ ID NO 38
<211> LENGTH: 48
<212> TYPE: DNA
<213> ORGANISM: Artificial Sequence
<220> FEATURE:
<223> OTHER INFORMATION: primer

<400> SEQUENCE: 38
ttgggctgtt tcaactaaat tcattttag gctggtatct tgattcta           48

<210> SEQ ID NO 39
<211> LENGTH: 48
<212> TYPE: DNA
<213> ORGANISM: Artificial Sequence
<220> FEATURE:
<223> OTHER INFORMATION: primer

<400> SEQUENCE: 39
```
tagaatcaag ataccagcct aaaaatgaat ttagttgaaa cagcccaa                    48

<210> SEQ ID NO 40
<211> LENGTH: 48
<212> TYPE: DNA
<213> ORGANISM: Artificial Sequence
<220> FEATURE:
<223> OTHER INFORMATION: primer

<400> SEQUENCE: 40
aatcataaat cataagaaat tcgctctaat atttgattgc ttgcccag                    48

<210> SEQ ID NO 41
<211> LENGTH: 48
<212> TYPE: DNA
<213> ORGANISM: Artificial Sequence
<220> FEATURE:
<223> OTHER INFORMATION: primer

<400> SEQUENCE: 41
ctgggcaagc aatcaaatat tagagcgaat ttcttatgat ttatgatt                    48

<210> SEQ ID NO 42
<211> LENGTH: 31
<212> TYPE: DNA
<213> ORGANISM: Artificial Sequence
<220> FEATURE:
<223> OTHER INFORMATION: primer

<400> SEQUENCE: 42
tgagctcgtg tggaagaacg attacaacag g                                      31

<210> SEQ ID NO 43
<211> LENGTH: 28
<212> TYPE: DNA
<213> ORGANISM: Artificial Sequence
<220> FEATURE:
<223> OTHER INFORMATION: primer

<400> SEQUENCE: 43
acgcgtcgac tcgtaggaac aatttcgg                                          28

<210> SEQ ID NO 44
<211> LENGTH: 50
<212> TYPE: DNA
<213> ORGANISM: Artificial Sequence
<220> FEATURE:
<223> OTHER INFORMATION: primer

<400> SEQUENCE: 44
cttcttgttt taatgcttct agcattttttt gattaaaatt aaaaaaactt                 50

<210> SEQ ID NO 45
<211> LENGTH: 50
<212> TYPE: DNA
<213> ORGANISM: Artificial Sequence
<220> FEATURE:
<223> OTHER INFORMATION: primer

<400> SEQUENCE: 45 aagtttttt aatttaatc aaaaatgct agaagcatta aacaagaag                      50

<210> SEQ ID NO 46
<211> LENGTH: 46
<212> TYPE: DNA
<213> ORGANISM: Artificial Sequence
<220> FEATURE:
<223> OTHER INFORMATION: primer

<400> SEQUENCE: 46
ggtatatatt taagagcgat ttgtttactt gcgaactgca tgatcc         46

<210> SEQ ID NO 47
<211> LENGTH: 46
<212> TYPE: DNA
<213> ORGANISM: Artificial Sequence
<220> FEATURE:
<223> OTHER INFORMATION: primer

<400> SEQUENCE: 47
ggatcatgca gttcgcaagt aaacaaatcg ctcttaaata tatacc         46

<210> SEQ ID NO 48
<211> LENGTH: 33
<212> TYPE: DNA
<213> ORGANISM: Artificial Sequence
<220> FEATURE:
<223> OTHER INFORMATION: primer

<400> SEQUENCE: 48
cgcagtcgac cttttaaaca gttgatgaga acc         33

<210> SEQ ID NO 49
<211> LENGTH: 676
<212> TYPE: DNA
<213> ORGANISM: Artificial Sequence
<220> FEATURE:
<223> OTHER INFORMATION: promoter

<400> SEQUENCE: 49
tcgagtttat cattatcaat actgccattt caaagaatac gtaaataatt aatagtagtg      60
attttcctaa ctttatttag tcaaaaaatt agccttttaa ttctgctgta acccgtacat     120
gcccaaaata gggggcgggt tacacagaat atataacatc gtaggtgtct gggtgaacag     180
tttattcctg gcatccacta aatataatgg agcccgcttt ttaagctggc atccagaaaa     240
aaaaagaatc ccagcaccaa aatattgttt tcttcaccaa ccatcagttc ataggtccat     300
tctcttagcg caactacaga gaacaggggc acaaacaggc aaaaaacggg cacaacctca     360
atggagtgat gcaacctgcc tggagtaaat gatgacacaa ggcaattgac ccacgcatgt     420
atctatctca ttttcttaca ccttctatta ccttctgctc tctctgattt ggaaaaagct     480
gaaaaaaaag gttgaaacca gttccctgaa attattcccc tacttgacta ataagtatat     540
aaagacggta ggtattgatt gtaattctgt aaatctattt cttaaacttc ttaaattcta     600
cttttatagt tagtcttttt tttagtttta aaacaccaag aacttagttt cgaataaaca     660
cacataaaca aacaaa                                                    676

<210> SEQ ID NO 50
<211> LENGTH: 326
<212> TYPE: DNA
<213> ORGANISM: Artificial Sequence
<220> FEATURE:
<223> OTHER INFORMATION: terminator

<400> SEQUENCE: 50
gcgaatttct tatgatttat gatttttatt attaaataag ttataaaaaa aataagtgta      60
tacaaatttt aaagtgactc ttaggtttta aaacgaaaat tcttattctt gagtaactct     120

```
ttcctgtagg tcaggttgct ttctcaggta tagcatgagg tcgctcttat tgaccacacc      180
tctaccggca tgccgagcaa atgcctgcaa atcgctcccc atttcaccca attgtagata      240
tgctaactcc agcaatgagt tgatgaatct cggtgtgtat tttatgtcct cagaggacaa      300
cacctgttgt aatcgttctt ccacac                                           326

<210> SEQ ID NO 51
<211> LENGTH: 374
<212> TYPE: DNA
<213> ORGANISM: Artificial Sequence
<220> FEATURE:
<223> OTHER INFORMATION: promoter

<400> SEQUENCE: 51
gtgggtgtat tggattatag gaagccacgc gctcaacctg gaattacagg aagctggtaa       60
ttttttgggt ttgcaatcat caccatctgc acgttgttat aatgtcccgt gtctatatat      120
atccattgac ggtattctat ttttttgcta ttgaaatgag cgttttttgt tactacaatt      180
ggttttacag acggaatttt ccctatttgt ttcgtcccat ttttcctttt ctcattgttc      240
tcatatctta aaaggtcct ttcttcataa tcaatgcttt cttttactta atattttact       300
tgcattcagt gaattttaat acatattcct ctagtcttgc aaaatcgatt tagaatcaag      360
ataccagcct aaaa                                                        374

<210> SEQ ID NO 52
<211> LENGTH: 390
<212> TYPE: DNA
<213> ORGANISM: Artificial Sequence
<220> FEATURE:
<223> OTHER INFORMATION: promoter

<400> SEQUENCE: 52
ctcgtaggaa caatttcggg cccctgcgtg ttcttctgag gttcatcttt tacatttgct       60
tctgctggat aattttcaga ggcaacaagg aaaaattaga tggcaaaaag tcgtctttca      120
aggaaaaatc cccaccatct ttcgagatcc cctgtaactt attggcaact gaaagaatga      180
aaaggaggaa aatacaaaat atactagaac tgaaaaaaaa aaagtataaa tagagacgat      240
atatgccaat acttcacaat gttcgaatct attcttcatt tgcagctatt gtaaataat       300 aaaacatcaa gaacaaacaa gctcaacttg tcttttctaa gaacaaagaa taaacacaaa      360
aacaaaaagt tttttttaatt ttaatcaaaa                                      390

<210> SEQ ID NO 53
<211> LENGTH: 302
<212> TYPE: DNA
<213> ORGANISM: Artificial Sequence
<220> FEATURE:
<223> OTHER INFORMATION: terminator

<400> SEQUENCE: 53
acaaatcgct cttaaatata tacctaaaga acattaaagc tatattataa gcaaagatac       60
gtaaattttg cttatattat tatacacata tcatatttct atattttta gatttggtta       120 tataatgtac gtaatgcaaa ggaaataaat tttatacatt attgaacagc gtccaagtaa      180
ctacattatg tgcactaata gtttagcgtc gtgaagactt tattgtgtcg cgaaaagtaa      240
aaattttaaa aattagagca ccttgaactt gcgaaaaagg ttctcatcaa ctgttttaaaa     300 gg                                                                    302
```